United States Patent [19]
Orser et al.

[11] Patent Number: 5,512,478
[45] Date of Patent: Apr. 30, 1996

[54] GENES AND ENZYMES INVOLVED IN THE MICROBIAL DEGRADATION OF PENTACHLOROPHENOL

[75] Inventors: Cindy S. Orser, Boulder, Colo.; Luying Xun, Richland, Wash.; Cleston C. Lange, II, Minneapolis, Minn.

[73] Assignee: Idaho Research Foundation, Inc., Moscow, Id.

[21] Appl. No.: 276,887

[22] Filed: Jul. 18, 1994

Related U.S. Application Data

[63] Continuation-in-part of Ser. No. 914,282, Jul. 13, 1992, Pat. No. 5,364,787, which is a continuation-in-part of Ser. No. 856,015, Mar. 23, 1992, abandoned.

[51] Int. Cl.$^6$ ............................. C12N 15/76; C12N 15/53
[52] U.S. Cl. ................................. 435/252.33; 435/320.1; 435/189; 536/23.2
[58] Field of Search ................................. 435/189, 320.1, 435/252.33; 536/23.2

[56] References Cited

U.S. PATENT DOCUMENTS 4,713,340  12/1987  Crawford .............................. 435/253

OTHER PUBLICATIONS

Orser et al., "Characterization of a *Flavobacterium* Gluthathione S–Transferase Gene Involved in Reductive Dechlorination," *J. Bacteriol.* 175:2640–2644 (1993).

Orser et al., "Cloning, Sequence Analysis, and Expression of the *Flavobacterium* Pentachlorophenol–4–Monooxygenase Gene in *Escherichia coli*," *J. Bacteriol.* 175:411–416 (1993).

Branchaud & Walsh, "Functional Group Diversity in Enzymatic Oxygenation Reactions Catalyzed by Bacterial Flavin–Containing Cyclohexanone Oxygenase," *Am. Chem. Soc.* 1507:2153–61 (1985).

Commandeur & Parsons, "Degradation of Halogenated Aromatic Compounds," *Biodegradation* 1:207–220 (1990).

Englehardt et al., "Transformations of Pentachlorophenol," *Toxicol. & Environ. Chem.* 11:233–252 (1986).

Reiner et al., "Microbial Metabolism of Pentachlorophenol," *PCP: Chemistry, Pharmacology, and Environmental Toxicology*, Plenum Publishing Co., New York, K. R. Rad (ed.), 67–81 (1978).

Saber & Crawford, "Isolation and Characterization of *Flavobacterium* Strains That Degrade Pentachlorophenol," *App. & Environ. Microbiol.* 4 1512–1518 (1985).

Steiert & Crawford, "Catabolism of pentachlorophenol by a *Flavobacterium* sp.," *Biochem. & Biophys. Res. Comm.* 141:825–830 (1986).

Steiert et al., "Degradation of Chlorinated Phenols by a Pentachlorophenol–Degrading Bacterium," *App. & Environ. Microbiol.* 53:907–910 (1987).

Topp et al., "Biodegradation of the Herbicide Bromoxynil (3,5–Dibromo–4–Hydroxybenzonitrile) by Purified Pentachlorophenol Hydroxylase and Whole Cells of *Flavobacterium* sp. Strain ATCC 39723 Is Accompanied by Cyanogenesis," *App. & Environ. Microbiol.* 58:502–506 (1992).

Xun and Orser, "Purification and Initial Characterization of a Periplasmic Protein Involved in Pentachlorophenol Degradation by *Flavobacterium* sp.," 1990 ASM Annual Meeting, Anaheim, Calif. May 13–17 (1990).

Xun & Orser, "Biodegradation of Triiodophenol by Cell–Free Extracts of Pentachlorophenol–Degrading *Flavobacterium* sp.," *Biochem. & Biophys. Res. Comm.* 174:43–48 (1991).

Xun & Orser, "Purification of a *Flavobacterium* Pentachlorophenol–Induced Periplasmic Protein (PcpA) and Nucleotide Sequence of the Corresponding Gene (pcpA)," *J. Bacteriol.* 173:2920–2926 (1991).

Xun & Orser, "Purification and Properties of Pentachlorophenol Hydroxylase, a Flavoprotein from *Flavobacterium* sp. Strain ATCC 39723," *J. Bacteriol.* 173:4447–4453 (1991).

Xun et al., "Diverse Substrate Range of a *Flavobacterium* Penta–Chlorophenol Hydroxylase and the Reaction Stoichiometries," *J. Bacteriol.* 174:2898–2902 (1992).

Xun et al., "Gluthathione Is the Reducing Agent for the Reductive Dehalogenation of Tetrachloro–p–Hydroquinone by Extracts from a *Flavobacterium* sp.," *Biochem. & Biophys. Res. Comm.* 182:361–366 (1992).

Stalker and McBride, "Cloning and Expression in *Escherichia coli* of a *Klebsiella ozaenae* Plasmid–borne Gene Encoding a Nitrilase Specific for the Herbicide Bromoxynil," *Bacteriology* 169:955–960 (Mar. 1987).

Xun et al.,, "Confirmation of Oxidative Dehalogenation of Pentachlorophenolby a *Flavobacterium* Pentachlorophenol Hydroxylase," *J. Bacteriol.*, 174:5745–5747 (1992).

Xun et al., "Purification and Characterization of a Tetrachloro–p–Hydroquinone Reductive Dehalogenase from a *Flavobacterium* sp.," *J. Bacteriol.*, 174:8003–8007 (1992).

Suggs et al., "Use of synthetic oligonucleotides as hybridization probes: Isolation of cloned cDNA sequences for for human $\beta_2$–microglobulin," *Proc. Natl. Acad. Sci.*, USA 78:6613–6617 (1981).

Saiki et al., "Primer–Directed Enzymatic Amplification of DNA with a Thermostable DNA Polymerase," *Science*, 239:487–491 (1987).

Primary Examiner—Charles L. Patterson, Jr.
Attorney, Agent, or Firm—Klarquist Sparkman Campbell Leigh & Whinston

[57] ABSTRACT

Three purified proteins, PcpA, PcpB and PcpC, are disclosed. These proteins are involved in the breakdown of pentachlorophenol (PCP) and other halogenated phenols by the bacterium Flavobacterium sp. Strain ATCC 39723. Three cloned genes, pcpA, pcpB and pcpC, which encode these proteins are also disclosed, as well as two additional genes involved in PCP degradation, pcpD and pcpR. The purified proteins and cloned genes can be used in bioremediation applications.

19 Claims, 17 Drawing Sheets

PcpA:

Met-Glu-Thr-Asn-His-Ile-Thr-Ser-Leu-His-His-Ile-Thr-Ile-
Cys-Thr-Gly-Thr-Ala-Gln-

PcpB:

Ser-Thr-Tyr-Pro-Ile-Asn-Ala-Pro-Gly-Gln-Ser-Ala-Asp-Ala-
Ala-Val-Leu-Ile-Val-Gly-

PcpC:

Pro-Glu-Val-Ser-Leu-Tyr-Asn-Tyr-Thr-Met-Ser-Ile-Cys-Ser-
Met-Lys-Thr-Arg-Leu-Ala-

FIG. 13

FIG. 15A
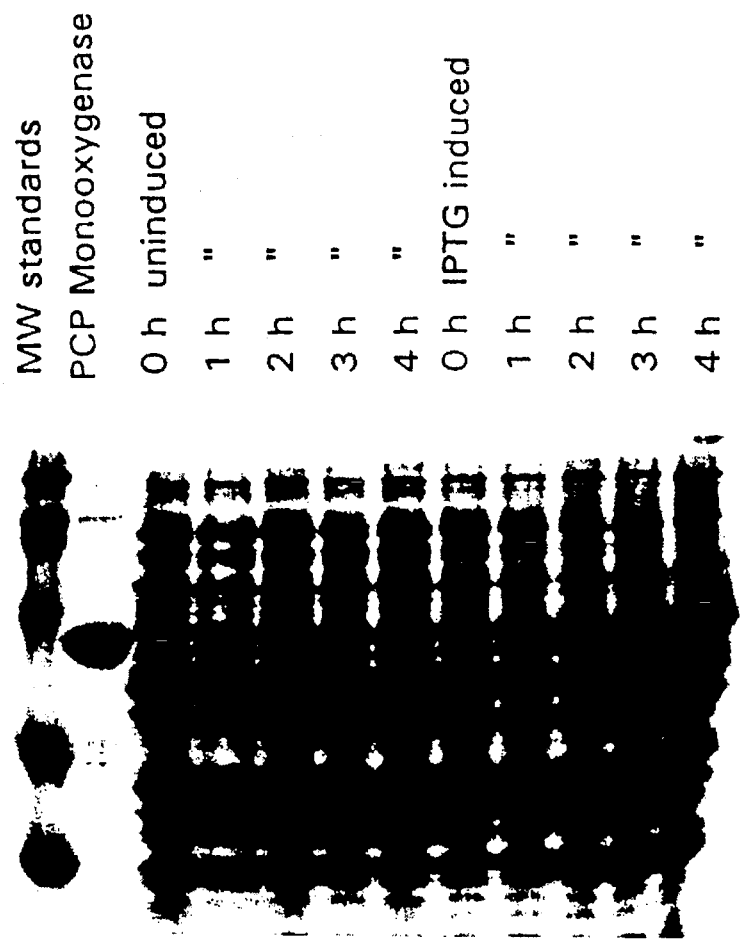
FIG. 15B

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
      ( A ) LENGTH: 1109 base pairs
      ( B ) TYPE: Nucleic Acid
      ( C ) STRANDEDNESS: Double- stranded
      ( D ) TOPOLOGY: Linear ( i i ) MOLECULE TYPE: Genomic DNA
      ( A ) DESCRIPTION:

( i i i ) HYPOTHETICAL: No ( i v ) ANTI-SENSE: No ( v ) FRAGMENT TYPE:

( v i ) ORIGINAL SOURCE:
      ( A ) ORGANISM: Flavobacterium sp. Strain ATCC 39723

( x i ) SEQUENCE DESCRIPTION: SEQ ID NO: 1:

```
CGAAGAAG  CGCCGGAAAA  GCCCAGTATA  GCGCAACGCC  TTCCAGCGCC  AAGGCTATTC                        58

ATTATTCGAA  TGCGGGATAT  TCGCGAACCT  GCGTGGAGCA  AGCACCCGTC  CGATGCTATT                      118

TCAACAATGG  TCCCGCCCCA  TTGCCGCAAG  GTGGAAGAAG  GGCGCGATTC  TTCGGACTTA                      178

TCTTGGAGAG  CGATC GTG GAA ACG AAC CAT ATC ACC AGT CTG CAT CAT                               226
              Met Glu Thr Asn His Ile Thr Ser Leu His His
              1               5                      10

ATC ACC ATC TGC ACC GGC ACG GCG CAG GGG GAC ATC GAT TTC TTC                                 271
Ile Thr Ile Cys Thr Gly Thr Ala Gln Gly Asp Ile Asp Phe Phe
            15                  20                  25

GTG AAG GTC ATG GGC CAG CGC TTC GTG AAG CGC ACG CTG TTC TAT                                 316
Val Lys Val Met Gly Gln Arg Phe Val Lys Arg Thr Leu Phe Tyr
            30                  35                  40

GAC GGC AGC ATT CCC ATC TAT CAC CTG TAC TTC GCG GAC GAA CTG                                 361
Asp Gly Ser Ile Pro Ile Tyr His Leu Tyr Phe Ala Asp Glu Leu
            45                  50                  55

GGC ACG CCC GGC ACC GTC ATG ACC ACC TTC CCC ACC CGC CGC ACC                                 406
Gly Thr Pro Gly Thr Val Met Thr Thr Phe Pro Thr Arg Arg Thr
            60                  65                  70

GGC CAG AAG GGG CGC AAG GGG TCC AAC CAG TTC ACC GTC TGC ACC                                 451
Gly Gln Lys Gly Arg Lys Gly Ser Asn Gln Phe Thr Val Cys Thr
            75                  80                  85

TAC GCC ATC CCC AAG GGG TCG CTG GAA TGG TGG ATC GGC CAT CTG                                 496
Tyr Ala Ile Pro Lys Gly Ser Leu Glu Trp Trp Ile Gly His Leu
            90                  95                  100

AAC GCG CAC GGC ATC GCG ACC GGC GAG CCG GCA CCC GTT TCG GCC                                 541
Asn Ala His Gly Ile Ala Thr Gly Glu Pro Ala Pro Val Ser Ala
            105                 110                 115

AGC GCT ATG TGG GTT TCC AGC ATC CGA CTG CGG ATC GAT TTC GAG                                 586
Ser Ala MET Trp Val Ser Ser Ile Arg Leu Arg Ile Asp Phe Glu
            120                 125                 130

GTG CTG GAG GAT GAG AAT GAC ACG CGT CAG CCC TAT GAC TCG CCC                                 631
Val Leu Glu Asp Glu Asn Asp Thr Arg Gln Pro Tyr Asp Ser Pro
            135                 140                 145

TAT GTC CCC ATC GAG CAT GCG CAC GGC GGC TTC CAT AGC TGG ACG                                 676
Tyr Val Pro Ile Glu His Ala His Gly Gly Phe His Ser Trp Thr
            150                 155                 160

GCG TCG GTC CGC GAG CTG GAG GAC ATG GAC TTC TTC ATG GAG AAT                                 721
Ala Ser Val Arg Glu Leu Glu Asp Met Asp Phe Phe MET Glu Asn
            165                 170                 175

TGC TGG AAT TTC GAG AAG ATC GGC GAG GAA GGC AAC CGT CAC CGC                                 766
Cys Trp Asn Phe Glu Lys Ile Gly Glu Glu Gly Asn Arg His Arg
            180                 185                 190

TAT CGC GTG AAG GGC ACG ACG GAA TCG GGC ACG ATC ATC GAC CTG                                 811
Tyr Arg Val Lys Gly Thr Thr Glu Ser Gly Thr Ile Ile Asp Leu
            195                 200                 205

CTG CAT GAA CCG GAC CGT CGT CAG GGT AGC TGG ACC ATC GCG GAA                                 856
Leu His Glu Pro Asp Arg Arg Gln Gly Ser Trp Thr Ile Ala Glu
            210                 215                 220

GGC ATC ATC CAC CAT GGC GCC TTC GCG GTG CCG GAC ATG GAC ATC                                 901
Gly Ile Ile His His Gly Ala Phe Ala Val Pro Asp Met Asp Ile
            225                 230                 235

CAG GCG CGC ATC AAG TTC GAA ACC GAG GGC GTC GGC TTC ACC GAC                                 946
Gln Ala Arg Ile Lys Phe Glu Thr Glu Gly Val Gly Phe Thr Asp
            240                 245                 250

TTT TCG GAC CGC AAG AAC CGC GGC TAT TTC GAA TCC ACC TAT GTG                                 991
Phe Ser Asp Arg Lys Asn Arg Gly Tyr Phe Glu Ser Thr Tyr Val
            255                 260                 265
CGG ACG CCG GGC GGC TGA TGTTCGAAGC CACCCACAGC CTGGGCTTCA CCCATG       1045
```

Arg Thr Pro Gly Gly
              270

ACGAGGATGA ACGCTCGCTG GGCATGGACC TGAAGGTGTC GCCGCAGTTC GATGACAAGA    1105

AGCA                                                                  1109

( 2 ) INFORMATION FOR SEQ ID NO: 2:

( i ) SEQUENCE CHARACTERISTICS:
        ( A ) LENGTH: 2516 base pairs
        ( B ) TYPE: Nucleic Acid
        ( C ) STRANDEDNESS: Double- stranded
        ( D ) TOPOLOGY: Linear ( i i ) MOLECULE TYPE: Genomic DNA
        ( A ) DESCRIPTION:

( i i i ) HYPOTHETICAL: No ( i v ) ANTI-SENSE: No ( v ) FRAGMENT TYPE:

( v i ) ORIGINAL SOURCE:
        ( A ) ORGANISM: Flavobacterium sp. Strain
            ATCC 39723

( x i ) SEQUENCE DESCRIPTION: SEQ ID NO: 2:

```
     CCTTATG CGGCCGGCAC GCAGGCCTGG TCTGTGCGTG AACCGGGCGG CTTATAGGCT      57

CCCATGGTTT AACTTTGCAA CCATAATGTC GCCGGGCGTT ACCTTTGCGC GATCGCCCGC     117

CCGCAAGACC GATTCCGCCG CAAGCCGCGC TCATTTTCCG GCGCAGGTTA TTCAGGTTCC     177

GAATGCCCCA ATTCGACCGC ACCGCCATCG ACGTTAACA  TCCGCGCCGG GCTTTGATAC     237

CCGGCAAAAG CAAATGACGG CCAAGTTCAT TATGAACAGG CACGTTATTT GGCAGAATCC     297

AAAGTATTCA TCGGGAGAGA GATTGTTATT  ATG TCG ACC TAT CCA ATC AAT GCG     351
                                  Met Ser Thr Tyr Pro Ile Asn Ala
                                   1               5
```

CCG GGC CAA TCC GCC GAT GCC GCG GTT TTG ATC GTC GGC GGC GGG CCG       399
Pro Gly Gln Ser Ala Asp Ala Ala Val Leu Ile Val Gly Gly Gly Pro
         10              15                  20

ACG GGG CTG ATT GCG GCC AAT GAA TTG CTG CGC CGC GGC GTA TCG TGC       447
Thr Gly Leu Ile Ala Ala Asn Glu Leu Leu Arg Arg Gly Val Ser Cys
25              30                  35                  40

CGC ATG ATC GAT CGC CTG CCG GTC GCT CAC CAG ACG TCC AAA TCC TGC       495
Arg Met Ile Asp Arg Leu Pro Val Ala His Gln Thr Ser Lys Ser Cys
                45                  50                  55

ACC ATC CAT GCA AGA TCG ATG GAG ATG ATG GAA CAT ATC GGC ATC GCC       543
Thr Ile His Ala Arg Ser Met Glu Met Met Glu His Ile Gly Ile Ala
            60                  65                  70

GCC CGC TAC ATA GAA ACG GGC GTC AGG AGC AAC GGG TTC ACG TTC AAC       591
Ala Arg Tyr Ile Glu Thr Gly Val Arg Ser Asn Gly Phe Thr Phe Asn
        75                  80                  85

TTC GAG AAT ACG GAT GCG AAC GCG CTG CTC GAC TTT TCC GTC CTG CCG       639
Phe Glu Asn Thr Asp Ala Asn Ala Leu Leu Asp Phe Ser Val Leu Pro
        90                  95                  100

GGC AGA TAT CCG TTC ATC ACC ATC TAT AAC CAG AAT GAA ACC GAA CGG       687
Gly Arg Tyr Pro Phe Ile Thr Ile Tyr Asn Gln Asn Glu Thr Glu Arg
105                 110                 115                 120

GTG CTG CGG CAC GAT CTG GAG GCG ACC TAC AGC TTC CAG CCG GAA TGG       735
Val Leu Arg His Asp Leu Glu Ala Thr Tyr Ser Phe Gln Pro Glu Trp
                125                 130                 135

GGC ACG CAG TTG CTG GCG CTC AAT CAG GAT GAA AAC GGC ATC CGG GCT       783
Gly Thr Gln Leu Leu Ala Leu Asn Gln Asp Glu Asn Gly Ile Arg Ala
            140                 145                 150

| | | | | | | | | | | | | | | | | |
|---|---|---|---|---|---|---|---|---|---|---|---|---|---|---|---|---|
| GAT | CTG | AGG | CTG | AAG | GAC | GGG | ACG | AAG | CAG | ACG | ATC | TCC | CCG | CGC | TGG | 831 |
| Asp | Leu | Arg | Leu | Lys | Asp | Gly | Thr | Lys | Gln | Thr | Ile | Ser | Pro | Arg | Trp | |
| | | 155 | | | | | 160 | | | | | 165 | | | | |
| GTG | ATC | GGC | GCG | GAC | GGC | GTG | CGC | AGC | CGC | GTC | CGC | GAA | TGC | CTG | GGC | 879 |
| Val | Ile | Gly | Ala | Asp | Gly | Val | Arg | Ser | Arg | Val | Arg | Glu | Cys | Leu | Gly | |
| | 170 | | | | | 175 | | | | | 180 | | | | | |
| ATC | GCC | TAT | GAA | GGC | GAG | GAT | TAT | GAA | GAA | AAT | GTC | CTT | CAG | ATG | ATG | 927 |
| Ile | Ala | Tyr | Glu | Gly | Glu | Asp | Tyr | Glu | Glu | Asn | Val | Leu | Gln | Met | Met | |
| 185 | | | | | 190 | | | | | 195 | | | | | 200 | |
| GAC | GTC | GGC | ATC | CAG | GAT | TTC | GAA | GCG | GGC | GAC | GAC | TGG | ATT | CAC | TAT | 975 |
| Asp | Val | Gly | Ile | Gln | Asp | Phe | Glu | Ala | Gly | Asp | Asp | Trp | Ile | His | Tyr | |
| | | | | 205 | | | | | 210 | | | | | 215 | | |
| TTC | ATC | GGT | CAG | GAC | AAA | TTC | GTC | TTC | GTG | ACG | AAG | CTG | CCG | GGT | TCC | 1023 |
| Phe | Ile | Gly | Gln | Asp | Lys | Phe | Val | Phe | Val | Thr | Lys | Leu | Pro | Gly | Ser | |
| | | | 220 | | | | | 225 | | | | | 230 | | | |
| AAT | TAT | CGC | GTG | ATT | ATC | AGC | GAC | CTT | GGC | GGC | GCC | AAC | AAA | TCG | AAT | 1071 |
| Asn | Tyr | Arg | Val | Ile | Ile | Ser | Asp | Leu | Gly | Gly | Ala | Asn | Lys | Ser | Asn | |
| | | 235 | | | | | 240 | | | | | 245 | | | | |
| CTG | GAA | GAA | ACG | CGG | GAA | GCC | TTC | CAG | GGC | TAT | CTC | AGT | TCC | TTC | GAC | 1119 |
| Leu | Glu | Glu | Thr | Arg | Glu | Ala | Phe | Gln | Gly | Tyr | Leu | Ser | Ser | Phe | Asp | |
| | 250 | | | | | 255 | | | | | 260 | | | | | |
| GAT | CAT | GCG | ACG | CTC | GAC | GAG | CCG | CGT | TGG | GCG | ACC | AAA | TGG | CGG | GTG | 1167 |
| Asp | His | Ala | Thr | Leu | Asp | Glu | Pro | Arg | Trp | Ala | Thr | Lys | Trp | Arg | Val | |
| 265 | | | | | 270 | | | | | 275 | | | | | 280 | |
| TGG | AAG | CGG | ATG | GCG | ACG | GCC | TAT | CGC | AAG | GGC | AAC | GTC | TTC | CTG | GCA | 1215 |
| Trp | Lys | Arg | Met | Ala | Thr | Ala | Tyr | Arg | Lys | Gly | Asn | Val | Phe | Leu | Ala | |
| | | | | 285 | | | | | 290 | | | | | 295 | | |
| GGC | GAC | GCG | GCG | CAT | TGC | CAT | TCG | CCG | TCG | GGC | GGC | AGC | GGC | ATG | AAC | 1263 |
| Gly | Asp | Ala | Ala | His | Cys | His | Ser | Pro | Ser | Gly | Gly | Ser | Gly | Met | Asn | |
| | | | 300 | | | | | 305 | | | | | 310 | | | |
| GTC | GGC | ATG | CAG | GAC | GCC | TTC | AAC | CTG | GGC | TGG | AAG | ATC | GCC | ATG | GTG | 1311 |
| Val | Gly | Met | Gln | Asp | Ala | Phe | Asn | Leu | Gly | Trp | Lys | Ile | Ala | Met | Val | |
| | | 315 | | | | | 320 | | | | | 325 | | | | |
| GAA | CGC | GGC | GAA | GCC | AAG | CCC | GAC | CTG | CTC | GAC | ACC | TAT | CAT | ACC | GAA | 1359 |
| Glu | Arg | Gly | Glu | Ala | Lys | Pro | Asp | Leu | Leu | Asp | Thr | Tyr | His | Thr | Glu | |
| | 330 | | | | | 335 | | | | | 340 | | | | | |
| CGG | ACG | CCC | GTC | GCC | CAG | CAG | TTG | CTG | GAA | GGC | ACG | CAC | GCC | ATG | CAT | 1407 |
| Arg | Thr | Pro | Val | Ala | Gln | Gln | Leu | Leu | Glu | Gly | Thr | His | Ala | Met | His | |
| 345 | | | | | 350 | | | | | 355 | | | | | 360 | |
| GAG | ATC | ATC | ATG | GGG | CAT | GGC | AAG | GGC | CTG | ACC | GAC | CGC | ATC | GAA | TTG | 1455 |
| Glu | Ile | Ile | Met | Gly | His | Gly | Lys | Gly | Leu | Thr | Asp | Arg | Ile | Glu | Leu | |
| | | | | 365 | | | | | 370 | | | | | 375 | | |
| ACG | CAG | GCG | CCC | GGT | TGG | CAT | GAC | GCC | GCC | ACC | TAC | CGC | GTG | TCG | GGC | 1503 |
| Thr | Gln | Ala | Pro | Gly | Trp | His | Asp | Ala | Ala | Thr | Tyr | Arg | Val | Ser | Gly | |
| | | | 380 | | | | | 385 | | | | | 390 | | | |
| ATG | TCC | TAT | AAT | TAT | CGC | GAC | CAG | CTC | GTC | AGC | TTC | AAC | GAC | GAC | CGG | 1551 |
| Met | Ser | Tyr | Asn | Tyr | Arg | Asp | Gln | Leu | Val | Ser | Phe | Asn | Asp | Asp | Arg | |
| | | 395 | | | | | 400 | | | | | 405 | | | | |
| CTG | GCC | GGA | CCC | AGC | GCT | GGC | GAC | CGC | ATT | CCC | GAC | GCG | GAA | CTG | GCG | 1599 |
| Leu | Ala | Gly | Pro | Ser | Ala | Gly | Asp | Arg | Ile | Pro | Asp | Ala | Glu | Leu | Ala | |
| | 410 | | | | | 415 | | | | | 420 | | | | | |
| CCC | CGC | ATC | CGG | TTG | TTC | GAC | CTG | GTC | CGC | AAC | ACC | CGG | CCG | ACG | CTG | 1647 |
| Pro | Arg | Ile | Arg | Leu | Phe | Asp | Leu | Val | Arg | Asn | Thr | Arg | Pro | Thr | Leu | |
| 425 | | | | | 430 | | | | | 435 | | | | | 440 | |
| CTC | GTG | GCG | CCC | GCG | ACC | GAA | GCG | GAA | GTG | GCG | GAA | GCG | GAG | AAG | CTG | 1695 |
| Leu | Val | Ala | Pro | Ala | Thr | Glu | Ala | Glu | Val | Ala | Glu | Ala | Glu | Lys | Leu | |
| | | | | 445 | | | | | 450 | | | | | 455 | | |
| CGC | GAC | CTG | ATC | CGC | GAG | CAG | TGG | CCG | CTG | GTG | AAG | CCC | GTC | CTC | GTC | 1743 |
| Arg | Asp | Leu | Ile | Arg | Glu | Gln | Trp | Pro | Leu | Val | Lys | Pro | Val | Leu | Val | |
| | | | 460 | | | | | 465 | | | | | 470 | | | |

| | | | | | | | | | | | | | | | | |
|---|---|---|---|---|---|---|---|---|---|---|---|---|---|---|---|---|
| CGT | CCG | CAG | GGA | AGC | GAG | GAA | TCC | ATC | GAG | GGC | GAC | GTC | CAT | GTC | GAC | 1791 |
| Arg | Pro | Gln 475 | Gly | Ser | Glu | Glu | Ser 480 | Ile | Glu | Gly | Asp | Val | His 485 | Val | Asp | |
| AGC | TAT | GGC | CAG | CTC | AAG | CGC | GAA | TGG | GGC | GAC | AAT | GCG | AAG | GGA | TGG | 1839 |
| Ser | Tyr 490 | Gly | Gln | Leu | Lys | Arg | Glu 495 | Trp | Gly | Asp | Asn | Ala 500 | Lys | Gly | Trp | |
| GCG | GCG | CTG | TTG | AGG | CCG | GAC | AAC | TAC | ATC | CAT | GCG | CGG | GCG | GGC | CTG | 1887 |
| Ala 505 | Ala | Leu | Leu | Arg | Pro 510 | Asp | Asn | Tyr | Ile | His 515 | Ala | Arg | Ala | Gly | Leu 520 | |
| GAT | CGC | GGC | GAT | CTT | CTG | GTC | CAG | GCG | ATC | GAC | GCG | ATG | CTT | GTG | CCG | 1935 |
| Asp | Arg | Gly | Asp | Leu 525 | Leu | Val | Gln | Ala | Ile 530 | Asp | Ala | Met | Leu | Val 535 | Pro | |
| TGC | GCC | TGA | | GGAGACCGT | GCGATGACAA | ACCCGTTTC | GACAATCGAC | | | | | | | | | 1984 |
| Cys | Ala | 539 | | | | | | | | | | | | | | |

ATGACGGTCA CGCAGATCAC CCGCGTGGCC AAGGACATCA ACTCTTACGA ACTTCGCCCG 2044

GAACCCGGCG TGATATTGCC GGAGTTCACC GCGGGGCGC ATATCGGCGT TTCGCTTCCC 2104

AACGGGATCC AGCGCACGTA TTCGCTCGTC AACCCGCAGG CGAGAGGGAC CGTTACGTGA 2164

TCACGGTCAA CCTCGACCGC AACAGCCGGG GCGGTCGCGC TACCTCCACG AGCAGTTGCG 2224

GGTCGGGCAG CGCCTGTCCA TCGTACCGCC CGCCAATAAT TTCGCCCTGG TGGAGACAGC 2284

CCCCCACTCC GTCCTGTTCG CGGGCGGCAT CGGCATCACG CCGATCTGGT CGATGATCCA 2344

ACGGTTGCGG GAACTCGGTT CCACCTGGGA GCTTCATTAC GCCTGTCGCG GCAAGGATTT 2404

CGTCGCCTAC CGCCAGAACT GGAGCAGGCG GCGGCGGAGG CTGGAGCGAG ATCACTCACT 2464

GACCGAAATT CTGACTGCGG CCGTGGCCAG GCGCAGAACG AC 2516

(2) INFORMATION FOR SEQ ID NO: 3:

(i) SEQUENCE CHARACTERISTICS:
           (A) LENGTH: 1432 base pairs
           (B) TYPE: Nucleic Acid
           (C) STRANDEDNESS: Double-stranded
           (D) TOPOLOGY: Linear (ii) MOLECULE TYPE: Genomic DNA
           (A) DESCRIPTION:

(iii) HYPOTHETICAL: No (iv) ANTI-SENSE: NO (v) FRAGMENT TYPE:

(vi) ORIGINAL SOURCE:
           (A) ORGANISM: Flavobacterium sp. Strain ATCC 39723

(xi) SEQUENCE DESCRIPTION: SEQ ID NO: 3:

TAATGCACCG GATCGTGACG TATCCGAACC TGTTGCGGCT GTGGCCAAGC TGCCTCGCAT 60

GAAGCGTCGC GCCCACCATC AATCTCCGCC ATGCCAAGGC CCATTATTAC GGCAGCCATC 120

CAAGCGTGAA TCCCACCGGA ATCGTCCCGT AGCCCCGCCC AACCTGCCGG GCCTAACCCT 180

CCAGTCCTGA CCAAAAAATC CTCCCCATCG AAAGATGGGG AGGGGACCG TTCGCGCAGC 240

GAATGGTGGA GGGGAACTGC GCAGGTCGCG CCATATTTCC TCCACTCCTC CCAAATACAT 300

CCGACAACTG GAATCTGCTT ATCCGATTTG CCCCATGGAC TCTCCAGGGA CGGAACGATA 360

TGCTGCCTCG GCAAAATCGC TGAGGAT ATG AAG ATG CCT GAA GTC AGT CTC TAC 414
                                              Met Asn Met Pro Glu Val Ser Leu Tyr
                                               1                        5

AAT TAC ACC ATG TCG ATC TGT TCG ATG AAG ACC CGT CTG GCG ATG GAG 462

| | | | | | | | | | | | | | | | |
|---|---|---|---|---|---|---|---|---|---|---|---|---|---|---|---|
| Asn | Tyr | Thr | Met | Ser | Ile | Cys | Ser | Met | Lys | Thr | Arg | Leu | Ala | Met | Glu |
| 10 | | | | 15 | | | | | 20 | | | | | 25 | |

| GAA | TTC | GGC | GTC | GAC | TAT | GAC | GAC | AAG | CAG | GTG | GAC | ATC | GGC | TTC | GCC | 510 |
|---|---|---|---|---|---|---|---|---|---|---|---|---|---|---|---|---|
| Glu | Phe | Gly | Val | Asp | Tyr | Asp | Asp | Lys | Gln | Val | Asp | Ile | Gly | Phe | Ala | |
| | | | | 30 | | | | | 35 | | | | | 40 | | |

| CTC | GAA | AAC | TTC | GAA | CCC | GAC | TAT | GTC | CGG | CTG | AAC | GAA | AAG | GCG | GTC | 558 |
|---|---|---|---|---|---|---|---|---|---|---|---|---|---|---|---|---|
| Leu | Glu | Asn | Phe | Glu | Pro | Asp | Tyr | Val | Arg | Leu | Asn | Glu | Lys | Ala | Val | |
| | | | 45 | | | | | 50 | | | | | 55 | | | |

| GTG | CCC | ACG | CTG | GTC | GTC | GGC | GAC | CGC | GTC | GTC | ACC | AAC | AGC | TAC | AAT | 606 |
|---|---|---|---|---|---|---|---|---|---|---|---|---|---|---|---|---|
| Val | Pro | Thr | Leu | Val | Val | Gly | Asp | Arg | Val | Val | Thr | Asn | Ser | Tyr | Asn | |
| | | 60 | | | | | 65 | | | | | 70 | | | | |

| ATC | GTG | CTG | GAG | GCC | GCG | AAC | GTG | GGC | AAG | GTC | GGC | ATT | CCC | GCC | GAC | 654 |
|---|---|---|---|---|---|---|---|---|---|---|---|---|---|---|---|---|
| Ile | Val | Leu | Glu | Ala | Ala | Asn | Val | Gly | Lys | Val | Gly | Ile | Pro | Ala | Asp | |
| | 75 | | | | | 80 | | | | | 85 | | | | | |

| CCG | GTC | GAG | AAC | AAG | GCC | GCG | CTC | GAC | TGG | TTC | CAG | AAG | GGC | GAC | CAG | 702 |
|---|---|---|---|---|---|---|---|---|---|---|---|---|---|---|---|---|
| Pro | Val | Glu | Asn | Lys | Ala | Ala | Leu | Asp | Trp | Phe | Gln | Lys | Gly | Asp | Gln | |
| 90 | | | | 95 | | | | | 100 | | | | | 105 | | |

| GTC | AAT | TTC | CAG | GTC | ATC | ACC | TAT | GGG | CAC | AAG | GGC | GTG | CCG | CGC | GGC | 750 |
|---|---|---|---|---|---|---|---|---|---|---|---|---|---|---|---|---|
| Val | Asn | Phe | Gln | Val | Ile | Thr | Tyr | Gly | His | Lys | Gly | Val | Pro | Arg | Gly | |
| | | | 110 | | | | | 115 | | | | | 120 | | | |

| GAC | GAA | CTG | CTG | ATC | GCG | CGC | CGC | GAA | CGC | GCA | AAG | GAA | TAT | GCC | GAA | 798 |
|---|---|---|---|---|---|---|---|---|---|---|---|---|---|---|---|---|
| Asp | Glu | Leu | Leu | Ile | Ala | Arg | Arg | Glu | Arg | Ala | Lys | Glu | Tyr | Ala | Glu | |
| | | | 125 | | | | | 130 | | | | | 135 | | | |

| AAA | TAT | CCC | GAA | CTG | CGC | TCC | ATC | TAC | CAG | GCC | GCG | CAC | GAC | CGC | ATC | 846 |
|---|---|---|---|---|---|---|---|---|---|---|---|---|---|---|---|---|
| Lys | Tyr | Pro | Glu | Leu | Arg | Ser | Ile | Tyr | Gln | Ala | Ala | His | Asp | Arg | Ile | |
| | | 140 | | | | | 145 | | | | | 150 | | | | |

| GTG | GAA | CAT | GGC | AAT | TGC | GCC | TAT | GAC | GCG | GAC | ACG | GTG | GCC | CAG | GCG | 894 |
|---|---|---|---|---|---|---|---|---|---|---|---|---|---|---|---|---|
| Val | Glu | His | Gly | Asn | Cys | Ala | Tyr | Asp | Ala | Asp | Thr | Val | Ala | Gln | Ala | |
| | 155 | | | | | 160 | | | | | 165 | | | | | |

| GAA | GTC | GAC | CTG | CAA | AAG | CGC | CTC | GAC | GAA | CTG | GAC | GTG | CAT | CTG | GCG | 942 |
|---|---|---|---|---|---|---|---|---|---|---|---|---|---|---|---|---|
| Glu | Val | Asp | Leu | Gln | Lys | Arg | Leu | Asp | Glu | Leu | Asp | Val | His | Leu | Ala | |
| 170 | | | | 175 | | | | | 180 | | | | | 185 | | |

| GAC | AAG | CCG | TTC | ATC | GCG | GGC | AGC | AAC | TAC | AGC | ATC | GCC | GAC | ATC | ATG | 990 |
|---|---|---|---|---|---|---|---|---|---|---|---|---|---|---|---|---|
| Asp | Lys | Pro | Phe | Ile | Ala | Gly | Ser | Asn | Tyr | Ser | Ile | Ala | Asp | Ile | Met | |
| | | | 190 | | | | | 195 | | | | | 200 | | | |

| TGG | ACC | GTC | CTG | CTG | GCG | CGG | ATC | GAG | ATG | CTC | AAC | ATG | ACG | GCC | TGG | 1038 |
|---|---|---|---|---|---|---|---|---|---|---|---|---|---|---|---|---|
| Trp | Thr | Val | Leu | Leu | Ala | Arg | Ile | Glu | Met | Leu | Asn | Met | Thr | Ala | Trp | |
| | | | 205 | | | | | 210 | | | | | 215 | | | |

| ATC | AGC | GAG | CGC | CCG | AAC | CTG | CTC | GCT | TAT | TAT | CAG | CGG | ATG | AAG | GCG | 1086 |
|---|---|---|---|---|---|---|---|---|---|---|---|---|---|---|---|---|
| Ile | Ser | Glu | Arg | Pro | Asn | Leu | Leu | Ala | Tyr | Tyr | Gln | Arg | Met | Lys | Ala | |
| | | 220 | | | | | 225 | | | | | 230 | | | | |

| CGC | CGC | AGC | TTC | GAA | ACG | GCG | CGG | GTG | ATG | CCC | AAT | TGG | AAG | GGC | GGC | 1134 |
|---|---|---|---|---|---|---|---|---|---|---|---|---|---|---|---|---|
| Arg | Arg | Ser | Phe | Glu | Thr | Ala | Arg | Val | Met | Pro | Asn | Trp | Lys | Gly | Gly | |
| | 235 | | | | | 240 | | | | | 245 | | | | | |

| ATC | TGA | CCGTCGCCGG | ATCGGACCAT | TGCCAGGAAA | AAAGGGAAAG | 1180 |
|---|---|---|---|---|---|---|
| Ile | | | | | | |
| 250 | | | | | | |

GCGCGGGAAA CCGCGCCCTT TCCCTTTTTG ATGTTGCGGC CGACCGCAAT GTGGCGATTA 1240

ATAGATATCC GGAAGATGGA TAAGCCAATG AAAACACGGG TCGCGATGTA AAGAAAATC 1300

CGCAATGAAG ATATTCGGCA ATATTAGACA CCTGTCCGAT TTGCAGTCCA GCAACTGGAT 1360

GTTGCCTATC CAATATGCGA TTTGAAAAAA AACAATGCAG CGCTATTCTT CTTTCACTGC 1420

TATTAAGAAT TC 1432

( 2 ) INFORMATION FOR SEQ ID NO: 4:

( i ) SEQUENCE CHARACTERISTICS:
        ( A ) LENGTH: 271 amino acid residues
        ( B ) TYPE: Amino Acid
        ( C ) STRANDEDNESS:
        ( D ) TOPOLOGY: Linear ( i i ) MOLECULE TYPE: Protein
 ( A ) DESCRIPTION:Theoretical translation of
  open reading frame of pcpA
  gene ( i i i ) HYPOTHETICAL:Yes ( i v ) ANTI-SENSE: No ( v ) FRAGMENT TYPE:

( v i ) ORIGINAL SOURCE:
 ( A ) ORGANISM: Flavobacterium sp. Strain
  ATCC 39723

( x i ) SEQUENCE DESCRIPTION: SEQ ID NO: 4:

```
                Met Glu Thr Asn His Ile Thr Ser Leu His His
                  1               5                  10

Ile Thr Ile Cys Thr Gly Thr Ala Gln Gly Asp Ile Asp Phe Phe
             15              20                  25

Val Lys Val Met Gly Gln Arg Phe Val Lys Arg Thr Leu Phe Tyr
             30              35                  40

Asp Gly Ser Ile Pro Ile Tyr His Leu Tyr Phe Ala Asp Glu Leu
             45              50                  55

Gly Thr Pro Gly Thr Val Met Thr Thr Phe Pro Thr Arg Arg Thr
             60              65                  70

Gly Gln Lys Gly Arg Lys Gly Ser Asn Gln Phe Thr Val Cys Thr
             75              80                  85

Tyr Ala Ile Pro Lys Gly Ser Leu Glu Trp Trp Ile Gly His Leu
             90              95                 100

Asn Ala His Gly Ile Ala Thr Gly Glu Pro Ala Pro Val Ser Ala
            105             110                 115

Ser Ala MET Trp Val Ser Ser Ile Arg Leu Arg Ile Asp Phe Glu
            120             125                 130

Val Leu Glu Asp Glu Asn Asp Thr Arg Gln Pro Tyr Asp Ser Pro
            135             140                 145

Tyr Val Pro Ile Glu His Ala His Gly Gly Phe His Ser Trp Thr
            150             155                 160

Ala Ser Val Arg Glu Leu Glu Asp Met Asp Phe Phe MET Glu Asn
            165             170                 175

Cys Trp Asn Phe Glu Lys Ile Gly Glu Gly Asn Arg His Arg
            180             185                 190

Tyr Arg Val Lys Gly Thr Thr Glu Ser Gly Thr Ile Ile Asp Leu
            195             200                 205

Leu His Glu Pro Asp Arg Arg Gln Gly Ser Trp Thr Ile Ala Glu
            210             215                 220

Gly Ile Ile His His Gly Ala Phe Ala Val Pro Asp Met Asp Ile
            225             230                 235

Gln Ala Arg Ile Lys Phe Glu Thr Glu Gly Val Gly Phe Thr Asp
            240             245                 250

Phe Ser Asp Arg Lys Asn Arg Gly Tyr Phe Glu Ser Thr Tyr Val
            255             260                 265

Arg Thr Pro Gly Gly
            270
```

( 2 ) INFORMATION FOR SEQ ID NO: 5:

( i ) SEQUENCE CHARACTERISTICS:
  ( A ) LENGTH: 538 amino acid residues
  ( B ) TYPE:Amino Acid
  ( C ) STRANDEDNESS:

(D) TOPOLOGY: Linear (ii) MOLECULE TYPE: Protein
    (A) DESCRIPTION:Theoretical translation of
                   open reading frame of pcpB
                   gene (iii) HYPOTHETICAL:Yes (iv) ANTI-SENSE: No (v) FRAGMENT TYPE:

(vi) ORIGINAL SOURCE:
    (A) ORGANISM: Flavobacterium sp. Strain ATCC 39723

(xi) SEQUENCE DESCRIPTION: SEQ ID NO: 5:

```
Met Ser Thr Tyr Pro Ile Asn Ala
 1               5

Pro Gly Gln Ser Ala Asp Ala Ala Val Leu Ile Val Gly Gly Gly Pro
         10              15              20

Thr Gly Leu Ile Ala Ala Asn Glu Leu Leu Arg Arg Gly Val Ser Cys
 25              30              35                          40

Arg Met Ile Asp Arg Leu Pro Val Ala His Gln Thr Ser Lys Ser Cys
                 45              50                      55

Thr Ile His Ala Arg Ser Met Glu Met Met Glu His Ile Gly Ile Ala
                 60              65              70

Ala Arg Tyr Ile Glu Thr Gly Val Arg Ser Asn Gly Phe Thr Phe Asn
         75              80              85

Phe Gly Asn Thr Asp Ala Asn Ala Leu Leu Asp Phe Ser Val Leu Pro
     90              95             100

Gly Arg Tyr Pro Phe Ile Thr Ile Tyr Asn Gln Asn Glu Thr Glu Arg
105             110             115                         120

Val Leu Arg His Asp Leu Glu Ala Thr Tyr Ser Phe Gln Pro Glu Trp
                125             130             135

Gly Thr Gln Leu Leu Ala Leu Asn Gln Asp Glu Asn Gly Ile Arg Ala
             140             145             150

Asp Leu Arg Leu Lys Asp Gly Thr Lys Gln Thr Ile Ser Pro Arg Trp
             155             160             165

Val Ile Gly Ala Asp Gly Val Arg Ser Arg Val Arg Glu Cys Leu Gly
     170             175             180

Ile Ala Tyr Glu Gly Glu Asp Tyr Glu Glu Asn Val Leu Gln Met Met
185             190             195                         200

Asp Val Gly Ile Gln Asp Phe Glu Ala Gly Asp Asp Trp Ile His Tyr
             205             210             215

Phe Ile Gly Gln Asp Lys Phe Val Phe Val Thr Lys Leu Pro Gly Ser
             220             225             230

Asn Tyr Arg Val Ile Ile Ser Asp Leu Gly Gly Ala Asn Lys Ser Asn
         235             240             245

Leu Glu Glu Thr Arg Glu Ala Phe Gln Gly Tyr Leu Ser Ser Phe Asp
     250             255             260

Asp His Ala Thr Leu Asp Glu Pro Arg Trp Ala Thr Lys Trp Arg Val
265             270             275                         280

Trp Lys Arg Met Ala Thr Ala Tyr Arg Lys Gly Asn Val Phe Leu Ala
             285             290             295

Gly Asp Ala Ala His Cys His Ser Pro Ser Gly Gly Ser Gly Met Asn
             300             305             310

Val Gly Met Gln Asp Ala Phe Asn Leu Gly Trp Lys Ile Ala Met Val
             315             320             325
```

```
Glu  Arg  Gly  Glu  Ala  Lys  Pro  Asp  Leu  Leu  Asp  Thr  Tyr  His  Thr  Glu
     330                 335                           340

Arg  Thr  Pro  Val  Ala  Gln  Gln  Leu  Leu  Glu  Gly  Thr  His  Ala  Met  His
345                      350                      355                         360

Glu  Ile  Ile  Met  Gly  His  Gly  Lys  Gly  Leu  Thr  Asp  Arg  Ile  Glu  Leu
               365                      370                           375

Thr  Gln  Ala  Pro  Gly  Trp  His  Asp  Ala  Ala  Thr  Tyr  Arg  Val  Ser  Gly
               380                      385                      390

Met  Ser  Tyr  Asn  Tyr  Arg  Asp  Gln  Leu  Val  Ser  Phe  Asn  Asp  Asp  Arg
          395                      400                      405

Leu  Ala  Gly  Pro  Ser  Ala  Gly  Asp  Arg  Ile  Pro  Asp  Ala  Glu  Leu  Ala
     410                 415                      420

Pro  Arg  Ile  Arg  Leu  Phe  Asp  Leu  Val  Arg  Asn  Thr  Arg  Pro  Thr  Leu
425                      430                      435                         440

Leu  Val  Ala  Pro  Ala  Thr  Glu  Ala  Glu  Val  Ala  Glu  Ala  Glu  Lys  Leu
               445                      450                           455

Arg  Asp  Leu  Ile  Arg  Glu  Gln  Trp  Pro  Leu  Val  Lys  Pro  Val  Leu  Val
               460                 465                      470

Arg  Pro  Gln  Gly  Ser  Glu  Glu  Ser  Ile  Glu  Gly  Asp  Val  His  Val  Asp
          475                      480                      485

Ser  Tyr  Gly  Gln  Leu  Lys  Arg  Glu  Trp  Gly  Asp  Asn  Ala  Lys  Gly  Trp
     490                      495                 500

Ala  Ala  Leu  Leu  Arg  Pro  Asp  Asn  Tyr  Ile  His  Ala  Arg  Ala  Gly  Leu
505                      510                      515                         520

Asp  Arg  Gly  Asp  Leu  Leu  Val  Gln  Ala  Ile  Asp  Ala  Met  Leu  Val  Pro
               525                      530                      535

Cys  Ala
538
```

(2) INFORMATION FOR SEQ ID NO: 6:

(i) SEQUENCE CHARACTERISTICS:
(A) LENGTH: 250 amino acid residues
(B) TYPE: Amino Acid
(C) STRANDEDNESS:
(D) TOPOLOGY: Linear (ii) MOLECULE TYPE: Protein
(A) DESCRIPTION:Theoretical translation of
open reading frame of pcpC
gene (iii) HYPOTHETICAL: Yes (iv) ANTI-SENSE: No (v) FRAGMENT TYPE:

(vi) ORIGINAL SOURCE:
(A) ORGANISM: Flavobacterium sp. Strain
ATCC 39723

(xi) SEQUENCE DESCRIPTION: SEQ ID NO: 6:

```
Met  Asn  Met  Pro  Glu  Val  Ser  Leu  Tyr
     1              5

Asn  Tyr  Thr  Met  Ser  Ile  Cys  Ser  Met  Lys  Thr  Arg  Leu  Ala  Met  Glu
10                       15                      20                          25

Glu  Phe  Gly  Val  Asp  Tyr  Asp  Asp  Lys  Gln  Val  Asp  Ile  Gly  Phe  Ala
               30                      35                      40

Leu  Glu  Asn  Phe  Glu  Pro  Asp  Tyr  Val  Arg  Leu  Asn  Glu  Lys  Ala  Val
               45                      50                      55
```

| | | | | | | | | | | | | | |
|---|---|---|---|---|---|---|---|---|---|---|---|---|---|
|Val|Pro|Thr|Leu|Val|Val|Gly|Asp|Arg|Val|Val|Thr|Asn|Ser|Tyr|Asn|
| | |60| | | |65| | | | |70| | | | |
|Ile|Val|Leu|Glu|Ala|Ala|Asn|Val|Gly|Lys|Val|Gly|Ile|Pro|Ala|Asp|
| |75| | | |80| | | |85| | | | | | |
|Pro|Val|Glu|Asn|Lys|Ala|Ala|Leu|Asp|Trp|Phe|Gln|Lys|Gly|Asp|Gln|
|90| | | |95| | | | |100| | | | | |105|
|Val|Asn|Phe|Gln|Val|Ile|Thr|Tyr|Gly|His|Lys|Gly|Val|Pro|Arg|Gly|
| | | |110| | | | |115| | | | |120| | |
|Asp|Glu|Leu|Leu|Ile|Ala|Arg|Arg|Glu|Arg|Ala|Lys|Glu|Tyr|Ala|Glu|
| | | |125| | | |130| | | | |135| | | |
|Lys|Tyr|Pro|Glu|Leu|Arg|Ser|Ile|Tyr|Gln|Ala|Ala|His|Asp|Arg|Ile|
| | |140| | | |145| | | | |150| | | | |
|Val|Glu|His|Gly|Asn|Cys|Ala|Tyr|Asp|Ala|Asp|Thr|Val|Ala|Gln|Ala|
| |155| | | |160| | | | |165| | | | | |
|Glu|Val|Asp|Leu|Gln|Lys|Arg|Leu|Asp|Glu|Leu|Asp|Val|His|Leu|Ala|
|170| | | |175| | | | |180| | | | | |185|
|Asp|Lys|Pro|Phe|Ile|Ala|Gly|Ser|Asn|Tyr|Ser|Ile|Ala|Asp|Ile|Met|
| | | |190| | | |195| | | | |200| | | |
|Trp|Thr|Val|Leu|Leu|Ala|Arg|Ile|Glu|Met|Leu|Asn|Met|Thr|Ala|Trp|
| | |205| | | |210| | | | |215| | | | |
|Ile|Ser|Glu|Arg|Pro|Asn|Leu|Leu|Ala|Tyr|Tyr|Gln|Arg|Met|Lys|Ala|
| |220| | | |225| | | | |230| | | | | |
|Arg|Arg|Ser|Phe|Glu|Thr|Ala|Arg|Val|Met|Pro|Asn|Trp|Lys|Gly|Gly|
| |235| | | |240| | | | |245| | | | | |
|Ile| | | | | | | | | | | | | | | |
|250| | | | | | | | | | | | | | | |

( 2 ) INFORMATION FOR SEQ ID NO: 7:

( i ) SEQUENCE CHARACTERISTICS:
        ( A ) LENGTH: 20 base pairs
        ( B ) TYPE: Nucleic Acid
        ( C ) STRANDEDNESS: Single- stranded
        ( D ) TOPOLOGY: Linear ( x i ) SEQUENCE DESCRIPTION: SEQ ID NO: 7:

ATGGARACNA AYCAYATHAC                                      20

( 2 ) INFORMATION FOR SEQ ID NO: 8:

( i ) SEQUENCE CHARACTERISTICS:
        ( A ) LENGTH: 15 base pairs
        ( B ) TYPE: Nucleic Acid
        ( C ) STRANDEDNESS: Single- stranded
        ( D ) TOPOLOGY: Linear ( x i ) SEQUENCE DESCRIPTION: SEQ ID NO: 8:

DATRTCNCCY TGNGC                                            15

( 2 ) INFORMATION FOR SEQ ID NO: 9:

( i ) SEQUENCE CHARACTERISTICS:
        ( A ) LENGTH: 37 base pairs
        ( B ) TYPE: Nucleic Acid
        ( C ) STRANDEDNESS: Single- stranded
        ( D ) TOPOLOGY: Linear ( x ) SEQUENCE DESCRIPTION: SEQ ID NO: 9:

ACSTAYCCSA TYAAYGCSCC SGGSCARWSS GCSGAYN                  37

( 2 ) INFORMATION FOR SEQ ID NO: 10:

( i ) SEQUENCE CHARACTERISTICS:
        ( A ) LENGTH: 18 amino acid residues
        ( B ) TYPE: Amino Acid ( C ) STRANDEDNESS:
( D ) TOPOLOGY: Linear ( x i ) SEQUENCE DESCRIPTION: SEQ ID NO: 10:

| Pro | Glu | Val | Ser | Leu | Tyr | Asn | Tyr | Thr | Met | Ser | Ile | Xaa | Ser | Met | Lys | Thr | Arg |
|---|---|---|---|---|---|---|---|---|---|---|---|---|---|---|---|---|---|
| 1 | | | | 5 | | | | | 10 | | | | | 15 | | | |

( 2 ) INFORMATION FOR SEQ ID NO: 11:

( i ) SEQUENCE CHARACTERISTICS:
( A ) LENGTH: 36 base pairs
( B ) TYPE: Nucleic Acid
( C ) STRANDEDNESS: Single-stranded
( D ) TOPOLOGY: Linear ( x i ) SEQUENCE DESCRIPTION: SEQ ID NO: 11:

ATSSWCATS GTRTAGTTRT ASAGSSWSAC YTCSGG                 36

( 2 ) INFORMATION FOR SEQ ID NO: 12:

( i ) SEQUENCE CHARACTERISTICS:
( A ) LENGTH: 972 base pairs
( B ) TYPE: Nucleic Acid
( C ) STRANDEDNESS: Double-stranded
( D ) TOPOLOGY: Linear ( i i ) MOLECULE TYPE: Genomic DNA
( A ) DESCRIPTION:

( i i i ) HYPOTHETICAL: No ( i v ) ANTI-SENSE: No ( v ) FRAGMENT TYPE:

( v i ) ORIGINAL SOURCE:
( A ) ORGANISM: Flavobacterium sp. Strain
ATCC 39723

( x i ) SEQUENCE DESCRIPTION: SEQ ID NO: 12:

| ATG | ACA | AAC | CCC | GTT | TCG | ACA | ATC | GAC | ATG | ACG | | | 33 |
|---|---|---|---|---|---|---|---|---|---|---|---|---|---|
| Met | Thr | Asn | Pro | Val | Ser | Thr | Ile | Asp | Met | Thr | | | |
| 1 | | | | 5 | | | | | 10 | | | | |

| GTC | ACG | CAG | ATC | ACC | CGC | GTG | GCC | AAG | GAC | ATC | GGC | TCT | TAC | GAA | 78 |
|---|---|---|---|---|---|---|---|---|---|---|---|---|---|---|---|
| Val | Thr | Gln | Ile | Thr | Arg | Val | Ala | Lys | Asp | Ile | Gly | Ser | Tyr | Glu | |
| | | | 15 | | | | | 20 | | | | | 25 | | |

| CTT | CGC | CCG | GAA | CCC | GGC | GTG | ATA | TTG | CCG | GAG | TTC | ACC | GCG | GGG | 123 |
|---|---|---|---|---|---|---|---|---|---|---|---|---|---|---|---|
| Leu | Arg | Pro | Glu | Pro | Gly | Val | Ile | Leu | Pro | Glu | Phe | Thr | Ala | Gly | |
| | | | 30 | | | | | 35 | | | | | 40 | | |

| GCG | CAT | ATC | GGC | GTT | TCG | CTT | CCC | AAC | GGG | ATC | CAG | CGC | AGC | TAT | 168 |
|---|---|---|---|---|---|---|---|---|---|---|---|---|---|---|---|
| Ala | His | Ile | Gly | Val | Ser | Leu | Pro | Asn | Gly | Ile | Gln | Arg | Ser | Tyr | |
| | | | 45 | | | | | 50 | | | | | 55 | | |

| TCG | CTC | GTC | AAC | CCG | CAG | GGC | GAG | AGG | GAC | CGT | TAC | GTG | ATC | ACG | 213 |
|---|---|---|---|---|---|---|---|---|---|---|---|---|---|---|---|
| Ser | Leu | Val | Asn | Pro | Gln | Gly | Glu | Arg | Asp | Arg | Tyr | Val | Ile | Thr | |
| | | | 60 | | | | | 65 | | | | | 70 | | |

| GTC | AAC | CTC | GAC | CGC | AAC | AGC | CGG | GGC | GGT | TCG | CGC | TAC | CTC | CAC | 258 |
|---|---|---|---|---|---|---|---|---|---|---|---|---|---|---|---|
| Val | Asn | Leu | Asp | Arg | Asn | Ser | Arg | Gly | Gly | Ser | Arg | Tyr | Leu | His | |
| | | | 75 | | | | | 80 | | | | | 85 | | |

| GAG | CAG | TTG | CGG | GTC | GGG | CAG | CGC | CTG | TCC | ATC | GTA | CCG | CCC | GCC | 303 |
|---|---|---|---|---|---|---|---|---|---|---|---|---|---|---|---|
| Glu | Gln | Leu | Arg | Val | Gly | Gln | Arg | Leu | Ser | Ile | Val | Pro | Pro | Ala | |
| | | | 90 | | | | | 95 | | | | | 100 | | |

| AAT | AAT | TTC | GCC | CTG | GTG | GAG | ACA | GCC | CCC | CAC | TCC | GTC | CTG | TTC | 348 |
|---|---|---|---|---|---|---|---|---|---|---|---|---|---|---|---|
| Asn | Asn | Phe | Ala | Leu | Val | Glu | Thr | Ala | Pro | His | Ser | Val | Leu | Phe | |
| | | | 105 | | | | | 110 | | | | | 115 | | |

| GCG | GGC | GGC | ATC | GGC | ATC | ACG | CCG | ATC | TGG | TCG | ATG | ATC | CAA | CGG | 393 |
|---|---|---|---|---|---|---|---|---|---|---|---|---|---|---|---|
| Ala | Gly | Gly | Ile | Gly | Ile | Thr | Pro | Ile | Trp | Ser | Met | Ile | Gln | Arg | |
| | | | 120 | | | | | 125 | | | | | 130 | | |

| | | | | | | | | | | | | | | |
|---|---|---|---|---|---|---|---|---|---|---|---|---|---|---|
| TTG | CGG | GAA | CTC | GGT | TCC | ACC | TGG | GAG | CTT | CAG | GAC | GCC | TGT | CGC | 438
| Leu | Arg | Glu | Leu | Gly | Ser | Thr | Trp | Glu | Leu | Gln | Asp | Ala | Cys | Arg |
| | | | 135 | | | | 140 | | | | | 145 | | |

```
TTG CGG GAA CTC GGT TCC ACC TGG GAG CTT CAG GAC GCC TGT CGC                438
Leu Arg Glu Leu Gly Ser Thr Trp Glu Leu Gln Asp Ala Cys Arg
            135             140                 145

GGC AAG GAT TTC GTC GCC TAC CGC CAG GAA CTG GAG CAG GCG GCG                483
Gly Lys Asp Phe Val Ala Tyr Arg Gln Glu Leu Glu Gln Ala Ala
            150             155                 160

GCG GAG GCT GGA GCG AGA TTC CAC CTC CAC CTC GAT GAA GAG GCC                528
Ala Glu Ala Gly Ala Arg Phe His Leu His Leu Asp Glu Glu Ala
            165             170                 175

GAC GGC AAA TTC CTG GAC CTG GCG GGC CCC GTG GCG CAG GCG GGC                573
Asp Gly Lys Phe Leu Asp Leu Ala Gly Pro Val Ala Gln Ala Gly
            180             185                 190

CAG GAC AGC ATC TTC TAT TGC TGC GGC CCT GAG GCG ATG CTC CAG                618
Gln Asp Ser Ile Phe Tyr Cys Cys Gly Pro Glu Ala Met Leu Gln
            195             200                 205

GCC TAT AAG GCG GCG ACG GGC ACC TGC CGT CCG AAC GGG TGC GGT                663
Ala Tyr Lys Ala Ala Thr Gly Thr Cys Arg Pro Asn Gly Cys Gly
            210             215                 220

TCG AAC ATT CTG CGC GGC CTT GAC GGC GAA CCG GCG GAC GAC GTG                708
Ser Asn Ile Leu Arg Gly Leu Asp Gly Glu Pro Ala Asp Asp Val
            225             230                 235

TTC ACG GTC GTC GTG GCG CGG CGG TCC GGC CAG GAA TTC ACG GTC                753
Phe Thr Val Val Val Ala Arg Arg Ser Gly Gln Glu Phe Thr Val
            240             245                 250

AA CCG GGG ATG ACG ATC CTG GAG ACG CTG CTC CAG AAC GGC ATA                 798
   Glu Pro Gly Met Thr Ile Leu Glu Thr Leu Leu Gln Asn Gly Ile
            255             260                 265

AGC CGG AAT TAC TCC TGC ACC CAG GGC GTC TGC GGC ACC TGC GAG                843
Ser Arg Asn Tyr Ser Cys Thr Gln Gly Val Cys Gly Thr Cys Glu
            270             275                 280

ACC AAG GTG CTG GAG GGC GAA CCC GAT CAT CGC GAC TGG GTC TTG                888
Glu Gly Glu Pro Asp His Arg Asp Trp Val Leu
            285             290
                                                    295

TCC GAC GAG AAG AAG GCG TCA AAT TCG ACC ATG TTG ATC TGC TGT                933
Ser Asp Glu Lys Lys Ala Ser Asn Ser Thr Met Leu Ile Cys Cys
            300             305                 310

TCG CTG AGC AAA TCC CCG CGG CTG GTG CTG GAC ATC TGA                        972
Ser Leu Ser Lys Ser Pro Arg Leu Val Leu Asp Ile
            315             320
```

( 2 ) INFORMATION FOR SEQ ID NO: 13:

( i ) SEQUENCE CHARACTERISTICS:
        ( A ) LENGTH: 912 base pairs
        ( B ) TYPE: Nucleic Acid
        ( C ) STRANDEDNESS: Double-stranded
        ( D ) TOPOLOGY: Linear ( i i ) MOLECULE TYPE: Genomic DNA
        ( A ) DESCRIPTION:

( i i i ) HYPOTHETICAL: No ( i v ) ANTI-SENSE: No ( v ) FRAGMENT TYPE:

( v i ) ORIGINAL SOURCE:
        ( A ) ORGANISM: Flavobacterium sp. Strain ATCC 39723

( x i ) SEQUENCE DESCRIPTION: SEQ ID NO: 13:

```
TT CCG TAT TAC CGC TCG GCC ATC CTG ATG GTC TTC GAC GCC                     45
   Met Ile Pro Tyr Tyr Arg Ser Ala Ile Leu Met Val Phe Asp Ala
              5                10                  15

CTG TAC CGG CAT GGC AGC GCC GGG AAG GCG GCC CAT GCG CTT TCC               90
```

| | | | | | | | | | | | | | | |
|---|---|---|---|---|---|---|---|---|---|---|---|---|---|---|
| | Leu | Tyr | Arg | His | Gly | Ser | Ala | Gly | Lys | Ala | Ala | His | Ala | Leu | Ser |
| | | | | 20 | | | | | 25 | | | | | 30 | |

| ATG | CCC | CAG | CCC | ACG | CTG | AGC | CGC | TGG | CTG | GCG | CAG | TTG | AGG | ACG | 135 |
|---|---|---|---|---|---|---|---|---|---|---|---|---|---|---|---|
| Met | Pro | Gln | Pro | Thr | Leu | Ser | Arg | Trp | Leu | Ala | Gln | Leu | Arg | Thr | |
| | | | | 35 | | | | | 40 | | | | | 45 | |

| CAT | TTC | GAC | GAT | CCC | CTG | TTC | GTG | CGG | ACG | CGA | TCC | GGC | ATG | GAG | 180 |
|---|---|---|---|---|---|---|---|---|---|---|---|---|---|---|---|
| His | Phe | Asp | Asp | Pro | Leu | Phe | Val | Arg | Thr | Arg | Ser | Gly | Met | Glu | |
| | | | | 50 | | | | | 55 | | | | | 60 | |

| CCG | ACG | CCG | CTC | GCC | GCG | CGC | CGC | GCG | CAT | ATC | GCG | GAG | ATG | ATC | 225 |
|---|---|---|---|---|---|---|---|---|---|---|---|---|---|---|---|
| Pro | Thr | Pro | Leu | Ala | Ala | Arg | Arg | Ala | His | Ile | Ala | Glu | Met | Ile | |
| | | | | 65 | | | | | 70 | | | | | 75 | |

| GCC | ATC | TAC | CGC | CAG | CAT | GTC | GCA | GCG | AAC | TGC | GCT | TCG | ATC | CCG | 270 |
|---|---|---|---|---|---|---|---|---|---|---|---|---|---|---|---|
| Ala | Ile | Tyr | Arg | Gln | His | Val | Ala | Ala | Asn | Cys | Ala | Ser | Ile | Pro | |
| | | | | 80 | | | | | 85 | | | | | 90 | |

| GCA | GTC | GAA | CCG | GAA | TTT | CGC | ATA | GCG | GCC | AGC | GAT | TTC | GGA | CAG | 315 |
|---|---|---|---|---|---|---|---|---|---|---|---|---|---|---|---|
| Ala | Val | Glu | Pro | Glu | Phe | Arg | Ile | Ala | Ala | Ser | Asp | Phe | Gly | Gln | |
| | | | | 95 | | | | | 100 | | | | | 105 | |

| GCG | CTG | ATG | CTG | CCC | AGA | CTC | TAT | GCG | ACG | CTG | GAG | GAG | ACC | GCG | 360 |
|---|---|---|---|---|---|---|---|---|---|---|---|---|---|---|---|
| Ala | Leu | Met | Leu | Pro | Arg | Leu | Tyr | Ala | Thr | Leu | Glu | Glu | Thr | Ala | |
| | | | | 110 | | | | | 115 | | | | | 120 | |

| CCT | CAG | GTG | GCT | GAC | GGG | CGT | CAA | TCT | GCG | CCA | CGG | CCC | GCT | GGT | 405 |
|---|---|---|---|---|---|---|---|---|---|---|---|---|---|---|---|
| Pro | Gln | Val | Ala | Asp | Gly | Arg | Gln | Ser | Ala | Pro | Arg | Pro | Ala | Gly | |
| | | | | 125 | | | | | 130 | | | | | 135 | |

| GGA | GGA | ACT | GGA | GTC | CGG | GAG | CAT | CGA | CAT | CGC | GTT | CGG | CGG | ATT | 450 |
|---|---|---|---|---|---|---|---|---|---|---|---|---|---|---|---|
| Gly | Gly | Thr | Gly | Val | Arg | Glu | His | Arg | His | Arg | Val | Arg | Arg | Ile | |
| | | | | 140 | | | | | 145 | | | | | 150 | |

| CCC | AAC | CCT | GTC | GGC | GGG | CAT | CAA | GAC | GCA | GAC | GCT | GTT | CCG | GGA | 495 |
|---|---|---|---|---|---|---|---|---|---|---|---|---|---|---|---|
| Pro | Asn | Pro | Val | Gly | Gly | His | Gln | Asp | Ala | Asp | Ala | Val | Pro | Gly | |
| | | | | 155 | | | | | 160 | | | | | 165 | |

| AGA | ATA | TGT | CTG | CGT | CAT | GCG | GCA | ATC | CCA | TCC | CGC | CCT | GAC | GCA | 540 |
|---|---|---|---|---|---|---|---|---|---|---|---|---|---|---|---|
| Arg | Ile | Cys | Leu | Arg | His | Ala | Ala | Ile | Pro | Ser | Arg | Pro | Asp | Ala | |
| | | | | 170 | | | | | 175 | | | | | 180 | |

| CGG | CCT | GGA | CCT | GGA | GGC | GTT | CCG | GCA | GTG | GCC | CAC | ATC | ATC | ATC | 585 |
|---|---|---|---|---|---|---|---|---|---|---|---|---|---|---|---|
| Arg | Pro | Gly | Pro | Gly | Gly | Val | Pro | Ala | Val | Ala | His | Ile | Ile | Ile | |
| | | | | 185 | | | | | 190 | | | | | 195 | |

| GTG | ACC | GCC | CAT | GAG | TTC | AAT | CAT | GTG | CAT | GAG | CAG | GTG | GAG | GCG | 630 |
|---|---|---|---|---|---|---|---|---|---|---|---|---|---|---|---|
| Val | Thr | Ala | His | Glu | Phe | Asn | His | Val | His | Glu | Gln | Val | Glu | Ala | |
| | | | | 200 | | | | | 205 | | | | | 210 | |

| CGC | CTG | CTG | GAG | CTG | CTG | CCG | CCG | GAA | TCC | ATC | CGC | TTC | ACG | ACG | 675 |
|---|---|---|---|---|---|---|---|---|---|---|---|---|---|---|---|
| Arg | Leu | Leu | Glu | Leu | Leu | Pro | Pro | Glu | Ser | Ile | Arg | Phe | Thr | Thr | |
| | | | | 215 | | | | | 220 | | | | | 225 | |

| GAA | AAC | TTC | CTG | GTC | AGC | GCG | GTC | ATC | GCC | GAG | GAG | ACC | GAC | GTC | 720 |
|---|---|---|---|---|---|---|---|---|---|---|---|---|---|---|---|
| Glu | Asn | Phe | Leu | Val | Ser | Ala | Val | Ile | Ala | Glu | Glu | Thr | Asp | Val | |
| | | | | 230 | | | | | 235 | | | | | 240 | |

| ATC | CTG | ACC | ATA | CCG | TCC | AGG | CTG | GCG | CGA | TGG | TTC | GCC | AAC | CGG | 765 |
|---|---|---|---|---|---|---|---|---|---|---|---|---|---|---|---|
| Ile | Leu | Thr | Ile | Pro | Ser | Arg | Leu | Ala | Arg | Trp | Phe | Ala | Asn | Arg | |
| | | | | 245 | | | | | 250 | | | | | 255 | |

| GGC | GGG | CTG | ACC | ATA | TTT | CCG | GTT | CCG | ATC | GAG | TTG | CCC | TCC | ATC | 810 |
|---|---|---|---|---|---|---|---|---|---|---|---|---|---|---|---|
| Gly | Gly | Leu | Thr | Ile | Phe | Pro | Val | Pro | Ile | Glu | Leu | Pro | Ser | Ile | |
| | | | | 260 | | | | | 265 | | | | | 270 | |

| GAG | GTC | AAG | CAA | TAT | TGG | CAT | GAG | CGC | TAT | GAC | AAG | GAT | CCG | GAA | 855 |
|---|---|---|---|---|---|---|---|---|---|---|---|---|---|---|---|
| Glu | Val | Lys | Gln | Tyr | Trp | His | Glu | Arg | Tyr | Asp | Lys | Asp | Pro | Glu | |
| | | | | 275 | | | | | 280 | | | | | 285 | |

| TAT | CTG | GCT | GCG | CGC | GTG | ATC | GCG | AAG | ATC | GGT | TTC | CAG | AAT | CCG | 900 |
|---|---|---|---|---|---|---|---|---|---|---|---|---|---|---|---|
| Tyr | Leu | Ala | Ala | Arg | Val | Ile | Ala | Lys | Ile | Gly | Phe | Gln | Asn | Pro | |
| | | | | 290 | | | | | 295 | | | | | 300 | |

| CCG | GCG | GAG | TGA | 912 |
|---|---|---|---|---|
| Pro | Ala | Glu | | |

GENES AND ENZYMES INVOLVED IN THE MICROBIAL DEGRADATION OF PENTACHLOROPHENOL

The government has rights in this invention, which was funded in part by grant R-815250-01-0 from the U.S. Environmental Protection Agency and from grant 91-34214-051 from the USDA-NRICGP.

This application is a continuation in part of U.S. patent application Ser. No. 07/914,282, filed Jul. 13, 1992 now U.S. Pat. No. 5,364,787 which is a continuation in part of U.S. patent application Ser. No. 07/856,015, filed Mar. 23, 1992, now abandoned.

FIELD OF THE INVENTION

The present invention concerns genes and purified enzymes involved in the microbial degradation of halogenated phenols.

BACKGROUND OF THE INVENTION

General Discussion of the Background

Halogenated aromatic compounds have been produced industrially on a large scale for several decades. Brominated aromatic compounds have found use as flame retardants, and fluorinated and iodinated aromatic compounds are components of pharmaceutical agents. The chlorinated aromatics have been widely used as pesticides (for example, 2,4-dichlorophenoxyacetic acid and pentachlorophenol) and in industrial settings (for example, polychlorinated biphenyls are employed in electrical equipment and as hydraulic fluids). Typically, these compounds are highly chemically inert, hydrophobic and toxic. Their widespread distribution in the environment is therefore of great concern.

Halogenated phenols comprise a significant subgroup of the halogenated aromatics. The halogenated phenols include pentachlorophenol and its salt, sodium pentachlorophenol. These two compounds (hereinafter referred to collectively as PCP) are among the most widely distributed biocides used in the United States. PCP is an inhibitor of oxidative phosphorylation and, as such, is lethal to a wide variety of organisms, including both plants and animals. PCP is primarily employed by the wood preserving industry as a fungicide and pesticide and is also used in products such as herbicides and disinfectants.

PCP is highly toxic and tends to persist in the environment and within food chains. The adverse effects of low-level PCP contamination on organisms such as fish, shrimp, oysters, clams, and rats are well documented and are reviewed in Rao (1977). A number of studies conclude that contamination of tissues of human populations with PCP at a level of 10 to 20 parts per billion is average for industrialized societies (Rao, 1977). PCP is thought to be mutagenic or at least co-mutagenic, and human exposure to PCP poses significant health hazards.

Removal of PCP and other halogenated aromatics from contaminated environments is therefore an issue of great concern. Methods such as the use of activated charcoal to decontaminate water are currently employed, and efforts have been directed towards the development of bioremediation approaches. Several reports have documented the ability of mixed microbial populations to degrade PCP and other halogenated aromatics. These microbes may be used in combination with existing bioremediation processes and techniques to remove PCP and other halogenated aromatics from contaminated water supplies and soils. Suitable bioremediation techniques include those disclosed in several patents, including U.S. Pat. No. 4,713,340 to Crawford, and East German patent No. 3,601,979 to Debus and Rohde, which describe methods for inoculating bacteria into contaminated environments or materials, including soils and water, and providing conditions under which the inoculated bacterial populations break down the contaminating halogenated aromatics. Another mode of use for such bacteria is disclosed in Japanese patent No. 49094569 to Nishimura in which a crude enzyme extract from a gram-negative bacillus is used to degrade polychlorinated biphenyl.

Further investigations have led to the isolation and characterization of pure strains of bacteria able to degrade halogenated aromatics. In particular, several bacterial strains have been isolated that are capable of breaking down PCP into cellular metabolites. These strains include Arthrobacter sp. Strain ATCC 33790 (Schenk et al., 1989), *Rhodococcus chlorophenolicus* PCP-I (DFN 43826) (Apajalahti and Salkinoja-Salonen, 1987), and Flavobacterium sp. Strain ATCC 39723 as described in U.S. Pat. No. 4,713,340 to Crawford.

The mechanisms by which such microorganisms degrade PCP and other halogenated aromatics are not completely understood. Proposed mechanisms of biodegradation of halogenated aromatics are discussed in Commandeur and Parsons (1990). Microbial metabolism of PCP is addressed in Reiner et al. (1978), and the transformation of PCP under environmental conditions including microbial breakdown has been reviewed by Engelhardt et al. (1986). Based on the isolation of metabolites extracted from culture media, various degradation pathways have been proposed. These pathways have in common the step by step dechlorination of PCP to less chlorinated compounds after which the aromatic ring is cleaved.

Studies of cell extracts from *Rhodococcus chlorophenolicus* have proposed that the initial step of PCP breakdown is hydroxylation to yield tetrachlorohydroquinone (Apajalahti and Salkinoja-Salonen, 1987a) which is subsequently converted to dichlorotrihydroxybenzene by a reaction involving both hydrolytic and reductive dechlorinations (Apajalahti and Salkinoja-Salonen, 1987b). Further dechlorinations then yield 1,2,4 trihydroxybenzene. Trihydrochloroquinone was found to be degraded only very slowly, suggesting that it is not an intermediate in the pathway.

A pathway involving initial hydrolytic dechlorination in the para position of PCP to form 2,3,5,6-tetrachloro-p-hydroquinone (TeCH) and further reductive dechlorinations has been proposed to be responsible for the degradation of PCP by the aerobic Flavobacterium sp. Strain ATCC 39723 (Steiert and Crawford, 1986). This strain is also able to degrade and dechlorinate a range of di, tri and tetrachlorophenols (Steiert et al., 1987). Chlorophenols with chlorine substituents in both ortho (2 and 6) positions were degraded most readily. Of these, 2,4,6-trichlorophenol, 2,3,5,6-tetrachlorophenol and PCP were inducers of the complete PCP degradation pathway.

The microbial breakdown of PCP is thus generally considered to proceed by hydroxylation and dechlorination. The microbes exhibiting PCP breakdown activity must produce enzymes which are able to cleave the carbon-chloride bonds in PCP. However, these and other proteins involved in PCP breakdown have been neither characterized nor purified. Similarly, the genes encoding these enzymes have yet to be identified and cloned.

It is an object of this invention to characterize the process of bacterial PCP breakdown and by so doing to provide information and materials of utility for novel bioremediation technologies.

Specifically, it is an object of this invention to identify and purify enzymes involved in the bacterial breakdown of PCP.

It is another specific object of this invention to identify and clone the genes encoding such enzymes.

It is another object of this invention to provide recombinant DNA vectors which contain the enzymes involved in the bacterial breakdown of PCP, which vectors are capable of directing the expression of these enzymes in heterologous bacterial hosts.

It is a further object of this invention to provide bacteria which are stably transformed with these vectors and which express one or more of the enzymes involved in the bacterial breakdown of PCP.

These and other objects of the invention will be understood more clearly by reference to the following detailed description.

SUMMARY OF THE INVENTION

The foregoing objects have been achieved by the identification and purification of three novel proteins which are present in the PCP degrading bacterium Flavobacterium sp. Strain ATCC 39723 and which are involved in the breakdown of PCP by this organism. These purified proteins are designated PcpA, PcpB and PcpC.

The current invention also includes novel, cloned DNA molecules which include the genes encoding these three proteins. The cloned genes which encode PcpA, PcpB and PcpC are designated pcpA, pcpB and pcpC, respectively. Additionally two other genes that play roles in the microbial degradation of PCP are also encompassed by this invention. These genes are designated pcpD and pcpR.

More specifically, a protein which is shown to be found in the periplasmic space of the Flavobacterium and to be synthesized by the bacterium in response to the presence of PCP has been purified. This new protein, which is herein named PcpA, has a molecular weight of approximately 30,000. PcpA is believed to be involved in PCP breakdown either at the stage of PCP uptake into the cell or as a component of a PCP-degrading enzyme complex.

Two other proteins are identified, characterized and provided in purified form for the first time by this invention. These two proteins, herein named PcpB and PcpC, are shown to be enzymes which catalyze successive steps in the PCP breakdown pathway of the Flavobacterium. PcpB (also termed pentachlorophenol hydroxylase by the inventors) catalyzes the conversion of PCP to 2,3,5,6-tetrachloro-p-hydroquinone (TeCH) in the presence of NADPH and oxygen. Purified PcpB is shown to have a molecular weight of approximately 59,000–63,000.

In the presence of the reduced form of glutathione, PcpC (also termed tetrachlorohydroquinone reductase by the inventors) catalyzes the conversion of TeCH to 2,3,6-trichloro-p-hydroquinone (TrCH) and the conversion of TrCH to 2,6-dichloro-p-hydroquinone (DiCH). Purified PcpC is shown to have a molecular weight of approximately 26,000–29,000.

In combination, these proteins therefore catalyze the initial steps of PCP breakdown by this microorganism.

Purified PcpB is further shown to exhibit a wide substrate diversity, including halogen, nitro, amino and cyano substituted phenols. PcpB is also shown to degrade 3,5-dibromo-4-hydroxybenzonitrile (also known as bromoxynil, a widely used herbicide) to produce 2,6 -dibromo-p-hydroquinone.

Also provided by the present invention are N-terminal amino acid sequences of these proteins. The purified PcpB protein comprises the amino acid sequence: Ser-Thr-Tyr-Pro-Ile-Asn-Ala-Pro-Gly-Gln-Ser-Ala-Asp-Ala-Ala-Val-Leu-Ile-Val-Gly. The purified PcpC protein comprises the amino acid sequence: Pro-Glu-Val-Ser-Leu-Tyr-Asn-Tyr-Thr-Met-Ser-Ile-Cys-Ser-Met-Lys-Thr-Arg-Leu-Ala. These amino acid sequences from proteins pcpB and pcpC are encompassed in SEQ. ID Nos. 5 and 6, respectively, in the accompanying sequence listing. Based on these amino acid sequences, degenerate oligonucleotides are synthesized corresponding to the DNA sequences encoding these amino acid sequences. The use of these oligonucleotides as hybridization probes to isolate DNA molecules from the total DNA of the Flavobacterium is described.

Purified DNA molecules which hybridize to these oligonucleotide probes are also included within the present invention. Specifically, DNA molecules are provided that include the genes encoding PcpA, PcpB and PcpC. A cloned 2.4 kb EcoRI-AccI DNA molecule (that is, a DNA molecule of size 2.4 kb which is defined by recognition sites for the EcoRI restriction enzyme at one end and the AccI restriction enzyme at the other) which encodes PcpA and hybridizes to a 68 bp oligonucleotide derived from the N-terminal amino acid sequence of PcpA is provided herein. Also provided is a cloned 3.0 kb EcoRI fragment of DNA which encodes PcpB and hybridizes to a probe LX-6 derived from the N-terminal amino acid sequence of PcpB. Similarly, a cloned 4.0 kb EcoRI-PstI DNA molecule which encodes PcpC and hybridizes to a probe LX-7 derived from the N-terminal amino acid sequence of PcpC is also provided herein.

Recombinant DNA vectors containing one or more of these DNA fragments are aspects of this invention, as are microorganisms transformed with these vectors. Nucleotide sequences of the genes encoding PcpA, PcpB and PcpC are also included in this invention. A DNA molecule comprising nucleotide bases 328 to 1944 shown in SEQ ID No. 2 which encode the PcpB protein and a DNA molecule comprising nucleotide bases 388 to 1140 shown in SEQ ID No. 3 which encodes the PcpC protein are part of this invention. In addition, the complete amino acid sequences of the PcpA, PcpB and PcpC proteins, derived by theoretical translation of the corresponding DNA sequences, are also provided in this invention; these amino acid sequences are presented in SEQ ID Nos. 4, 5 and 6, respectively.

In addition to DNA molecules that encode the genes pcpA, pcpB and pcpC, the present invention also encompasses the nucleic acid sequences of two additional genes, pcpD and pcpR. These nucleic acid sequences are set forth in SEQ ID Nos. 12 and 13 respectively. The pcpD gene was found to be located immediately adjacent to the pcpB gene on the Flavobacterium genome. Analysis of the pcpD sequence suggests that it encodes a PCP 4-monooxygenase reductase enzyme. Studies suggest that the PcpD protein encoded by pcpD this enzyme transfers electrons from nicotinamide adenine dinucleotide phosphate (NADPH) to the flavin adenine dinucleotide (FAD) prosthetic group of PCP 4-monooxygenase, the enzyme encoded by pcpB. The pcpR gene is thought to encode a transcriptional regulator; the pcpR gene product may play a role in the PCP induction of pcpA, pcpB and pcpD.

Having herein provided the DNA sequences for the genes pcpA, pcpB, pcpC, pcpD and pcpR, correspondingly provided are DNA molecules which hybridize under stringent conditions to one or more of these DNA molecules. Such molecules include DNA molecules differing only by minor sequence changes including nucleotide substitutions, deletions and additions. Also comprehended by this invention are DNA molecules which are fragments of the disclosed cloned DNA molecules, such as oligonucleotides which may be employed as effective DNA hybridization probes or primers useful in the polymerase chain reaction.

Having provided purified PcpA, PcpB and PcpC and cloned DNA molecules which encode these proteins, the present invention also provides for the use of these proteins and DNA molecules in aspects of the bioremediation and dechlorination of PCP containing matter. Improved bioremediation methods comprehended by the current invention include the use of genetically engineered bacteria designed for optimal PCP breakdown characteristics, either in situ or in bioreactors. In this respect, microorganisms transformed with the recombinant DNA vectors will be useful in such bioremediation processes. Encompassed by this invention is a method of dechlorinating PCP comprising exposing material containing PCP to microorganisms transformed with DNA which encodes the PcpB protein. Also encompassed by this invention are transformed microorganisms containing a DNA molecule which encodes the PcpB protein. Additionally, this invention also includes transformed microorganisms containing a DNA molecule which encodes the PcpC protein. Transformed microorganisms containing DNA molecules which encode both of the proteins PcpB and PcpC, as well as transformed microorganisms containing DNA molecules which encode the three proteins PcpA, PcpB and PcpC, are also part of this invention. In addition, the genes pcpD and pcpR, in combination with genes encoding PcpA, PcpB and PcpC may provide effective PCP breakdown systems when introduced into particular types of bacteria.

Another application comprehended by this invention is the use of the purified proteins (either extracted from the Flavobacterium or from the transformed microorganisms expressing the selected enzyme) to remove PCP from contaminated materials. The present invention also includes methods of using purified proteins PcpB and PcpC for dechlorination of PCP and, in the case of PcpB, for degradation of a wide range of other substituted aromatics. The present invention includes a method of dechlorinating PCP comprising exposing material containing PCP to purified PcpB and also comprehends a method of dechlorinating PCP when the method of dechlorinating further comprises exposing the material to purified PcpC.

Monoclonal antibodies raised against each of three purified proteins are also provided by this invention. These monoclonal antibodies may be used to evaluate the production of the three enzymes in novel isolates of PCP-degrading bacteria and also to determine optimal conditions for PCP breakdown by such bacteria.

The present invention also includes an assay that uses monoclonal antibodies raised against PcpB or, more preferably PcpA, to quantitate the level of PCP contamination at environmental locations. Quantitation of PcP contamination is indirectly measured by quantitating the amount of PcpA or PcpB produced in response to the presence of PCP in a given sample by the Flavobacterium cells which are added to that sample.

DNA sequences derived from the provided DNA molecules or parts of these molecules can be employed in a sensitive assay utilizing the polymerase chain reaction for the presence of PCP-degrading microorganisms at contaminated environmental sites. The DNA sequences of the cloned genes may also be used as disclosed in conjunction with molecular cloning techniques to clone homologous genes from other microorganisms.

The purified enzymes and the genes encoding these enzymes which are disclosed in this invention as well as the pcpD and pcpR gene sequences are novel in the field of microbial PCP breakdown. Those skilled in the art will appreciate the wide potential utility of this invention, which is not limited to the specific experimental modes and materials described herein.

The foregoing and other features and advantages of the invention will become more apparent from the following detailed description and accompanying drawings.

BRIEF DESCRIPTION OF DRAWINGS

FIG. 13 is the N-terminal amino acid sequences of the purified proteins PcpA, PcpB and PcpC as determined by protein sequencing of the purified proteins and theoretical translation of the nucleotide sequences of the corresponding genes pcpA, pcpB and pcpC.

FIG. 15, Panel A, shows an SDS-PAGE gel of crude lysates of E. coli JM105 transformed with pCL3.

FIG. 15, Panel B, shows an immunoblot of the SDS-PAGE gel in Panel A. The PcpB protein was detected using polyclonal antibody raised against purified PcpB.

Sequence Listings

Figure 1A:
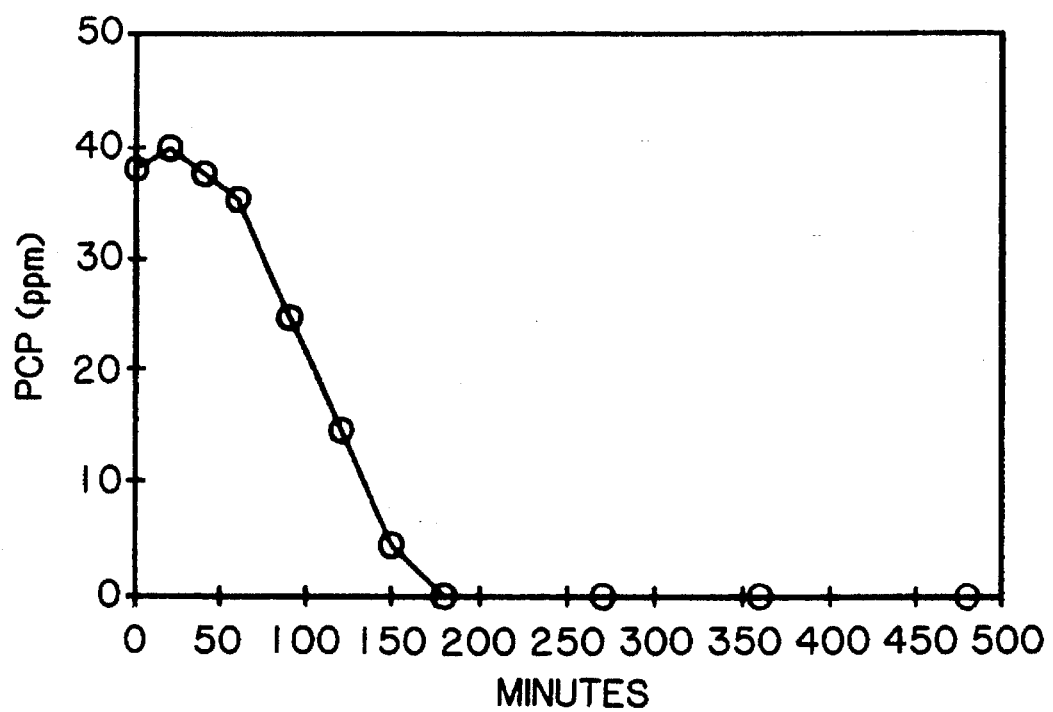
FIG. 1(A) is a graph showing the time course of PCP degradation by Flavobacterium sp. Strain ATCC 39723.

Nucleotide and amino acid sequences are set forth in the "Sequence Listing" appended hereto. Sequence ID No. 1 sets forth the nucleotide sequence of the pcpA gene and the amino acid sequence of the protein encoded by this gene. Sequence ID No. 2 sets forth the nucleotide sequence of the pcpB gene and the amino acid sequence of the protein encoded by this gene. Sequence ID No. 3 sets forth the nucleotide sequence of the pcpC gene and the amino acid sequence of the protein encoded by this gene. Sequence ID Nos. 4, 5 and 6 set forth the amino acid sequences of the proteins PcpA, PcpB and PcpC, respectively. Sequence ID Nos. 7, 8, 9 and 11 set forth the nucleotide sequences of primers LX-1B, LX-2B, LX-6 and LX-7, respectively. Sequence ID No. 10 sets forth the N-terminal amino acid sequence of PcpC as determined by protein sequencing. Sequence ID Nos. 12 and 13 set forth the nucleotide sequences of pcpD and pcpR, respectively.

DETAILED DESCRIPTION

According to the present invention, purified preparations of three bacterial proteins, PcpA, PcpB and PcpC, are provided. As used herein and in reference to the preparations of purified PcpA, PcpB and PcpC, the term "purified" refers to a preparation of a protein (either PcpA, PcpB or PcpC) that is purer than naturally occurring in nature. More specifically, a purified protein is purified to the extent that other proteins represent no more than 50% of the final protein preparation, and more preferably no more than 10% of the final protein preparation. In particularly preferred embodiments, the proteins are purified to provide protein preparations that are essentially free of biological agents normally associated with PcpA, PcpB or PcpC in their in vivo physiological milieu. Such essentially pure enzymes are free of other proteins when assessed electrophoretically by sodium dodecyl sulfate polyacrylamide gel electrophoresis and visualization by staining with Coomassie brilliant blue R-250. In the most preferred embodiments, the proteins are purified to an extent sufficient to allow the determination of N-terminal amino acid sequences by protein sequencing.

Further, DNA molecules encoding these three proteins have been isolated and cloned. These cloned DNA molecules have been incorporated into vectors suitable for the transformation of bacterial cells, each vector carrying a gene which encodes one of the three proteins PcpA, PcpB or PcpC. The three genes which encode the PcpA, PcpB and PcPC proteins are herein named pcpA, pcpB and pcpC, respectively. The DNA molecules, incorporated into recombinant DNA vectors, have been transformed into microorganism host cells. Also provided by this invention are DNA molecules encoding the genes pcpD and pcpR.

Materials and methods used are presented in the following section and with reference to the Figures herein provided. The materials and methods are presented by way of illustration and represent particular embodiments of the invention. Those skilled in the art will recognize that these embodiments can be modified in arrangement and detail without departing from the principles of the present invention.

Bacterial Strains and Sources of Chemicals

Flavobacterium sp. Strain ATCC 39723 was obtained from Dr. R. Crawford (University of Idaho) and is available from the American Type Culture Collection as Accession Number 39723. This microorganism is the subject of U.S. Pat. No. 4,713,340 to Crawford, herein incorporated by reference. The standard laboratory strains Escherichia coli HB101 and JM105 were used as recombinant hosts in cloning experiments.

Flavobacterium strains were cultured in mineral medium with 4 g/l sodium glutamate as the growth substrate, and PCP degradation was induced by adding PCP to a final concentration of 40 µg/ml to cultures at early log phase ($A_{600}<1.0$) (Xun and Orser, 1991a). The induction time required for PCP degradation was usually 1 to 2 hrs. E. coli strains were routinely grown at 37° C. in Luria broth or on Luria agar (Sambrook et al., 1989). The antibiotics tetracycline and ampicillin were used at 15 and 50 µg/ml, respectively. Both antibiotics were purchased from Sigma Chemical Co. (St. Louis, Mo.).

Unless otherwise stated, reagents and enzymes were obtained from the suppliers listed below. Restriction endonucleases, RNA standards, and protein molecular weight standards were purchased from Bethesda Research Laboratories, Inc. (Gaithersburg, Md.), and used as recommended by the supplier. T4 DNA ligase, DNA polymerase I, avian myeloblastosis virus reverse transcriptase, mung bean exonuclease, exonuclease III, random-primed DNA labeling kit, and sequencing reagents were purchased from United States Biochemical Corp., Cleveland, Ohio. X-ray film was purchased from Kodak Co., Rochester, N.Y.; [$\alpha$-$^{32}$P]dCTP, [gamma-$^{35}$S]dATP, and [$\alpha$-$^{35}$S]dATP were from New England Nuclear Corp., Boston, Mass.; DNA Taq polymerase was purchased from Perkin-Elmer Corp. (Norwalk, Conn.). All other chemicals were purchased from Sigma Chemical Co. (St. Louis, Mo.). Standard molecular biology laboratory techniques were performed according to Sambrook et al. (1989) unless stated otherwise.

Identification and Purification of PcpA

The identification and purification of the pentachlorophenol-induced periplasmic protein PcpA are described in Xun and Orser (1991a), herein incorporated by reference.

Identification of PcpA

Subcellular fractions were prepared from Flavobacterium sp. Strain ATCC 39723, as described below, in order to localize PCP degrading activity. PCP degrading activity was assayed by the Leuco crystal violet assay as described below and in Xun and Orser (1991b), herein incorporated by reference. It was found that when cells were broken by sonication or French press that PCP degrading activities ceased and furthermore, that no PCP degrading activity was detectable in cytoplasmic, inner or outer membrane fractions. PCP degrading activity was undetectable in membrane vesicles isolated from the Flavobacterium. It was subsequently determined that the presence of EDTA in the cell suspension buffer was responsible for the arrest of PCP degrading activity. Removal of EDTA by centrifugation and resuspension of the cells in EDTA-free buffer did not restore enzyme activity, leading to the conclusion that EDTA released PCP degrading proteins from the bacterial cell wall.

Figure 1B:
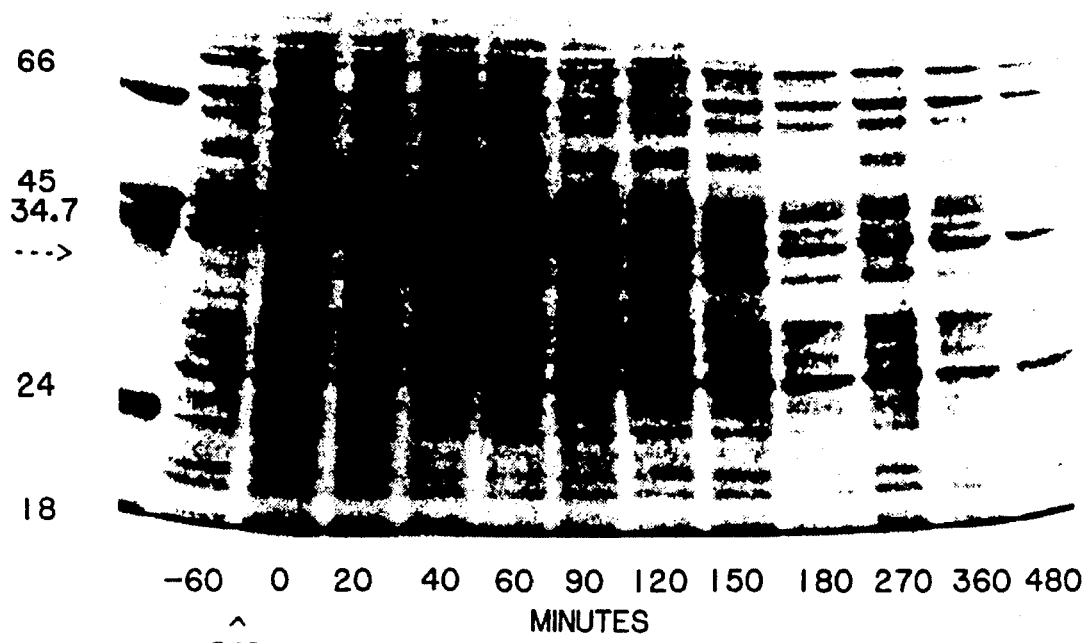
FIG. 1(B) is an SDS-PAGE gel showing PcpA production following induction with PCP.

An additional protein band of approximately 30 kDa. was detected in PCP-induced cells when proteins released by EDTA were separated by sodium dodecyl sulphate polyacrylamide gel electrophoresis (SDS-PAGE). This 30 kDa. protein was found to be required for PCP degradation. Following the addition of PCP to cell medium, this protein was observed to be induced and to reach a maximum intensity as visualized by SDS-PAGE after about one hour and to be essentially absent after six hours. PCP degradation started at 40 min. after the addition of PCP, and the rate reached its maximum at one hour. After six hours, the protein was no longer visible by SDS-PAGE, and the PCP degrading activity could no longer be measured in a culture. These results are shown in FIG. 1. FIG. 1(A) diagrams PCP dechlorination as measured spectrophotometrically following PCP induction at time zero; FIG. 1(B) shows a time course of periplasmic proteins released by EDTA following PCP induction at time zero, monitored by SDS-PAGE. Sizes are indicated in kilodaltons to the left of the gel photograph. The identified 30 kDa. protein was designated PcpA.

PcpA is Absent from 2PCP Mutants

Two PCP mutants, F2 and F23 (Steiert and Crawford, 1986), which do not degrade PCP, did not produce the periplasmic protein PcpA following treatment with PCP. Otherwise, the mutants were identical to the wild type Flavobacterium sp. Strain ATCC 39723 in their growth and periplasmic protein patterns as visualized by SDS-PAGE.

Purification of PcpA

Figure 2:
FIG. 2 is an SDS-PAGE gel of the purified periplasmic protein PcpA.

The 30 kDa. periplasmic protein PcpA was purified from Flavobacterium sp. Strain ATCC 39723 by five successive purification steps: Periplasmic protein extraction, streptomycin sulfate precipitation, ammonium sulfate fractionation, phenyl-agarose hydrophobic chromatography, and DEAE-Sepharose ion exchange chromatography. SDS-PAGE of the purified PcpA protein is shown in FIG. 2. Lane 1 of FIG. 2 shows the purified protein preparation and lane 2 shows the proteins of the periplasmic fraction from PCP-induced cells of Flavobacterium sp. Strain ATCC 39723.

Method of PcpA Purification (i) Periplasmic Protein Extraction. One liter of PCP-induced Flavobacterium cells was harvested by centrifugation at 7,000×g for 10 min. The cells were resuspended in 100 ml of 10 mM EDTA-25 mM Tris (pH 8.0). The cell suspension was kept on ice for one hour and then centrifuged at 7,000×g for 10 min. The supernatant containing the periplasmic proteins was saved.

(ii) Streptomycin Treatment. Solid streptomycin sulfate was added to the supernatant to a final concentration of 0.5% As soon as the streptomycin dissolved, the suspension was centrifuged at 10,000×g for 10 min. and the pellet was discarded.

(iii) Ammonium Sulfate Precipitation. Solid ammonium sulfate was added to the protein solution to 65% saturation. When the ammonium sulfate was completely dissolved, the suspension was left at room temperature for 30 min. The protein precipitate was collected by centrifugation at 10,000×g for 10 min.

(iv) Phenyl-Agarose Chromatography. A column (30 by 1.5 cm) containing 40 ml (bed volume) of phenyl-agarose (Sigma) packed with 20 mM Tris and 2.5 mM EDTA (pH 8.0) in a 6.2° C. cold room was equilibrated with the same buffer containing 20% ammonium sulfate at a flow rate of 30 ml/h via a peristaltic pump (Pharmacia Co., Piscataway, N.J.). The ammonium sulfate precipitate from a 4-liter culture was resuspended in 20 ml of 20 mM Tris-2.5 mM EDTA (pH 8.0) and adjusted to 20% ammonium sulfate by adding solid ammonium sulfate. The solution was centrifuged, the supernatant was loaded onto the phenyl-agarose column, and the protein was eluted with a gradient of 20 to 0% ammonium sulfate in 500 ml of the same buffer. The protein eluted between 7 and 1% ammonium sulfate. Fractions (8 ml) were collected with a microfractionator (Bio-Rad, Richmond, Calif.), and those containing the protein as detected by SDS-PAGE were pooled and concentrated to a volume of 10 ml by dialysis against polyethylene glycol (Sigma) for four hours, using Spectrapor membrane tubing (Spectrum Medical Industries, Inc., Los Angeles, Calif.) with a molecular weight cutoff of 12,000 to 14,000. The sample was further dialyzed against 20 mM Tris (pH 8.0) overnight.

(v) DEAE-Sepharose Chromatography. A column (30 by 1 cm) containing 40 ml of DEAE-Sepharose packed with 20 mM Tris (pH 8.0) in a 6.2° C. cold room was equilibrated with 80 ml of the Tris buffer at a flow rate of 30 ml/h via a peristaltic pump. The 20 mM Tris buffer-dialyzed sample was loaded onto the column and washed with 40 ml of the Tris buffer. The protein was eluted by a linear gradient of 0.1 to 0.4M NaCl in 500 ml of 20 mM Tris (pH 8.0). The protein eluted between 0.24 to 0.29M NaCl. The fractions containing the protein were collected and concentrated to 1 ml by dialysis against polyethylene glycol. The sample was stored at −20° C.

Sodium Dodecyl Sulfate-polyacrylamide Gel Electrophoresis (SDS-PAGE)

Sodium dodecyl sulfate-polyacrylamide gel electrophoresis (SDS-PAGE) was done by the method of Laemmli (1970). Nondenaturing PAGE was done in the same way but without the addition of SDS, and the acrylamide gradient was formed with a gradient maker (Ann Arbor Plastics, Ann Arbor, Mich.). Gels were stained for protein with Coomassie brilliant blue R-250. Protein quantification was performed using the Bradford protein assay (Bradford, 1976).

Identification and Purification of PcpB

The identification and purification of PcpB are described in Xun and Orser (1991c), herein incorporated by reference.

Identification of PcpB

The first step of PCP degradation by microorganisms including Flavobacterium sp. Strain ATCC 39723 is believed to be a hydrolytic dechlorination producing 2,3,5, 6-tetrachloro-p-hydroquinone (TeCH). This strain also degrades triiodophenol (TIP) to produce iodide, which reaction can be measured by the Leuco crystal violet assay. It was concluded that the degradation of PCP to TeCH and the breakdown of TIP to yield iodide proceed by the same mechanism, and that a single hydrolytic enzyme is responsible for both these reactions. A scheme for purifying this enzyme, named pentachlorophenol hydroxylase or PcpB, was therefore devised using the Leuco crystal violet assay as described below to detect the presence of the enzyme.

Purification of PcpB

Purification of PcpB was facilitated by the ability of the enzyme to release iodide from triiodophenol. This activity, as measured by the Leuco crystal violet assay was utilized to detect the presence of PcpB throughout the enzyme purification scheme which is described below. Standard techniques were as described for PcpA purification unless otherwise stipulated.

Method of PcpD Purification

All operations were performed at 4° C., and the buffer was 20 mM Tris hydrochloride (pH 8.0) unless mentioned otherwise. When ammonium sulfate was added, the buffer also contained 1 mM EDTA. Ammonium sulfate saturation levels referred to a temperature of 25° C.

(i) Extraction of Cells. Flavobacterium sp. Strain ATCC 39723 was grown as described above. Frozen (−20° C.) cell paste was thawed in water and suspended in buffer at a concentration of approximately 0.2 g of cells per ml. The protease inhibitor phenylmethylsulfonyl fluoride was freshly prepared in absolute ethanol at a concentration of 250 mM and added to the cell suspension at a final concentration of 5 mM. The slurry was passed through an Aminco French pressure cell (model 4-3398) twice at 12,000 lb/in$^2$. The product was centrifuged at 17,000×g for 10 min., and the supernatant was saved. The precipitate was resuspended in the buffer, passed through a French pressure cell twice, and centrifuged as described above. The supernatant was combined with the previous supernatant, and the precipitate was discarded.

(ii) Protamine Sulfate Fractionation. A 2% solution of protamine sulfate in 20 mM Tris buffer (pH 8.0) was added to the supernatant slowly with constant stirring to a final concentration of 0.1 mg/ml. After 5 min. of stirring, the mixture was centrifuged at 17,000×g for 10 min., and the precipitate was discarded. (iii) Ammonium Sulfate Fractionation. Solid ammonium sulfate was added to the supernatant to 40% saturation with constant stirring. The pH of the solution was not adjusted. After 10 min. of stirring, the mixture was centrifuged (17,000×g for 10 min.), and the precipitate was discarded. Additional solid ammonium sulfate was added to 60% saturation with constant stirring. After 10 min. of stirring, the mixture was centrifuged (17,000×g for 10 min.). The precipitate was saved, and the supernatant was discarded.

(iv) Phenyl Agarose Chromatography. The precipitate was suspended with an equal volume of buffer. The suspension was centrifuged (17,000×g for 10 min.), and the precipitate was discarded. The supernatant was loaded onto a phenyl agarose (Sigma) column (30 by 1.5 cm) previously equilibrated with buffer containing 10% ammonium sulfate. The enzyme was eluted with 300 ml of a 10-to-0% ammonium sulfate gradient. The enzyme eluted to around 5% ammonium sulfate. The fractions containing enzyme activity were pooled and precipitated by adding ammonium sulfate to 70% saturation. The precipitate was collected by centrifugation (17,000×g for 10 min.).

Figure 3:
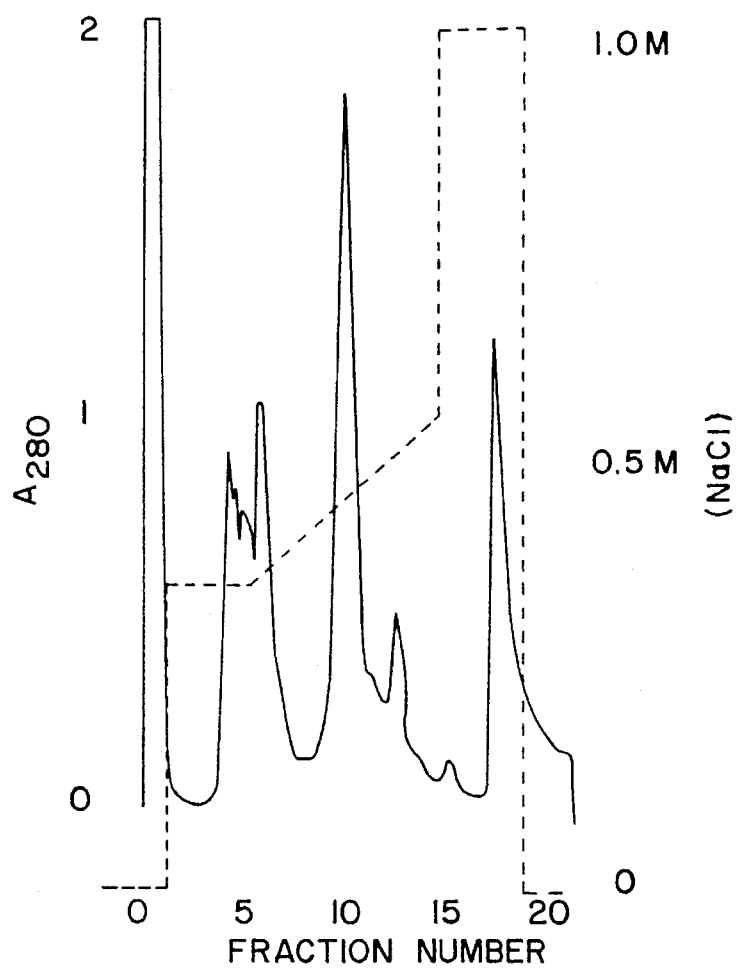
FIG. 3 is a graphic representation of the results of a Mono Q chromatography column run with a step-and-linear gradient of NaCl (—) used for the purification of PcpB.

(v) Mono Q Chromatography. The proteins were resuspended in 3 ml of 20 mM Tris hydrochloride buffer (pH 8) and dialyzed against 1 liter of the same buffer for 1 hour. The protein solution was injected onto a Mono Q HR 5/5 column (Pharmacia) equilibrated with 20 mM Tris buffer. Proteins were eluted with a step-and-linear gradient of sodium chloride (percentage of 1M NaCl in volume of 20 mM Tris: 0%, 2 ml; 35%, 4 ml; 35 to 55%, 9 ml linear gradient; 100%, 4 ml; 0%, 2 ml) by a Pharmacia fast protein liquid chromatography system (FPLC) (Pharmacia LKB Programmer GP-250 Plus and P-500 pump). Fractions of 1 ml were collected. A single PcpB activity peak was associated with a single protein peak around an NaCl concentration of 0.45M. The results of this chromatography are shown in FIG. 3; PcpB activity was associated with the major protein peak at fractions 10 and 11 shown in the figure.

The fractions containing enzyme activity were pooled and precipitated by adding ammonium sulfate to 75% saturation. The precipitate was collected by centrifugation (17,000×g for 10 min.).

Figure 4:
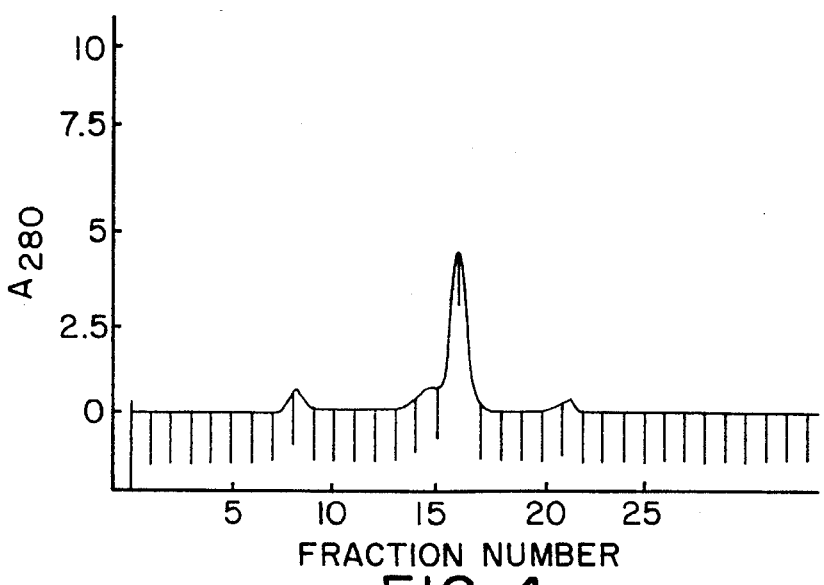
FIG. 4 is a graph showing the results of chromatography on a Superose 6 column with 100 mM NaCl utilized during the purification of PcpB.

(vi) Gel Filtration Chromatography. The protein precipitate was dissolved with an equal volume of buffer and injected onto a Superose 6 column (Pharmacia) equilibrated with 20 mM Tris buffer containing 100 mM NaCl. The enzyme was eluted with the same buffer by the Pharmacia FPLC system. Fractions of 1 ml were collected. PcpB activity was associated with a major protein peak with a retention volume of 16 ml. FIG. 4 shows a typical result obtained from this purification stage; PcpB activity was associated with the major protein peak at fractions 16 and 17. The fractions containing the enzymatic activity were pooled and precipitated by adding ammonium sulfate to 75% saturation. The precipitate was collected by centrifugation (17,000×g for 10 min.).

(vii) Crystallization. The proteins were dissolved with 0.4 ml of saline (0.9%) $KP_i$ buffer (50 mM, pH 7.4) and transferred to a 1.5 ml microcentrifuge tube. Saturated ammonium sulfate solution was added dropwise until a faint, permanent turbidity developed. The sample was then quickly centrifuged (16,000×g for 10 min.) to remove any denatured proteins. Additional ammonium sulfate was added to the supernatant to form microform crystals of the enzyme. The crystal was recovered by centrifugation (16,000×g for 10 min.). The enzyme was stored at −20° C.

Leuco Crystal Violet Assay

The Leuco crystal violet assay was performed as described by Black and Whittle (1967) with the modifications described by Xun and Orser (1991b). All assays were performed in 50 mM Tris-$H_2SO_4$ (pH 8.0) with 100 μM TIP.

Solutions

1) Citric buffer solution, pH 3.8 was prepared as follows: 350 ml 2N $NH_4OH$ solution were added slowly with mixing to 670 ml of 0.333n citric acid solution. 80 g of $NH_{4H}2PO_4$ were then added to the mixture and stirred to dissolve. The pH was adjusted to 3.8.

2) 0.15% potassium monopersulfate triple salt in dd$H_2O$ (Fluka Chemical Co., St. Louis, Mo.).

3) Leuco crystal violet indicator was prepared as follows: 3.2 ml of concentrated sulfuric acid was added to 200 ml dd$H_2O$ in a brown glass container and mixed with a magnetic stir bar at moderate speed. Leuco crystal violet (1.5 g) (Sigma Chemical Co., St. Louis, Mo.) was added along with 800 ml of 0.31% $HgCl_2$ with mixing until the Leuco crystal violet was dissolved. The pH was adjusted to 1.5 or less with $H_2SO_4$.

Free iodide in culture supernatants was measured as follows:

0.5 ml of bacterial culture supernatant was transferred to a 1.5 ml microcentrifuge tube, and 0.1 ml of citric buffer solution (pH 3.8) was added. After mixing, the mixture was centrifuged in a microcentrifuge at 16,000×g for 5 min. A 0.3 ml aliquot of the supernatant was removed to another microcentrifuge tube and diluted to 0.5 ml with dd$H_2O$, and thereafter 10 μl of 0.15% potassium monopersulfate triple salt were added. This was then mixed and left to stand for approximately 1 min. 10 μl of Leuco crystal violet indicator were added, and following further mixing, the preparation was diluted to a volume of 1 ml with dd$H_2O$. Absorbance was then read spectrophotometrically at 592 nm. Iodide standards were prepared in the same buffer solution as in the assay.

Free iodide in enzyme reaction mixtures was measured as follows:

A 0.25 ml sample was placed in a 1.5 ml microcentrifuge tube, 0.05 ml of citric acid buffer were added, and the resulting mixture boiled for 3 min. Thereafter, the tube was centrifuged at 15,000×g for 2 min. 0.25 ml of supernatant were transferred to another 1.5 ml microcentrifuge tube, and 0.25 ml of ddH$_2$O and 10 μl of potassium peroxymonosulfate solution were added. The tube contents were mixed and allowed to stand for 1 min. prior to the addition of 10 μl of crystal violet solution. After this addition, the solutions were further mixed and diluted to 1 ml with ddH$_2$O. Absorbance was measured at 592 nm. The iodide standards were prepared in the same reaction mixture without triiodophenol.

PCP Degradation as an Assay of PcpB Activity

PcpB activity was assayed by measuring the depletion of PCP and/or the production of TECH. The standard assay system contained 100 mM potassium phosphate (KP$_i$) or Tris acetate buffer (pH 7.5), 100 μM NADPH solution, 100 μM PCP, 0.5% Tween 20, 10 μM MgSO$_4$, and enzyme in a 50 μl volume at a constant temperature of 25° C. Tween 20 and MgSO$_4$ were found to increase the dehalogenating activity in the cell extract, and therefore they were included in the standard assay used in enzyme purification. MgSO$_4$ was later determined not to enhance the activity of the purified enzyme. Tween 20 was determined to facilitate reproducible quantitation of PCP by high-performance liquid chromatography (HPLC) analysis as described below. A 10 μl volume of reaction mixture was injected onto the HPLC column at 4 min. after the start of the reaction. One unit of enzyme activity was defined as the amount of enzyme that catalyzed the production of 1 μmol of TeCH or the consumption of 1 μmol of PCP per min under the assay conditions. The reaction rate was linear for about 5 min. with 0.05 to 0.04 U of the enzyme, and then the reaction rate decreased gradually over the next 15 min.

Analytical Methods for PcpB Purification

PCP and TeCH were analyzed by HPLC (Waters, Milford, Mass.) on a Nova-Pak C18 column (3.9 by 150 mm) with an 11 mM H$_3$PO$_4$-acetonitrile gradient (acetonitrile concentrations 10 to 65% [5 min.] and 65% [10 min.]). Maximum absorption at 310, 320, and 330 nm was recorded by use of a Waters 490E programmable multiwavelength UV detector connected to a Maxima NEC computer workstation (Waters). The retention times of PCP and TeCH were 11.5 and 8.9 min., respectively. PCP and TeCH were quantified by comparing their peak areas with the peak areas of authentic standards. NADPH concentration in the reaction mixture was measured by HPLC on the Nova-Pak C18 column with an isocratic 50 mM KP$_i$ buffer (ph 8.0). Flavins were determined by HPLC on a μCarbohydrate analyzing column (3.9 by 300 mm) (Analytical Sciences Incorporated, Santa Clara, Calif.) with an isocratic solution of acetonitrile-distilled water (60:40, vol/vol). Protein purity was checked by HPLC on a Delta Pak C18 30 nm column (3.9 by 150 mm) with a water-acetonitrile gradient containing 0.1% trifluoroacetic acid (acetonitrile concentrations, 15% [1 min.], 15 to 40% [1 min.], 40% [2 min.], 40 to 75% [8 min.], 75 to 100% [1 min.], 100% [7 min.], 100 to 15% [1 min.]) at a flow rate of 1 ml/min.

Results

The results of a typical PcpB purification are summarized in Table 1.

TABLE 1

| | Purification of PcpB | | | | |
|---|---|---|---|---|---|
| | Vol | Protein | Activity[a] | | Recovery |
| Purification Step | (ml) | (mg) | Total | Specific | (%) |
| Crude extract | 72.00 | 1,849 | 133.1 | 0.072 | 100 |
| Protamine sulfate fractionation | 74.00 | 1,398 | 132.8 | 0.095 | 100 |
| Ammonium sulfate fractionation (40 to 60%) | 18.00 | 460 | 127.4 | 0.277 | 95.7 |
| Phenyl agarose chromatography | 5.50 | 62 | 117.9 | 1.89 | 88.6 |
| Mono Q chromatography | 0.72 | 9 | 89.7 | 9.75 | 67.4 |
| Superose 6 chromatography | 0.55 | 6 | 62.5 | 11.00 | 47.0 |
| Crystallization | 0.61 | 5 | 55.4 | 11.54 | 41.6 |

[a]Activity was estimated by TeCH production in 100 mM KP$_i$ buffer (pH 7.5). TeCH standards were prepared in the reaction mixture without PCP and incubated at room temperature for 4 min. before being analyzed by HPLC.

Figure 5:
FIG. 5 is an SDS-PAGE gel of purified PcpB.

Since the enzyme also converts PCP to TeCH, the enzymatic activities in Table 1 were determined from TeCH production, as described above. In the reaction mixture containing crude cell extract, only a very small quantity of TeCH was detected by HPLC, about 1 to 2 μM within 4 min., which gave a distinct peak by HPLC analysis. There was no TeCH detectable after 15 min. of incubation with crude extracts. The purification scheme, consisting of seven steps, resulted in a 160-fold purification of PcpB relative to the crude cell extract (the specific activity increased from 0.072 to 11.51 U/mg of protein). In preferred embodiments, purified PcpB has a specific activity greater than 1 U/mg of protein, and in a most preferred embodiment, purified PcbB has a specific activity greater than 10 U/mg protein. Approximately 41.6% of the activity of PcpB in the crude extract was recovered. A typical elution profile of the proteins chromatographed on an FPLC Mono Q column (Pharmacia) is shown in FIG. 3. The activity of PcpB was found only in a large protein peak located in fractions 10 and 11, a 2 ml volume. The peak was not present when proteins from PCP-uninduced cells were chromatographed, indicating that the enzyme is PCP induced. After Mono Q chromatography, the proteins were chromatographed on a Superose 6 column (Pharmacia), and a typical chromatograph is shown in FIG. 4. After crystallization, PcpB was a single band by SDS-PAGE analysis; FIG. 5 shows a typical gel with molecular size markers (in kilodaltons) in lane 1 and 2.5 μg of PcpB in lane 2. Also, after crystallization, PcpB was detected as a major peak which represented 95% of the total peak area on reverse-phase HPLC column chromatography.

Figure 6:
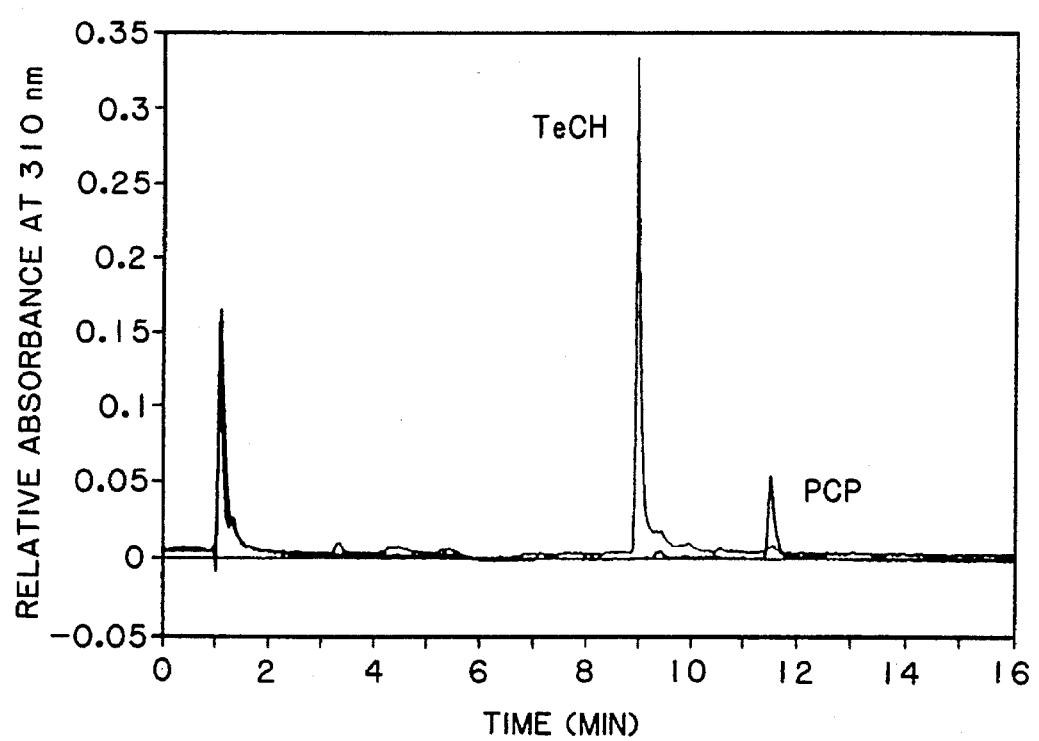
FIG. 6 is a graphic representation illustrating the complete conversion of PCP to TeCH by purified PcpB as measured by HPLC of the reaction mixture.

After the initial purification of PcpB by using TIP as the substrate, PCP was tested as the substrate. PCP and TeCH were quantified by HPLC as described below. PCP was subsequently used in place of TIP for routine enzyme purification. The enzyme completely converted 37 μM PCP to TeCH in 100 mM KP$_i$ buffer (pH 7.0) within 20 min. in the presence of 100 μM NADPH (FIG. 6). The reaction was confirmed to be enzymatic because controls without enzyme or with boiled enzymes exhibited no change in PCP concentration after one hour of incubation. The TeCH produced displayed the same retention time on HPLC as authentic TECH.

Properties of PcpB

The molecular weight of PcpB was estimated to be about 63,000 (FIG. 5). A major band with a molecular weight of 63,000 and a minor band of molecular weight 132,000 were detected on a native gradient PAGE, indicating that it exists mainly as a monomer but also can associate as dimers under native electrophoresis conditions. For gel filtration, when the elution buffer contained 100 mM NaCl, the protein eluted as a single peak on a Superose 6 column (Pharmacia) with a retention volume of 16.0 ml, which was the same as the retention volume of bovine serum albumin (16.0 ml). When NaCl was not used in the elution buffer, the protein eluted as a single peak with a retention volume of 12.8 ml. The data from gel filtration chromatography indicated that the protein was a monomer with a molecular weight of 66,000 when NaCl was used in the elution buffer and that the protein was a multimer with a molecular weight higher than 300 kDa when NaCl was not used in the elution buffer. Since NaCl was not included in the reaction mixture, the enzyme existed as a multimer and therefore the multimer is functional. The discrepancy between the molecular weights of PcpB determined by SDS-PAGE and gel filtration is likely accounted for by differences between the two techniques and inherent experimental variation. Multimeric forms of PcpB, defined as a protein polymer with repeating subunits of PcpB and having the activity of converting PCP to TeCH, are therefore comprehended by this invention. The isoelectric point (pI) of the purified protein was determined to be approximately 4.3 by isoelectric focusing (IEF).

Figure 7:
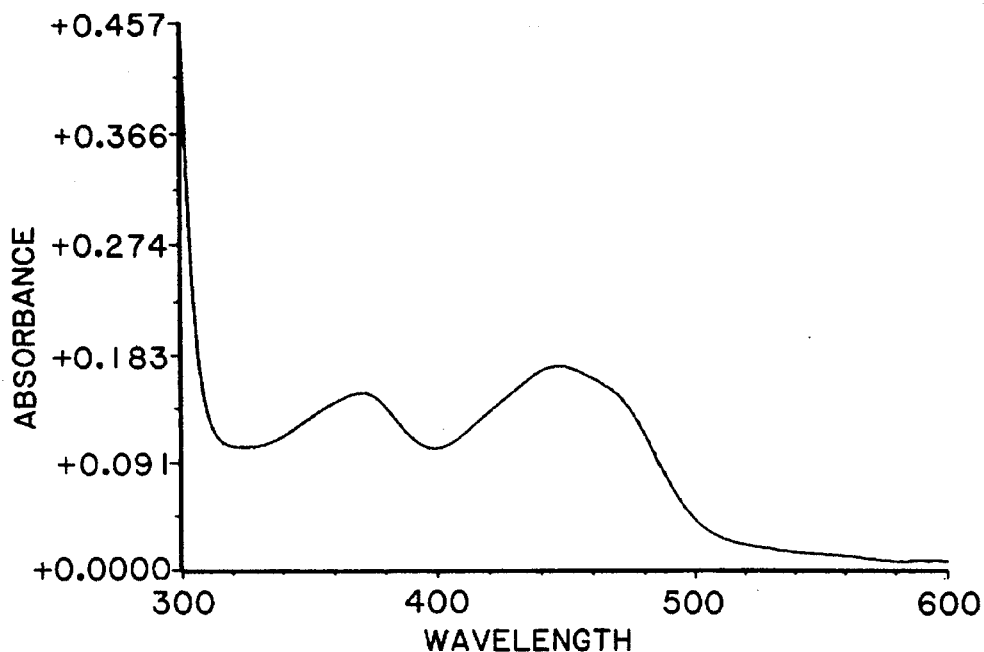
FIG. 7 is an absorbance spectrum of PcpB.

The enzyme was a flavoprotein exhibiting a typical flavoprotein spectrum, with a peak at 446 nm. FIG. 7 shows a typical absorbance spectrum for PcpB determined with a protein solution contained 24.2 µM PcpB in 20 mM Tris hydrochloride (pH 8.0). The addition of NADPH to 150 µM did not reduce the flavoprotein absorption at 446 nm. A solution containing 24.2 µM protein (1.5 mg of protein per ml; molecular weight, 63,000) gave an $A_{446}$ of 0.175. The flavin content was calculated to be 15.5 µM by using a molar extinction coefficient of 11,300 for flavin adenine dinucleotide (FAD) (Strickland and Massey, 1973). The molar ratio of flavin to protein was 0.64. The result indicated that each PcpB molecule contained one flavin molecule. The reduced amount of flavin present in the purified protein could be due to the loss of the flavin during purification. The loss of flavin during purification of other flavin monooxygenases has been reported (Flashner and Massey, 1974; Strickland and Massey, 1973). The flavin in the protein was easily extracted by trichloroacetic acid (Mayhew and Massey, 1969) and was identified as FAD on the basis of the retention time by HPLC (retention times, 5.5 min. [flavin mononucleotide, FMN] 7.1 min. [FAD], and 7.1 min. [sample]).

The enzyme was very stable as both an ammonium sulfate precipitate and in solution at a concentration greater than 1 mg/ml at −20° C. There was no measurable loss of activity over a period of 2 months. At 4° C., about 50% of the activity was gone after 1 week. Enzymatic activity in the cell extract and in the 40 to 60% ammonium sulfate precipitation fraction was completely lost after 3 days at 4° C.

Optimal Conditions for Enzymatic Activity of PcpB

Figure 8:
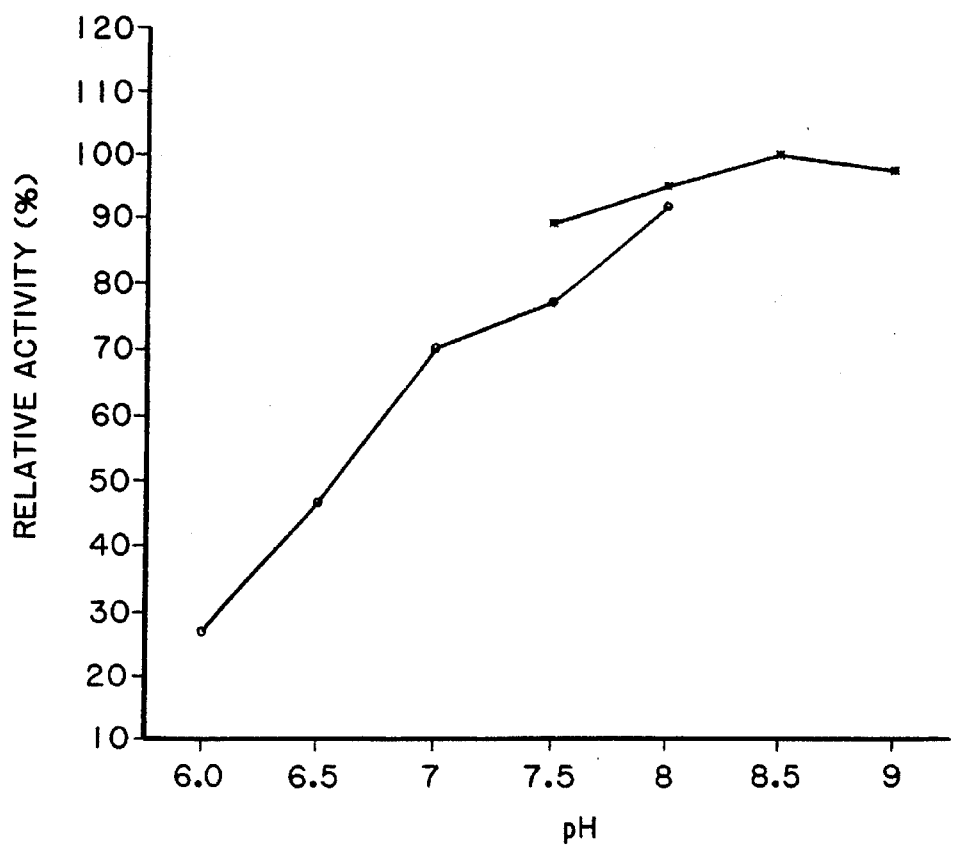
FIG. 8 is a graph showing the effect of pH on PcpB activity.

Results from studies of PcpB activity at different pH values are shown in FIG. 8. In FIG. 8, points marked ○ represent activity assayed in 100 mM $KP_i$ buffer, points marked * represent activity assayed in 100 mM Tris buffer.

The optimal pH for PcpB activity was between 7.5 and 9.0. However, under the optimal pH conditions, the enzymatic product, TeCH, was highly unstable. TeCH oxidized and polymerized to a more hydrophilic compound which was eluted from the reverse-phase HPLC column in the void volume. At a pH lower than 7.5, TeCH was relatively stable. At pHs 7.0, 6.5, and 6.0, the enzyme activity levels were about 90, 57, and 28%, respectively, of that at pH 7.5. The optimal temperature of the enzymatic reaction was between 35° and 40° C. Greater than 75% of the maximal activity was retained at 45° C. The enzymatic activity was completely absent at 50° C. For the purified enzyme, $MgSO_4$ was not required for activity because the addition of $MgSO_4$ or EDTA to 5 mM did not influence the enzymatic activity. This indicates that the enzyme does not require divalent cations for enzymatic activity. Non-ionizing detergents were not required for enzymatic activity for the purified enzyme, as measured by TeCH production. However, Tween 20 was left in the reaction assay because it was found to contribute to the reproducibility of results in the quantitation of PCP by HPLC analysis.

Methods for Determination of pH and Temperature Optima for PcpB

PcpB activity was measured at various pH values within the rage of 6.0 to 9.0 by using 100 mM $KP_i$ buffer (pH 60 to 8.0) or 100 mM Tris acetate buffer (pH 7.5 to 9.0) in a total volume of 50 µl. The enzyme reaction mixture was otherwise the same as defined above for the enzyme assay. The temperature optimum for the enzyme activity was determined in a similar way in $KP_i$ buffer (pH 7.5). The reaction mixture without NADPH was incubated at the corresponding temperature for 4 min., and then 0.5 µl of 10 mM NADPH solution was added to the reaction mixture to start the reaction.

Determination of the Isoelectric Point of PcpB

The isoelectric point (pI) of PcpB was determined using analytical isoelectric focusing (IEF) gels which comprised 5% acrylamide and contained commercially available ampholytes (LKB, Bromma, Sweden) (pH 3.5 to 10). IEF gels were run on an LKB 2117 Multiphor II electrophoresis system as directed by the manufacturer (LKB). A 10 µg amount of purified protein was applied to the IEF gel, and the pI was estimated from the IEF markers (Sigma).

PcpB Exhibits a Diverse Substrate Range

The ability of Flavobacterium sp. Strain ATCC 39723 to degrade chlorinated phenols, triiodophenol, and tribromophenol has previously been reported (Steiert et al., 1987; Xun and Orser, 1991b). The work reported by Xun et al. (1992a) herein incorporated by reference and described below, indicates that PcpB catalyzes the primary metabolic attack on these compounds. PcpB displaces an unusually diverse range of substituents from the para position of polyhalogenated phenols. In addition to removal of halogen, PcpB removes nitro, amino, and cyanol groups from a benzene ring. PcpB also converts 3,5-dibromo-4-hydroxy-benzonitrile (also known as bromoxynil, a widely used herbicide) to 2,6-dibromo-p-hydroquinone. The substrates for PcpB reported here are just those compounds tested to date; the enzyme may use additional substrates not tested. This work demonstrates that PcpB utilizes a wide substrate range, and that the gene which encodes this enzyme would be appropriate for use in constructing many microorganisms with novel biodegradative phenotypes using recombinant DNA techniques.

Methods for Determining PcpB Substrates

Stock Solutions

A stock solution of PCP (concentration, 37.6 mM) was prepared in 0.2M NaOH and stored in the dark at room temperature. Stock solutions of all other halogenated aromatic compounds (concentration, 20 mM) were prepared in absolute ethanol and stored at 4° C. in the dark. The NADPH solution of 10 mM was freshly prepared in 1 mM dithiothreitol and 1 mM Tris base (pH 13).

Enzyme Reaction Conditions

PcpB was purified as described above. Enzyme reactions were conducted in 80 mM potassium phosphate buffer (pH 7.5) with 0.5% Tween 20 at 23° C. The enzyme concentration was 500 µg/ml in all reactions.

Analytical Methods for Determining PcpB Substrate Range

All of the aromatic substrates and the corresponding enzyme product (aromatic portion) were monitored by reverse phase high-performance liquid chromatography (HPLC) analysis as described above for PCP and TeCH analysis, except that the absorptions at 285, 300, and 310 nm were recorded by using a Waters 490 E programmable multiwavelength UV detector. Gas chromatography/mass spectrometry (GC/MS) analysis was done as previously described (Topp and Akhtar, 1990).

I⁻ was measured by the Leuco crystal violet assay described above. $NO_2$ was colorimetrically measured using the N-(1-naphthyl) ethylenediamine dihydrochloride-sulfanilamide reagent method (American Public Health Association, 17th Ed., 1989). $NH_3$ was colorimetrically measured by Nesslerization method (American Public Health Association, 17th Ed., 1989). CN was measured by the colorimetric method of Nagashima (1984). $NH_2OH$ was measured by the method of Magee and Burris (1954). All the assays were proportionally reduced to 1 ml assay volume, and standards of all the tested chemicals were prepared in the enzyme assay mixture without the enzyme.

Results

Table 2 summarizes the chemicals tested as substrates for PcpB activity and the end product detected as a result of PcpB breakdown of these chemicals.

TABLE 2

Substrate Disappearance in the Presence of PcpB

| Substrates | (%) Relative Activity | End Products[a] |
|---|---|---|
| Pentachlorophenol | 100 | Tetrachloro-p-hydroquinone |
| Pentafluorophenol | 47 | N.I.[b] |
| 2,3,5,6-Tetrachlorophenol | 1212 | Tetrachloro-p-hydroquinone |
| 2,4,6-Triiodophenol | 172 | 2,6-Diiodo-p-hydroquinone |
| 2,4,6-Tribromophenol | 35 | 2,6-Dibromo-p-hydroquinone |
| Trichlorophenol | | |
| 2,4,6- | 29 | 2,6-Dichloro-p-hydroquinone |
| 2,3,6- | 302 | 2,3,6-Trichloro-p-hydroquinone |
| 2,3,4- | 29 | N.I.[b] |
| 3,4,5-[c] | 0 | None |
| 2,6-Dibromophenol | 605 | 2,6-Dibromo-p-hydroquinone |
| Dichlorophenol | | |
| 2,6 | 344 | 2,6-Chloro-p-hydroquinone |
| 2,3- | 24 | N.I.[b] |
| 3,5-[c] | 0 | None |
| 4-Amino-2,6-dichlorophenol | 93 | 2,6-Chloro-p-hydroquinone |
| 2,6-Dibromo-4-nitrophenol | 62 | 2,6-Dibromo-p-hydroquinone |
| 3,5-Diiodo-4-hydroxybenzonitrile | 835 | 2,6-Diiodo-p-hydroquinone |
| 3,5-Dibromo-4-hydroxybenzonitrile | 591 | 2,6-Dibromo-p-hydroquinone[d] |

[a] All enzyme reactions were conducted in a reaction mix volume of 100 µl, containing 10 nmoles of substrate, 40 nmoles of NADPH. The substrate depletion and product production were measured by HPLC or GC/MS analysis. Relative enzyme activity for PCP was assumed to be 100%; the relative enzyme activities for other compounds were compared with that for PCP.
[b] N.I., not identified; however, the formation of a reaction product was shown by HPLC.
[c] Except 3,4,5-trichlorophenol and 3,5-dichlorophenol, all the substrates listed in the table were completely oxidized by the enzyme. Monochlorophenol and phenol were not degraded by the enzyme.
[d] From Topp et al. (1992).

In all cases examined, PcpB converted the substituted phenol to the corresponding hydroquinone. PCP and 2,3,5,6-tetrachlorophenol were converted to a compound with the same HPLC retention time as that of TeCH (Xun and Orser, 1991c). TeCH was confirmed as the end-product by GC/MS (data not shown). PcpB oxidized 2,4,6-triiodophenol (TIP) to a product with a retention time of 7.75 min. by GC analysis and mass spectrum consistent with that expected for 2,6-diiodo-p-hydroquinone (DIHQ, molecular formula of $C_6H_4I_2O_2$). The base peak was at M/Z 362 (M+), and major fragments were found at M/Z 235 (loss of I from 362), 207 (loss of CO from 235), and 108 (loss of 2 I from 362). The end product of 3,5-diiodo- 4-hydroxylbenzonitrile was also identified as DIHQ because it shared the same retention time with DIHQ produced from TIP by HPLC analysis. Incubation of 2,3,6-trichlorophenol with PcpB yielded a product with a retention time of 4.65 min. by GC analysis and a mass spectrum consistent with that expected for 2,3,6-trichloro-p-hydroquinone (molecular formula of $C_6H_3Cl_3O_2$). The relative intensities of the peaks at M/Z 212 (base peak, M+), 214 (M+2), and 216 (M+4) are characteristic of a molecule containing 3 chlorine atoms, although the peak expected at M/Z 218 (M+6) was not observable. Major peaks were observed at M/Z 178 (loss of $H^{35}Cl$ from 214), M/Z 176 (loss of $H^{35}Cl$ from 212, $H^{37}Cl$ from 214), M/Z 150 (loss of CO from 178), and M/Z 148 (loss of CO from 1976).

Similarly, PcpB converted both 2,4,6-trichlorophenol and 2,6-dichlorophenol to compounds with the same HPLC retention time as authentic 2,6-dichloro-p-hydroquinone. 2,6-dibromophenol, 2,4,6-tribromophenol, 2,6-dibromo-4-nitrophenol, and 3,5 -dibromo-4-hydroxybenzonitrile were converted to end products sharing the same HPLC retention time. The end product from one of these compounds, 3,5-dibromo-4-hydroxybenzonitrile, was analyzed by GC/MS and confirmed to be 2,6-dibromo-p-hydroquinone (Topp et al., 1991).

Figure 9:
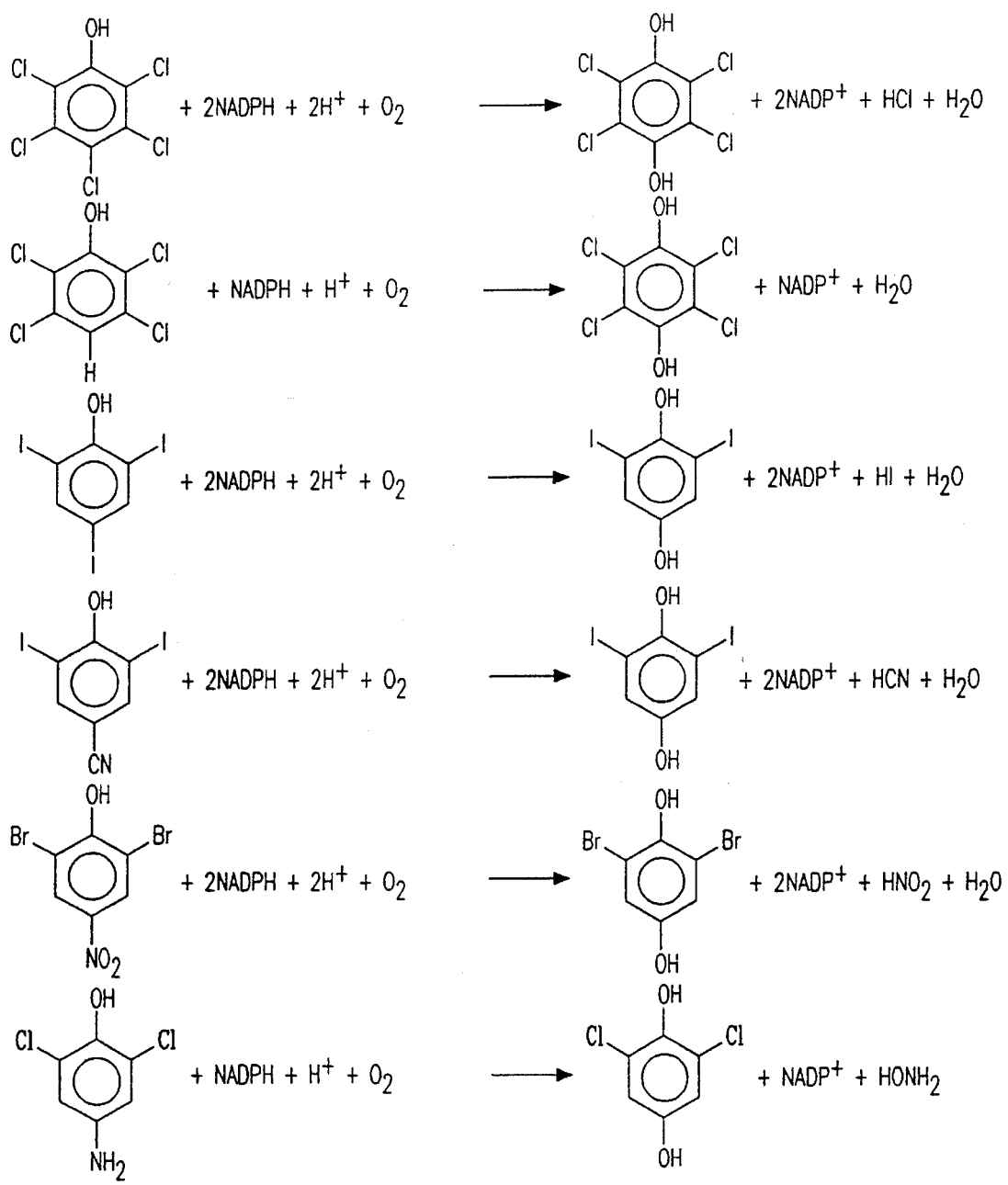
FIG. 9 shows structural formulas giving proposed reaction equations for representative substrates of PcpB.

PcpB quantitatively released an amino group as hydroxylamine (not as ammonium), a nitro group as nitrite, a cyano group as cyanide, and iodine as an iodide from the para position of substituted phenols tested. These results show that the enzyme not only catalyzes dehalogenation, but also removed hydrogen, nitro, amino, and cyano groups from benzene rings at the para position (in relation to the hydroxyl group of phenol). FIG. 9 shows proposed reaction equations for several representative substrates of PcpB.

Identification and Purification of PcpC

Identification of PcpC

As described above, the first step of PCP breakdown by Flavobacterium sp. Strain ATCC 39723 is an oxidation catalyzed by the enzyme PCP hydroxylase, also known as PcpB, which results in the formation of TECH. This reaction requires the presence of NADPH and oxygen. Whole cell studies with blocked mutants have been reported which propose that the Flavobacterium sp. reductively converts TeCH to 2,3,6-trichloro-p-hydroquinone (TrCH) and then to 2,6-dichloro-p-hydroquinone (DiCH), intermediates which are subsequently broken down by as yet uncharacterized reactions (Steiert and Crawford, 1986). The reductive dehalogenation of TeCH to TrCH and then to DiCH by a cell extract from ATCC 37923 has been confirmed by Xun et al. (1992b), herein incorporated by reference. A requirement for the reduced form of glutathione (GSH) as a reducing agent for this reaction was also demonstrated. GSH is a common cofactor among eucaryotic detoxication enzymes classified as glutathione S-transferases (GSTs) (Jokoby & Habig, 1980). This group of enzymes is capable of recognizing a wide spectrum of substrates, but the catalytic function is conserved.

The enzyme catalyzing the reductive dehalogenization of TeCH to DiCH is hereby termed tetrachloro-p-hydroquinone reductase or PcpC. This enzyme is alternatively referred to as tetrachloro-p-hydroquinone reductive dehalogenase. A method for purifying PcpC is described below.

Purification of PcpC

The enzymatic activity of PcpC was detected by the production of TrCH and DiCH from the substrate TeCH using high-pressure liquid chromatography (HPLC) analysis as described below. The purification scheme comprised seven major steps: cell extraction, streptomycin sulfate treatment, ammonium sulfate fractionation, phenyl agarose chromatography, DEAE agarose chromatography, mono Q chromatography, and gel filtration chromatography. The enzyme activity was followed using HPLC. Standard techniques were as described for PcpA purification unless otherwise stipulated.

Growth of cells. Flavobacterium sp. Strain ATCC 39723 was cultured and PCP degradation was induced as described above.

Enzymatic activity assay. The reaction mixture contained 50 mM KPi buffer (pH 7.4), 0.4% Tween 20 (Sigma), 100 µM of TeCH, and 1 mM ascorbic acid. All the reactions were incubated at 23° C. in an anaerobic chamber containing an atmosphere of 85% N2, 5% $CO_2$, and 10% $H_2$ (Coy Laboratory Products Inc., Ann Arbor, Mich.). The reactions were stopped by addition of an equal volume of acetonitrile to the reaction mixture. TeCH stock solution (20 mM) was prepared in absolute ethanol. NADPH and NADH stock solutions (10 mM) were freshly prepared in 1 mM Tris buffer (pH 13) with 1 mM dithiothreitol. The stock solutions of FAD 10 (10 mM), FMN (10 mM), and the reduced form of GSH (1M) were freshly prepared in distilled water before use.

Analytical method. DiCH was obtained from Aldrich Chemical Co. (Milwaukee, Wisconsin). TrCH was made by enzymatic hydroxylation of 2,3,6-trichlorophenol by PcpB. TeCH, TrCH and DiCH were analyzed by HPLC on a Nova-Pak C-18 column (3.9 by 150 mm) (Waters, Milford, Mass.) with an 11 mM $H_3PO_4$-acetonitrile gradient as described above. Maximum absorption at 285, 300, 310 nm was recorded by using a Waters 490E programmable multiwave-length UV detector connected to a Maxima NEC computer workstation (Waters). The retention times of TeCH, TrCH and DiCH were 8.9, 8.1 and 6.7 min., respectively. TeCH and DiCH in the reaction mixtures were identified and quantified by comparison of their retention time and peak areas with that of authentic standards, respectively. TrCH was extracted with diethyl ether from the reaction mixture and analyzed by gas chromatography/mass spectrometry (GC/MS) as described by Topp and Akhtar (1990). Since DiCH could not be extracted from the reaction mixture with ether, DiCH peak was collected from the HPLC analysis using 0.1% trifluoroacetic acid instead of $H_3PO_4$ in the elution gradient. The collected DiCH was dried in a Speed-vac (Savant Instruments Inc., Farmingdale, N.Y.) and resuspended in a few microliters of ethyl acetate before GC/MS analysis (Top and Akhtar, 1990). GSH and the oxidized form of glutathione (GS-SG) were detected by the enzymatic method of Tietze (1969).

Purification Steps

All operations were performed at 4° C., and all buffers contained 1 mM dithiothreitol. When ammonium sulfate was added, the buffer also contained 1 mM EDTA. Ammonium sulfate saturation levels referred to a temperature of 25° C.

(i) Extraction of Cells. Frozen (−20° C.) cell paste of 10 g was thawed in water and suspended in 50 ml of 20 mM Tris HCl buffer (pH 8.0) with 5 mM EDTA. The slurry was passed through an Aminco French pressure cell (model 4-3398) twice at 12,000 lb/in$^2$. The product was centrifuged at 17,000×g for 10 min., and the supernatant was saved. The precipitate was resuspended in 10 ml of the buffer, passed through a French pressure cell twice, and centrifuged as described above. The supernatant was combined with the previous supernatant, and the precipitate was discarded.

(ii) Streptomycin Sulfate Treatment. A half gram of streptomycin sulfate was added to the supernatant with constant stirring for 3 min. The mixture was centrifuged at 17,000×g for 10 min., and the precipitate was discarded.

(iii) Ammonium Sulfate Fractionation. The supernatant was diluted to 100 ml with the same Tris buffer, and solid ammonium sulfate was added to the supernatant to 30% saturation with constant stirring. The pH of the solution was not adjusted. After 10 min. of stirring, the mixture was centrifuged at 17,000×g for 10 min., and the precipitate was discarded. Additional solid ammonium sulfate was added to 65% saturation with constant stirring. After 10 min., the mixture was centrifuged at 17,000×g for 10 min. The precipitate was saved, and the supernatant was discarded.

(iv) Phenyl Agarose Chromatography. The precipitate was suspended with 1.5 volume of the Tris buffer. The suspension was centrifuged (17,000×g for 10 min.), and the precipitate was discarded. The supernatant was loaded onto a phenyl agarose (Sigma) column (30 by 1.5 cm), previously equilibrated with the Tris buffer containing 17% ammonium sulfate. The enzyme was eluted with 300 ml (linear gradient) of 17-1-0% ammonium sulfate. The enzyme activity was eluted out of the column from 14 to 12% ammonium sulfate. The fractions were pooled, and the proteins were precipitated by adding ammonium sulfate to 70% saturation. The precipitate was collected by centrifugation (17,000×g for 10 min.).

(v) DEAE Agarose Chromatography. The precipitate was suspended with an equal volume of 20 mM Tris buffer (pH 8.0) and dialyzed against 1 liter of the same buffer for 1 hr. The protein solution was loaded onto a DEAE agarose (Sigma) column (30 by 1.5 cm) previously equilibrated with the same buffer. The enzyme was eluted with 300 ml (linear gradient) of 0-to-300 mM NaCl in 20 mM Tris buffer (pH 8.0). The enzyme activity was eluted out of the column from 115 to 150 mM of NaCl. The fractions containing the enzyme activity were pooled, and the proteins were precipitated by adding ammonium sulfate to 70% saturation. The precipitate was collected by centrifugation (17,000×g for 10 min.).

Figure 10:
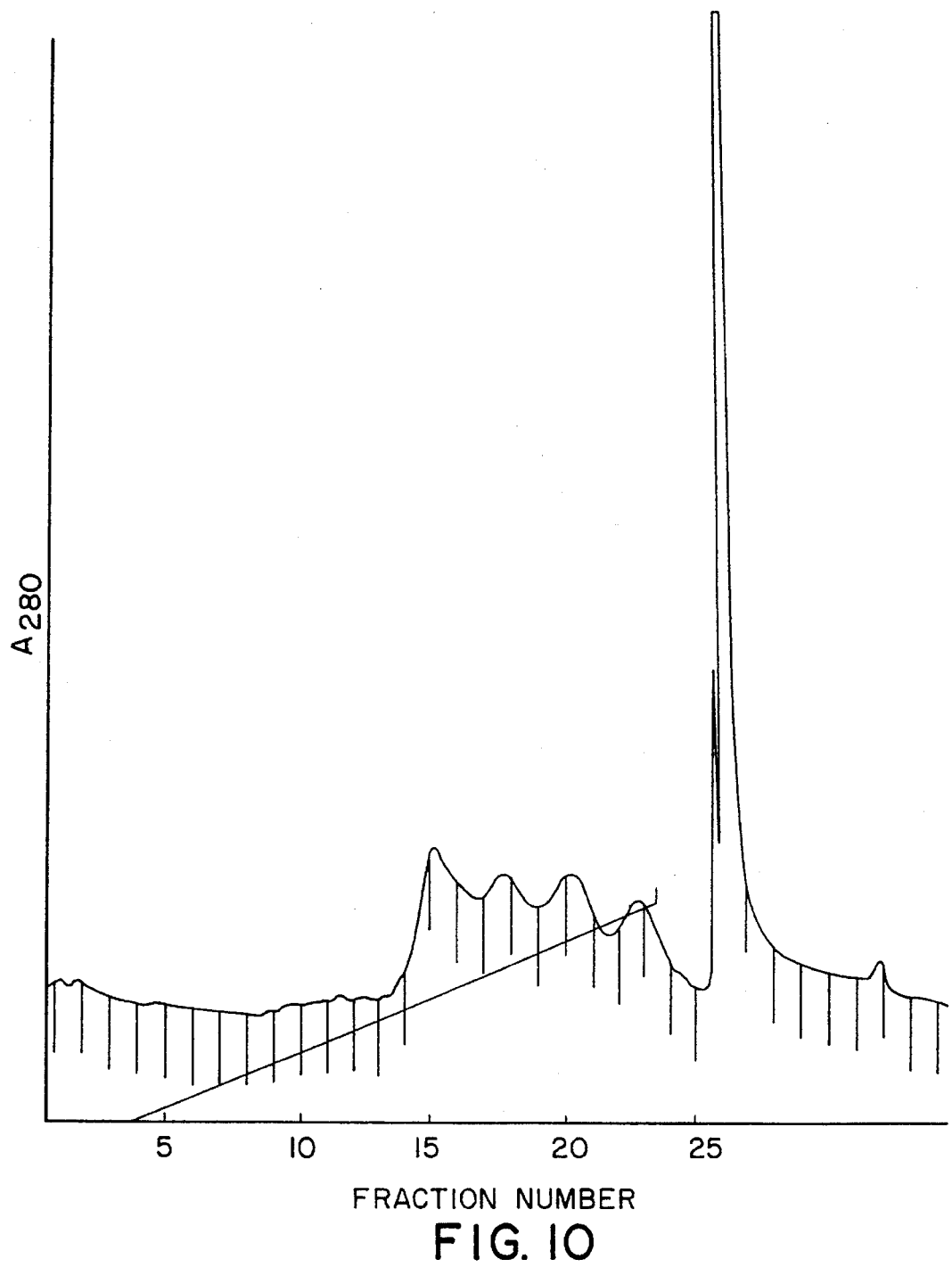
FIG. 10 is a graph showing the results of a Mono Q chromatography column utilized during purification of PcpC.

(vi) Mono Q Chromatography. The proteins were resuspended in 1 ml of 20 mM Tris buffer (ph 8.0) and dialyzed against 1 liter of the same buffer for 2 hr. The protein solution was injected onto a Mono Q HR 5/5 column (Pharmacia) equilibrated with 20 mM Tris buffer. Proteins were eluted with a linear gradient of sodium chloride (percentage of 1M NaCl in a volume of 20 mM Tris: 0%, 2 ml; 0–20%, 20 ml; 100%, 4 ml; 0%, 2 ml) by a Pharmacia Fast Protein Liquid Chromatography system (Pharmacia LKB Programmer GP-250 Plus and P-500 pump). A single PcpC activity peak was associated with a peak at NaCl concentration of approximately 120 mM corresponding to fractions 14, 15 and 16 as shown in FIG. 10. The fractions containing enzyme activity were pooled and precipitated by adding ammonium sulfate to 70% saturation. The precipitate was collected by centrifugation (17,000×g for 10 min.).

Figure 11:
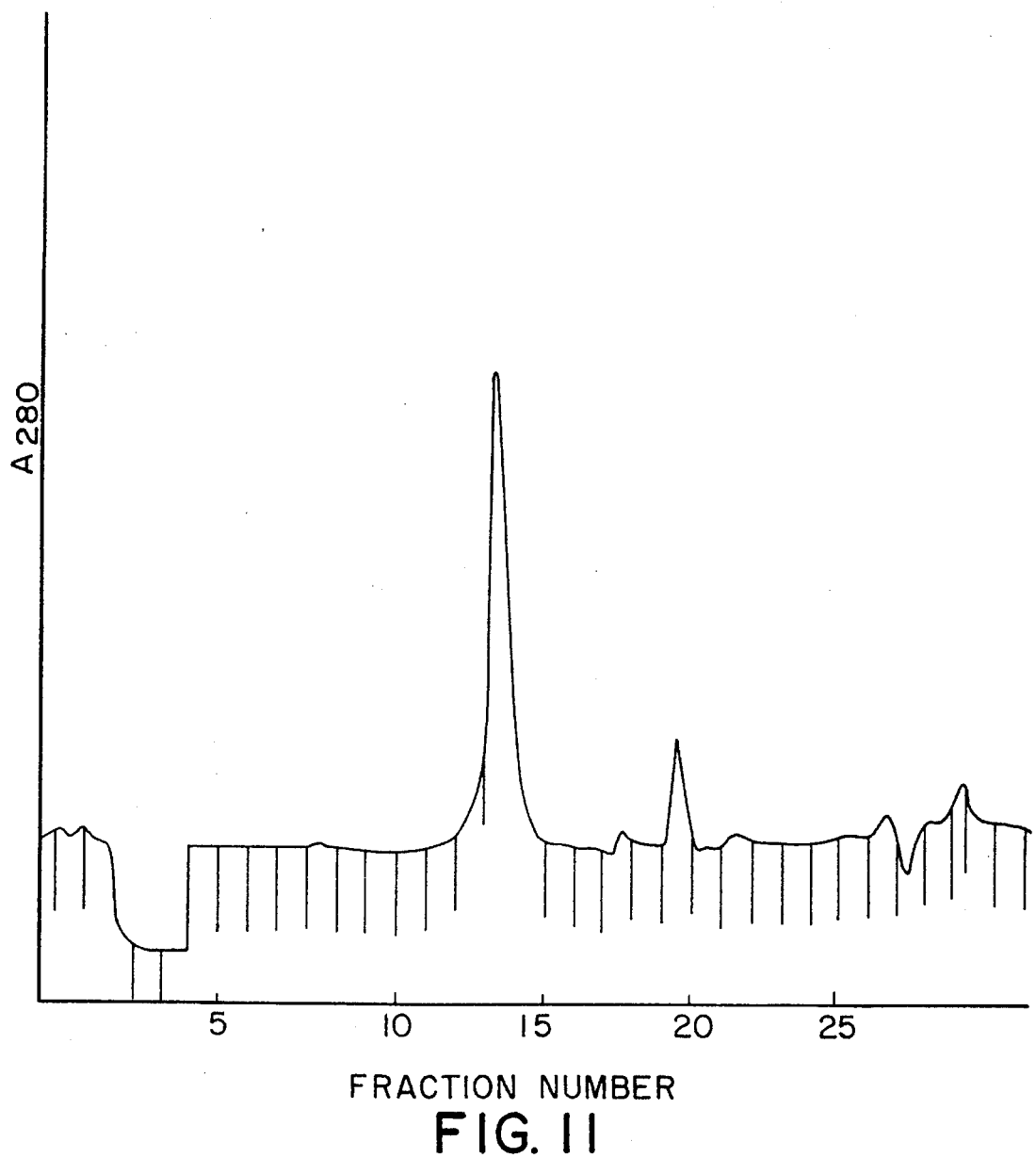
FIG. 11 is a graph showing the results of chromatography on an FPLC gel filtration column utilized during purification of PcpC.

(vii) Gel Filtration Chromatography. The protein precipitate was dissolved with an equal volume of Tris buffer and injected onto a Superose 12 column (Pharmacia) equilibrated with 20 mM Tris buffer containing 150 mM NaCl. The enzyme was eluted with the same buffer by the Pharmacia FPLC system. PcpC activity was primarily associated with a major protein peak with a retention volume of 13.5 ml, corresponding to fraction 14 shown in FIG. 11. The fractions containing the enzyme activity were pooled and precipitated by adding ammonium sulfate to 70% saturation. The precipitate was collected by centrifugation (17,000×g for 10 min.). The enzyme was resuspended in equal volume of 20 mM Tris buffer (ph 8.0) and stored at –20° C.

Figure 12:
FIG. 12 is an SDS-PAGE gel of purified PcpC.

FIG. 12 shows SDS-PAGE of the products of the final two steps in PcpC purification: lane 1, fraction 15 from the gel filtration column of (vii) above; lane 2, molecular weight size markers (66, 45, 34, 24, 18.4, 14.3 kDa. from top to bottom); lane 3, fraction 14 from the gel filtration column of (vii) above; lane 4, empty; lane 5, molecular weight size markers as lane 2; lane 6, combined fractions 14, 15, and 16 from the Mono Q column of (vi) above. On the basis of this SDS-PAGE, the final purified PcpC preparation comprises a single band of approximately 26–29 kDa. (i.e., a molecular weight of 26,000–29,000).

Characterization of PcpC Activity upon the addition of TeCH reductive dehalogenase (33 µg of purified enzyme per ml) to the reaction mixture, TeCH was converted to two compounds, which were eluted from the HPLC column at 6.8 and 7.1 min (data not shown). The compound eluting at 7.1 min was extracted with anhydrous ether and confirmed to be DiCH by gas chromatography-mass spectroscopy analysis (spectrum now shown), while the compound eluting at 6.8 min was not extractable with ether but was subsequently shown to contain $^3$H peaks in the GSH labeling experiment.

Using GSH as a limiting factor, the conversion of TeCH to TrCh, DiCH, monochloro-p-hydroquinone (MonoCH), and several intermediates was identified.

The purified enzyme solution was colorless and showed a typical protein absorption peak at about 280 nm. The enzyme was quite stable in solution at a concentration of greater than 0.5 mg/ml at –20° C. There was no measurable loss of activity over a period of 1 month. However, the enzyme seems to be sensitive to oxygen, because a loss of enzyme activity occurred when DTT was not included in elution buffers during purification. The optimal conditions for TeCH reductive dehalogenase are as follows: pH 6.0 to 7.0, 40° C., and about 100 µM total salts.

Gene Cloning

The purification of proteins PcpA, PcpB and PcpC as described above facilitated the cloning of the genes encoding these three enzymes. The genes encoding the proteins PcpA, PcpB and PcpC are designated pcpA, pcpB and pcpC, respectively. The N-terminal amino acid sequence of each of the purified enzymes was determined on an Applied Biosystems Automated Protein Sequenator (Applied Biosystems, Foster City, Calif.). Based on these N-terminal amino acid sequences, degenerate oligonucleotide probes were synthesized on an Applied Biosystems DNA synthesizer and employed in the schemes described below in order to clone the genes encoding these three proteins.

Cloning of the Gene Encoding PcpA

The N-terminal sequence (residues 1 to 23) of the purified protein PcpA was determined to be Met-Glu-Thr-Asn-His-Ile-Thr-Ser-Leu-His-His-Ile-Thr-Ile-Cys-Thr-Gly-Thr-Ala-Gln-Gly-Asp-Ile. This amino acid sequence is part of SEQ. ID No. 1 in the accompanying sequence listing.

Two degenerate oligonucleotide primers, LX-1B and LX-2B, were made corresponding to amino acid residues 1 to 7 [5'-AUGGA(A/G)AC(T/C/A/G)AA(T/C)CA(T/C)AT(T/C/A)AC-3'] and 23 to 19 [5'-(A/G/T)AT(A/G)TC(T/G/A/C)CC(T/C)TG(A/G/T/C)GC-3'], respectively. Primers LX-1B and LX-2B are set forth in SEQ. ID Nos. 7 and 8, respectively, in the accompanying sequence listing. The primers were made in opposing orientations so as to amplify the internal region in a polymerase chain reaction (PCR). The PCR reactions were performed using conventional techniques (Mullis and Faloona, 1987; Innis et al., 1990) and the thermostable DNA polymerase from *Thermus aquaticus* DNA Taq polymerase (Saiki et al., 1988).

PCR was performed in a Coy temperature cycler (Coy Laboratory Products, Inc., Ann Arbor, Mich.) with a temperature profile of 94°–55°–72° C. cycling for 30 sec, 1 min., and 1 min., respectively, for 35 cycles. A 68 bp fragment was amplified by PCR, labeled with [α-$^{32}$P] dCTP by random priming (Sambrook et al., 1989) and used as a probe in genomic DNA and colony hybridizations. Southern hybridization (Southern, 1975) revealed that a single 21 kb BamHI fragment of Flavobacterium sp. Strain ATCC 39723 genomic DNA hybridized with the probe.

A genomic library of ATCC 39723 was subsequently constructed as described by Xun and Orser (1991a). Total DNA was extracted from ATCC 39723 by the method of Birboim and Doly (1979) and purified through two cycles of cesium chloride-ethidium bromide density gradient centrifugation (Sambrook et al., 1989). DNA extracted in this manner was partially digested with BamHI and size fractionated to select for 18 to 25 kb fragments (Sambrook et al., 1989). The cosmid vector pLAFR3 was prepared as described by Staskawicz (1987) and BamHI pLAFR3 arms were ligated to ATCC 39723 BamHI-digested DNA fragments. Ligated molecules were packaged in vitro with freeze-thaw and sonication extracts of bacteriophage lambda, prepared after heat induction of lysogen strains BHB 2688 and BHB 2690 according to Maniatis et al. (1982). Packaged molecules were transduced into *E. coli* HB101 as described by Maniatis et al. (1982). Transductants were selected on Luria agar plates supplemented with streptomycin and tetracycline. Hybridization was performed using the 68 bp fragment labeled with [$\alpha$-$^{32}$P] dCTP by random priming as described by Sambrook et al. (1989). Several positive colonies were detected by hybridization with the 68 bp probe. One positive colony was selected, and this cosmid, containing pcpA, the gene encoding the protein PcpA, was designated pLX001. The cloned DNA was analyzed by different restriction enzymes in a Southern hybridization with the amplified DNA probe. A 5.5 kb EcoRI fragment, which hybridized to the 68 bp probe, was subcloned into pBluescript KS$^+$ phagemid (pBS-KS$^+$) (Stratagene, San Diego, Calif.), to create pLX101$^+$ and then cloned into pBluescript KS$^-$ (pBS-KS$^-$) (Stratagene, San Diego, Calif.) in the same orientation, to create pLX101$^-$. An internal AccI fragment within the 5.5 kb EcoRI fragment was deleted by AccI digestion followed by religation. Subsequently, a 2.4 kb EcoRI-AccI fragment which hybridized to the 68 bp probe and contained pcpA was cloned into pBS-KS$^+$ to produce pLX201$^+$, and this fragment was also cloned into pBS-KS$^-$ to produce pLX201$^-$.

Nucleotide Sequence of pcpA

DNA sequencing was performed by the dideoxy-chain termination method of Sanger et al. (1977), using [$\alpha$-$^{35}$S] dATP and the M13 universal or reverse primer (Messing et al., 1981). Single-stranded DNA templates were recovered from pBluescript phagemid subclones by using helper phage as recommended by the vendor (Stratagene, La Jolla, Calif.). Nesting deletions were generated from both ends of the 2.4 kb EcoRI-AccI fragment by the procedures of Henikoff (1987), using mung bean nuclease and exonuclease III.

The management of compiled sequence data and DNA sequence analysis were done by using the IBI Pustell sequence analysis software (International Biotechnology Inc., New Haven, Conn.). Comparisons of nucleotide sequences and translated sequences were performed by using PC Gene software, version 6.1 (Intelligenetics, Mountain View, Calif.).

The 2.4 kb EcoRI-AccI fragment has been sequenced in both orientations. The pcpA sequence is presented as Sequence ID No. 1 in the Sequence Listing which forms part of this document. The open reading frame of the pcpA gene is 816 nucleotides in length from the GTG initiation codon (at base pairs 194–196 as shown in Sequence ID No. 1) to the TGA termination codon (at base pairs 1007–1010 as shown in Sequence ID No. 1).

The nucleotide sequence matched the N-terminal amino acid sequence perfectly. FIG. 13 shows the 20 N-terminal amino acids of PcpA. The sequence of these amino acids was determined by protein sequencing and confirmed by theoretical translation of the nucleotide sequence of pcpA. The predicted translation product of pcpA was 271 amino acids in length with a predicted molecular weight of 30,000, which is in good agreement with the protein purification data for PcpA. The computer-predicted translation product was hydrophilic with an isoelectric point of 5.75. A database search of the pcpA sequence has revealed no extensive sequence similarity with any characterized genes, although pcpA shared 53% homology with several mammalian cytochrome P450-type monooxygenases (Ishida et al., 1988) and the *Pseudomonas putida* catechol dioxygenase gene (Frantz and Chakrabarty, 1987). Protein database searches did not produce any significant results with these or other translated genes.

Cloning of the Gene Encoding PcpB

The N-terminal sequence (residues 1 to 13) of the purified protein PcpB were determined to be Ser-Thr-Tyr-Pro-Ile-Asn-Ala-Pro-Gly-Gln-Ser-Ala-Asp. This amino acid sequence is encompassed in SEQ. ID. No. 5 in the accompanying sequence listing. From the N-terminal sequence, a 37 mer degenerate primer was designed, corresponding to amino acid residues 2 to 13, for use as a hybridization probe for identification of the corresponding gene, pcpB. The primer was designated LX-6 and had the following 5' to 3' sequence: AC(C/G)TA(T/C)CC(C/G)AT(C/T)AA(T/C)GC(G/C)CC (C/G)GG(G/C)CA(G/A)(A/T)(G/C)(C/G)GC(G/C)GA(C/T)I, where I is inosine. The sequence of primer LX-6 is set forth in SEQ. ID. No. 9 ' of the accompanying sequence listing. DNA-DNA hybridization by Southern blot analysis (Southern, 1975) using [$^{32}$P]-randomly labeled primer LX-6 against EcoRI digested total genomic DNA from ATCC 39723, revealed a single 3.0 kb fragment. Hybridization was performed in 6×SSC solution (0.9M NaCl) (Sambrook et al., 1989) at 65° C., with subsequent washing of the filters under the same conditions. These conditions equate to a theoretical stringency of approximately 94% according to the formulae and calculations presented in Sambrook et al., (1989); that is, hybridization would only occur between molecules with sequence mismatches totaling no more than 6%. It should be noted that this is a theoretical calculation only (Sambrook et al. 1989). The LX-6 hybridizing fragment was cloned by electroelution of DNA from a gel fragment (Sambrook et al., 1989) which spanned the 3.0 kb region, followed by ligation to EcoRI digested pBluescript KS$^+$ vector DNA, which encodes ampicillin resistance. Amp$^R$ *E. coli* transformants containing the specific fragment were identified by colony hybridizations. One such positive clone was designated CO221, and its corresponding hybrid construct was designated pCO221.

Nucleotide Sequence of pcpB

The 3.0 kb EcoRI fragment was sequenced by the methods described above for pcpA, and a major open reading frame representing the pcpB gene was identified. The DNA sequence of pcpB is presented in Sequence ID No. 2 in the Sequence Listing which forms part of this document. The open reading frame of the pcpB gene is 1617 nucleotides in length from the ATG initiation codon (at base pairs 328–330 as shown in Sequence ID No. 2) to the TGA termination codon (at base pairs 1942–1944 as shown in Sequence ID No. 2). The nucleotide sequence of this open reading frame matched the N-terminal amino acid sequence of the purified PcpB protein with the exception of the N-terminal methionine which was absent from the protein sequence determined by amino acid sequencing. This may indicate that this methionine is cleaved from the mature form of the protein. The predicted translation product of pcpB is 538 amino acids in length with a predicted molecular weight of approximately 59,900. The discrepancy between this molecular weight, the molecular weight of 63,000 as estimated by SDS-PAGE and the molecular weight of 66,000 determined by gel filtration chromatography reflects the diversity of experimental methods utilized to estimate the true molecular weight. PcpB is therefore a protein with a molecular weight in the range 59,000–63,000. FIG. 13 shows the 20 N-terminal amino acids of PcpB. Amino acids 1–13 were determined by protein sequencing and confirmed by theoretical translation of the nucleotide sequence of pcpB. Amino acids 14–20 were determined by theoretical translation of the pcpB nucleotide sequence.

Sequence analysis and molecular modelling of PcpB was performed using the Washington State University FAX cluster. Database searches were performed by pairwise comparison using the Basic Local Alignment Search Tool (BLAST) (Altschul et al., 1990) and the sequence databases at the National Center of Biotechnology Information (NCBI). A nonredundant search of the NCBI databases using the deduced amino acid sequence of PcpB as a query sequence suggested some similarity with flavoprotein monooxygenases of bacterial origin involved in phenolic compound metabolism. Sequence alignment indicated two conserved domains predicted to be involved with binding the flavin adenine dinucleotide (FAD) molecule.

Cloning of the Gene Encoding PcpC

The N-terminal sequence (residues 1 to 18) of the purified protein PcpC were determined to be Pro-Glu-Val-Ser-Leu-Tyr-Asn-Tyr-Thr-Met-Ser-Ile-xxx-Ser-Met-Lys-Thr-Arg. -xxx- represents an amino acid which was unidentifiable by this protein sequencing. This amino acid sequence is set forth in SEQ. ID. No. 10 in the accompanying sequence listing. From the N-terminal sequence a 36 mer degenerate primer was designed, corresponding to amino acid residues 1 to 12, as a hybridization probe for identification of the corresponding gene, pcpC. The primer, LX-7, was designed to be the complement to the mRNA so that it could be used for identifying the pcpC gene and mapping the transcriptional start site. The 5' to 3' sequence of LX-7 is as follows: GAT(C/G)(C/G)(T/A)CAT(G/C)GT(A/G)TAGTT(A/G)TA(C/G)AG(C/G)(C/G)(T/A)(G/C)AC(T/C)TC(G/C)GG. The sequence of primer LX7 is set forth in SEQ. ID. No. 11 in the accompanying sequence listing.

LX-7 was labeled by random priming with [$\alpha$-$^{32}$P] dCTP and used to probe EcoRI-digested genomic DNA from ATCC 39723. A 0.7 kb EcoRI fragment hybridized. This fragment was cloned as described above for pcpB in the vector pBluescript KS+, and the resulting recombinant replicon was designated pC0301. It was subsequently confirmed that this fragment is also contained in the cosmid clone, pLX001, which was originally identified as containing pcpA. Therefore, pcpA and pcpC reside in close proximity to each other on the Flavobacterium genome.

The 0.7 kb EcoRI fragment was partially sequenced and determined to contain only 100 bp of the coding sequence for pcpC. Therefore, the 0.7 kb fragment was subsequently used in Southern hybridizations as a probe to clone a 4.0 kb EcoRV-PstI fragment in the vector pBluescript SK+; this construct was designated pC0248. The same 4.0 kb fragment was also cloned into the vector pBluescript SK- to yield pC0249.

Nucleotide Sequence of pcpC

The sequence of the pcpC gene is presented as Sequence ID No. 3 in the Sequence Listing which forms part of this document. The open reading frame of the pcpC gene is 753 nucleotides in length from the ATG initiation codon (at base pairs 388–390 as shown in Sequence ID No. 3) to the TGA termination codon (at base pairs 1138–1140 as shown in Sequence ID No. 3). The predicted translation product of pcpC is 250 amino acids in length with a predicted molecular weight of approximately 28,500. The 5' nucleotide sequence obtained matches the N-terminal amino acid sequence with the exception of the N-terminal methionine which was not detected by protein sequencing. A similar observation was reported for PcpB, as discussed above. The single amino acid which was unidentifiable by protein sequencing is now shown to be a cysteine by a theoretical translation of the obtained DNA sequence. FIG. 13 shows the 20 N-terminal amino acids of PcpC. Amino acids 1–12 and 14–18 were determined by protein sequencing and confirmed by theoretical translation of the pcpC nucleotide sequence. Amino acids 13, 19 and 20 were determined by theoretical translation of the pcpC nucleotide sequence.

Cloning of the Gene Encoding PcpD

Figure 14:
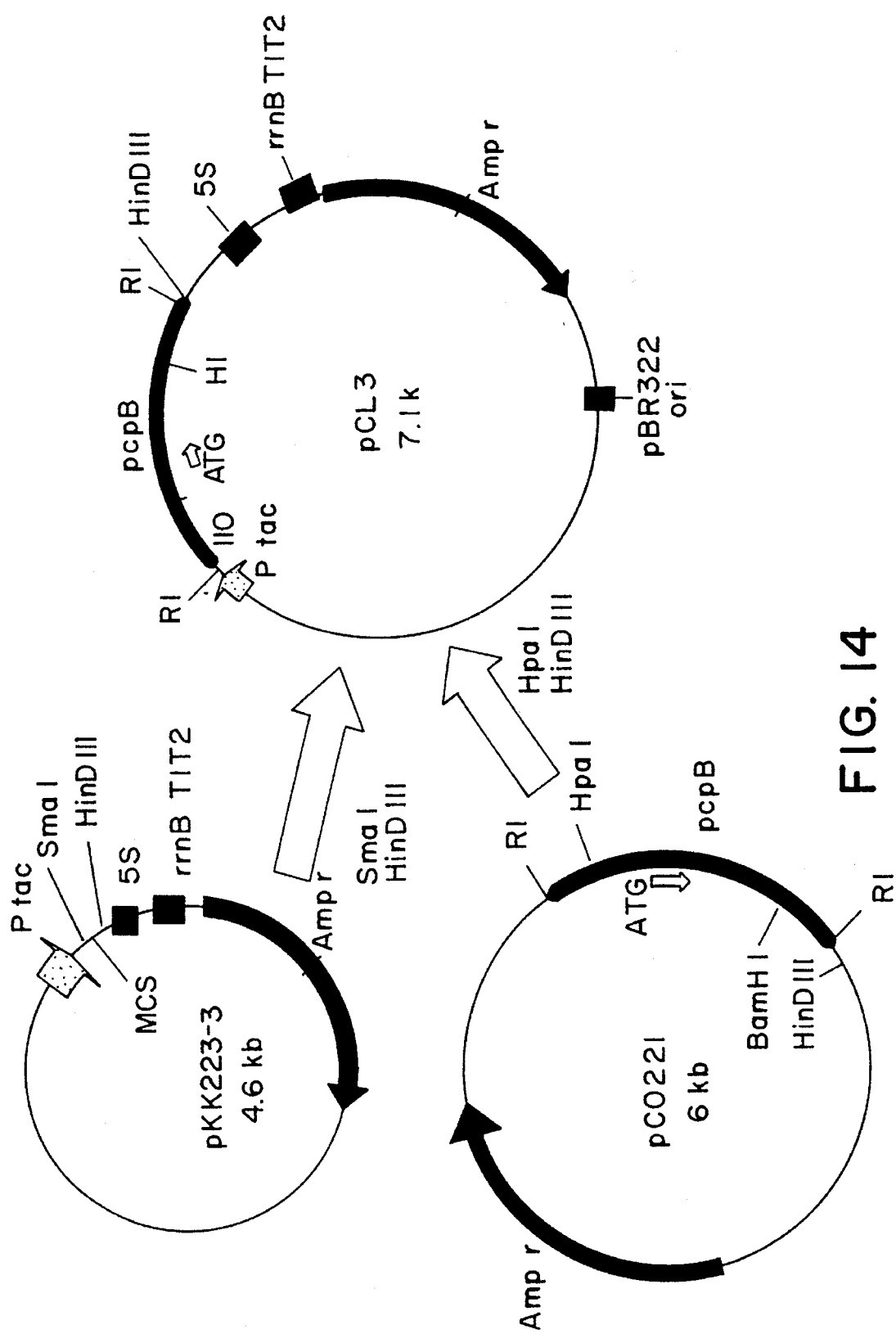
FIG. 14 shows the construction of pCL3, a plasmid vector which expresses the PcpB protein.

Sequence analysis of pCO221, a plasmid containing the pcpB gene as shown in FIG. 14, revealed the presence of an open reading frame (ORF) immediately downstream from pcpB. Sequence analysis of the ORF was performed using the University of Wisconsin Genetic Computer Group Sequence Analysis Package, Version 8.0 at the Visualization and Design in the Molecular Sciences laboratory at Washington State University, Pullman, Wash. Sequences for the analysis were obtained from the National Center for Biotechnology Information. Database searches using the Basic Local Alignment Search Tool (BLAST) revealed that the ORF had similarity to the N-terminal regions of several reductase components of two-component oxygenases of bacterial origin. This open reading frame was termed pcpD. The ATG start site for the ORF was 13 base pairs downstream from the stop codon of the pcpB gene and was preceded by a typical *E. coli* ribosome binding site (GAGG) which overlapped the TGA stop codon of pcpB. Because the DNA coding for the C-terminus of PcpD was found to be absent from pC0221, the 0.5 kbp BamHI to EcoRI fragment from pCO221, coding for an internal region of PcpD, was used to make a $\alpha$-$^{32}$P-dCTP labelled probe for Southern hybridization against BamHI digested Flavobacterium genomic DNA. This probe hybridized with a 2.2 kb BamHI fragment. Approximately 20 µg of Flavobacterium genomic DNA was then digested with BamHI and electrophoresed on a 1% agarose gel. The resulting 2.0 to 2.5 kbp fragments were excised and eluted from the gel and ligated into BamHI digested, alkaline phosphatased pBluescript II DNA, and then electroporated into *E. coli* JM105. Clones containing the hybridizing fragment were identified by colony hybridization using the same probe as described above. One of the positive colonies was picked and designated CCLS. The ampicillin resistant plasmid was designated pCLS.

Sequencing of pCL8 resulted in the determination of the sequence of the C-terminal portion of pcpD, which contained the coding region for a well conserved ferredoxin domain. The sequence of pcpD with its translation product is presented in SEQ. I.D. No. 12 in the accompanying sequence listing. The pcpD gene was found to code for a predicted 323 amino acid polypeptide (molecular weight of 35,942 daltons). Based on multiple sequence alignments, PcpD belongs to the family of class 1 dioxygenase electron transport proteins (Mason and Cammack, 1992) which includes the phenoxybenozoate dioxygenase reductase, PobB, from *Pseudomonas pseudoalcaligenes* (unpublished); the vanillate demethylast/monooxygenase reductase, VanB, from Pseudomonas sp. strain ATCC 19151 (Brunel and Davison, 1988) and phthalate dioxygenase reductase, Pht2, from *Pseudomonas cepacia* (Correll et al., 1992).

From the multiple sequence alignment, three structural domains within PcpD were predicted, one involved in binding flavin mononucleotide (FMN), the second responsible for binding reduced nicotinamide adenine dinucleotide cofactor (NADPH), and the third forming a plant-ferredoxin-type (2Fe-2S) center. These predictions were based on the known X-ray crystal structure determined for Pht2 (Correll et al., 1992) in comparison with a motif library available through the GCG program. Based on these observations, PcpD should be classified as an iron sulfur flavoprotein-oxidoreductase. PcpD has been designated as the PCP 4-monooxygenase reductase based on the observation that pcpB and pcpD are transcribed together as a dicistronic message when induced with PCP, as determined by Northern blot analysis of Flavobacterium PCP induced and uninduced messenger RNAs.

Cloning of the Gene Encoding PcpR

Sequence determination of the 2.2 kbp fragment of pCL8 revealed the presence of a second ORF downstream of pcpD, which is herein designated pcpR. The coding region for the C-terminus of PcpR was determined to be absent from pCLS. To recover the entire ORF, the plasmid pCL8 was digested with EcoRI and BamHI to release the 1.7 kbp fragment, containing pcpR sequence, which was then used to make a probe for hybridization with EcoRI digested Flavobacterium DNA. The probe hybridized to a 3.2 kbp fragment which was subsequently cloned into pBluescript II DNA in *E. coli* JM105 in the same manner described above, and a positive colony picked and designated CCL12. The plasmid PCL12 was also subcloned to produce the plasmid pCL16 by removing the 1.2 kbp SacII to EcoRV fragment, containing the whole pcpR structural gene, and blunt ending with T4-polymerase in the presence of excess nucleotide triphosphates. The blunt end fragment was then ligated to EcoRV cut, alkaline phosphatase treated pBluescript II vector DNA, and positive clones containing inserts were identified by blue/white selection, for interruption of lacZ, on LB plus X-gal and isopropyl-β -D-thiogalactopyranoside (IPTG), and the gene orientation determined by sequencing ssDNA using the reverse primer. The gene, pcpR, was determined to be oriented in pCL16 such that it would be transcribed in the same direction as lacZ on pBluescript II.

The pcpR ORF coded for a predicted 303 amino acid polypeptide (Mr=33,549 Da), which possessed a helix-turn-helix (H-T-H) DNA-binding motif in its N-terminal region. The sequence of pcpR with its translation product is set forth as SEQ I.D. No. 13 in the accompanying sequence listing.

Analysis of the Role of PcpR in PCP Degradation

To confirm that PcpR may be involved in PCP degradation, an internal region of the pcpR structural gene was amplified from pCL16 by polymerase chain reaction, and this amplified fragment was used to make a radiolabelled probe. The probe was used for Southern analysis of EcoRI digested genomic DNAs from other PCP-degrading microorganisms shown to possess pcpB hybridizing DNA, as well as pcpA, pcpC and pcpD hybridizing DNA (see Example 8 below). The PCP-degrading bacteria analyzed were Arthrobacter sp. strain ATCC 33790 (Stanlake and Finn, 1982), Pseudomonas sp. strain SR3 (Resnick and Chapman, 1994), Sphingomonas sp. strain RA2 (Radehaus and Schmidt, 1992), and Flavobacterium sp. strain ATCC 39723 (Saber and Crawford, 1985) as a positive control. All of the PCP-degraders hybridized with the pcpR probe, and all hybridizing bands were approximately 3.2 kbp in size. *E. coli* genomic DNA, the negative control, did not hybridize with the pcpR probe.

To confirm the direct involvement of PcpR with PCP degradation in the Flavobacterium sp. the pcpR gene on the plasmid pCL16 was interrupted at a unique Eco47III site by insertion of the nptII gene, conferring kanamycin resistance, and this interrupted construct was then used to transform Flavobacterium sp. strain ATCC 39723 by electroporation. Since pBluescript II DNA does not replicate in the Flavobacterium sp. (Schneider et al., 1994), kanamycin resistant Flavobacterium that arise represent clones in which a copy of the construct was integrated into the chromosome. Southern analysis of Flavobacterium recombinants, using the pcpR gene probe and an nptII probe showed the presence of numerous cointegrate strains containing one good copy of pcpR and one interrupted copy, pcpR::nptII, and the presence of two resolved strains that retained only one interrupted copy of pcpR. These resolved pcpR::nptII mutant strains were used for further analysis. Northern blot analysis of the pcpR::nptII mutants and the wild type Flavobacterium sp. total RNAs showed that addition of PCP to wild type culture induced pcpBD and pcpA transcription as previously reported (Orser, et al., 1993; Xun and Orser, 1991), whereas no transcript for pcpBD or pcpA could be detected in the pcpR::nptII mutants after addition of PCP to the cultures. This was further confirmed by analyzing the PCP-degrading capabilities of cultures. As expected, the wild type Flavobacterium sp. degraded PCP, where as the pcpR::nptII mutants were severely altered in their ability to degrade PCP. This evidence supports the hypothesis that the role of PcpR is to activate transcription of pcpBD and pcpA.

Discussion

Having herein presented purified preparations of PcpA, PcpB and PcpC and cloned DNA molecules which encode these proteins, and the DNA sequences of pcpD and pcpR, proteins and DNA molecules which possess the biological characteristics of the specific proteins and DNA molecules presented are also comprehended by this application.

It will be appreciated by one skilled in the art that this invention, by providing cloned DNA molecules and nucleotide sequences, facilitates the synthesis of many variations on the disclosed DNA molecules and nucleotide sequences, through the use of standard molecular biology laboratory techniques. Such variant DNA molecules include those created by standard DNA mutagenesis techniques, for example, M13 primer mutagenesis, details of these techniques are provided in Sambrook et al. (1989). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still maintaining the essential characteristics of the encoded protein are comprehended by this invention. Also within the scope of this invention are small DNA molecules which are fragments of the disclosed DNA molecules. Such fragments of the disclosed DNA molecules include oligonucleotides suitable for use as hybridizations probes or polymerase chain reaction (PCR) primers. These fragments are preferably greater than 15 nucleotides in length when selected for use as hybridization probes or PCR primers. Most preferably they are greater than 20 nucleotides in length and most preferably they are greater than-25 nucleotides in length.

DNA molecules and nucleotide sequences which are derived from the disclosed DNA molecules as described above may also be defined as DNA sequences which hybridize under stringent conditions to the DNA sequences disclosed, or fragments thereof.

Hybridization conditions resulting in particular degrees of stringency will vary depending upon the nature of the hybridizing DNA used. Calculations regarding hybridization conditions required for attaining particular degrees of stringency are discussed by Sambrook et al. (1989), chapters 9 and 11, herein incorporated by reference. The stringency of hybridization conditions is determined by the nature of the DNA molecules involved (factors such as length and GC content are important), the ionic conditions of the medium and the temperature of the hybridization reaction.

In preferred embodiments of the present invention, stringent conditions may be defined as those under which DNA molecules with more than 25% sequence variation (also termed "mismatch") will not hybridize. Such conditions are referred to herein as conditions of 75% stringency (since hybridization will occur only between molecules with 75% homology or greater). In a more preferred embodiment, stringent conditions are those under which DNA molecules with more than 15% mismatch will not hybridize (conditions of 85% stringency), and more preferably still, stringent conditions are those under which DNA sequences with more than 10% mismatch will not hybridize (conditions of 90% stringency). In a most preferred embodiment, stringent conditions are those under which DNA sequences with more than 6% mismatch will not hybridize (conditions of 94% stringency). Hybridizations under stringent conditions could be carried out under the hybridization conditions described herein with respect to the initial isolation of the pcpA, pcpB and pcpC genes and in Example 8.

DNA sequences which, but for the degeneracy of the genetic code, would hybridize to disclosed DNA molecules, and oligonucleotide sequences are also comprehended by this invention. The degeneracy of the genetic code further widens the scope of the present invention as it enables major variations in the nucleotide sequence of a DNA molecule while maintaining the amino acid sequence of the encoded protein. For example, the second amino acid residue of the PcpB protein is serine. This is encoded in the pcpB gene by the nucleotide codon triplet TCG. Because of the degeneracy of the genetic code, five other nucleotide codon triplets—TCT, TCC, TCA, AGT and AGC—also code for serine. Thus, the nucleotide sequence of the pcpB DNA could be changed at this position to any of these five codons without affecting the amino acid composition of the encoded protein or the characteristics of the protein. The genetic code and variations in nucleotide codons for particular amino acids is presented in Tables 3 and 4. Based upon the degeneracy of the genetic code, variant DNA molecules may be derived from the DNA molecules disclosed herein using standard DNA mutagenesis techniques as described above, or by synthesis of DNA sequences. DNA sequences which do not hybridize under stringent conditions to the DNA sequences disclosed by virtue of sequence variation based on the degeneracy of the genetic code are herein also comprehended by this invention.

TABLE 3

The Genetic Code

| First Position (5' end) | Second Position | | | | Third Position (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop (amb)" for the amber. ATG is the most common initiator codon; GTG usually codes for valine, but it can also code for methionine to initiate an mRNA chain.

TABLE 4

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

One skilled in the art will recognize that the mutagenesis protocols described above will also facilitate the production of proteins which differ in certain structural aspects from either PcpA, PcpB or PcpC, yet which proteins are clearly derivatives of these named proteins and which maintain the essential characteristics of the parent protein. Newly derived proteins may also be selected in order to obtain variations on the characteristics of the parent protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known, for example, M13 primer mutagenesis.

Amino acid substitutions are typically of single residues; insertions usually will be on the order of about from 1 to 10 amino acid residues; and deletions will range about from 1 to 30 residues. Substitutions, deletions, insertions or any combination thereof may be combined to arrive at a final construct. Obviously, the mutations that will be made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are made in accordance with the following Table 5 when it is desired to finely modulate the characteristics of the protein.

TABLE 5

| Original Residue | Exemplary Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |

TABLE 5-continued

| Original Residue | Exemplary Substitutions |
| --- | --- |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 5, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of PcpB and PcpC by analyzing the enzymatic characteristics of the derivative proteins using the enzyme assays for PcpB and PcpC disclosed herein.

The purified enzymes and the DNA molecules encoding the enzymes presented herein may be utilized in aspects of both the study and practical application of microbial catabolism of PCPs and other halogenated and otherwise substituted aromatics.

Utilities of the present invention include, but are not limited to, those utilities described in the following examples.

Those skilled in the art will recognize that the utilities herein described are not limited to the specific experimental modes and materials presented and will appreciate the wider potential utility of this invention.

EXAMPLE 1

Purified proteins PcpB and PcpC may be used for the in vitro dechlorination of PCP. Both of these proteins remove chlorine atoms from their substrate molecule, thus PcpB dechlorinates PCP to yield TeCH and PcpC dechlorinates TeCH to yield TrCH and DiCH. These proteins may be purified from the Flavobacterium as described above or from microorganisms transformed with the recombinant DNA vectors and which, by virtue of being so transformed, produce PcpB and/or PcpC. Suitable transformed microorganisms include the disclosed E. coli clones which are transformed with recombinant DNA vectors pCO221 and pCO303. These vectors encode PcpB and PcpC, respectively. Alternatively, as described in Example 2, the pcpA, pcpB or pcpC genes may be cloned into vectors which are designed to promote the high-level expression of cloned genes. Proteins produced in these microorganism are purified according to the methodologies described for the purification of the proteins from the Flavobacterium. Minor variations in these methodologies to take account of the characteristics of a particular chosen microorganism may be required.

Conditions suitable for the conversion of PCP to TeCH by PcpB and for the conversion of TeCH to TrCH and DiCH by PcpC are given above and may be adapted according to the scale of the desired reaction. An embodiment of the current invention is a composition comprising both purified PcpB and PcpC which is used for the conversion of PCP to DiCH.

Purified PcpB may also be utilized to degrade a range of other compounds as disclosed above.

The use of these purified proteins for the degradation of PCP may involve other embodiments including immobilized enzyme formats in which the purified enzymes are attached to an insoluble surface. Methods suitable for the attachment of proteins such as PcpB and PcpC to insoluble surfaces are well known in the art.

EXAMPLE 2

As described in Example 1, purified PcpB and PcpC may be used for the in vitro dechlorination of PCP. The pcpB and pcpC gene may be cloned into high-level expression vectors in order to promote the levels of PcpB and PcpC protein production. The following example illustrates the use of a high-level expression vector to obtain expression of PcpB in E. coli. In order to obtain high-level expression of the pcpB gene, the gene was excised from the pCO221 vector described above by digestion with the restriction enzymes HpaI and HindIII. HpaI cleaves in the middle of the hexanucleotide GTTAAC, leaving a blunt-ended fragment. This recognition site is present in the pcpB gene sequence at base pairs 211–216 upstream of the ATG initiation codon, as shown in Sequence ID No. 2. The HindIII recognition site is present in the polylinker region of pCO221 located downstream of the pcpB gene. This HpaI-HindIII fragment, therefore, contains the entire pcpB gene. This fragment was cloned into the vector pKK223-3, an expression vector available from Pharmacia LKB Biotechnology, Inc. (Piscataway, N.J.). The pKK223-3 vector was digested with the restriction enzymes SmaI and HindIII. Digestion with the restriction enzyme SmaI leaves a blunt-ended fragment which is compatible with the blunt-ended fragment produced by digestion with HpaI. The HpaI-HindIII pcpB gene fragment was therefore ligated into the SmaI-HindIII digested pKK223-3 vector to create the plasmid pCL3. The construction is shown schematically in FIG. 14. This construction results in the ATG initiation codon of the pcpB gene being located adjacent to the $p_{tac}$ promoter of the pKK223-3 vector. The orientation of the $p_{tac}$ promoter is such that it will drive high-level expression of the pcpB gene when the vector is transformed into E. coli. For the above manipulations, restriction endonucleases, T4 DNA ligase, random-primed DNA labeling kit and isopropyl-β-D-thiogalactopyranoside (IPTG) were purchased from United States Biochemical Corp., Cleveland, Ohio, and used as recommended by the supplier.

Following electroporation of E. coli, JM 105 with 1 ml of the ligation mixture, and colony hybridization with $^{32}$P-dCTP-labeled probe derived from the pcpB gene, the clone CL3 was picked from a large number of negative colonies in the background. The structure of this clone was confirmed to be the structure shown in FIG. 14 by plasmid miniprep from 5 µl overnight culture and digestion with EcoRI.

The production of PcpB in the transformed *E. coli* containing pCL3 was assessed by SDS-PAGE and immunoblotting. Cells were grown in Luria broth with and without the presence of IPTG. Samples were taken from the cultures at hourly intervals and crude proteins extracted from these samples were examined by SDS-PAGE (10% acrylamide) using a Bio-Rad Mini-Protean II apparatus and quantified by the Lowry assay (Lowry et al., 1951). The SDS-PAGE gels were stained with Coomassie Blue and the results of this are shown in FIG. 15, Panel A. The protein molecular weight standards shown in FIG. 15, Panel A, were purchased from Bethesda Research Laboratories, Inc. (Gathersberg, Md.) and are, in descending order: 205, 116, 97, 66, 45 and 29 kDa. Purified PCP hydroxylase (PcpB protein) was loaded into the lane adjacent the molecular weight standards. Immunoblotting of the SDS-PAGE was performed by a slight modification of that described by Bollag and Edelstein (1991) Using a Bio-Rad Mini-Transblot Electrophoretic Transfer Cell. Nonspecific binding of antibody was blocked by a one-hour incubation in 3% gelatin at 37° C. with gentle shaking. A 1:1000 dilution of rabbit polyclonal antibody raised against the purified PcpB protein (prepared commercially by Berkeley Antibody Co., Berkeley, Calif.) was used as the primary antibody to detect the PcpB protein. The bound anti-PcpB antibody was detected with goat anti-rabbit antibody conjugated with alkaline phosphatase, supplied by Tago, Inc. (Burlingame, Calif.) and blot development was performed as described by the manufacturers. The immunoblot resulting from this procedure is shown in FIG. 15, Panel B. The blot confirms the expression of PcpB by the transformed *E. coli* cells.

The activity of the PcpB protein expressed in the transformed *E. coli* was then determined by enzyme assay. *E. coli* JM 105 containing pCL3 was cultured in Luria broth (Maniatis et al., 1992) containing 50 mg/liter ampicillin. The growth of the culture was followed spectrophotometrically, and when the $OD_{600}$ of the culture reached 0.7, IPTG was added to a final concentration of 1 mM. Two to three hours after the addition of IPTG, the culture was centrifuged, and the cells were collected. Cells from one liter of the growth medium were used to prepare cell extracts as described previously for Flavobacterium (Xun and Orser, 1991c.). Forty to 60% ammonium sulphate fractions were dialyzed for four-hours against 0.75 liters of 20 mM Tris-5 mM EDTA solution, pH 8.0, with stirring at 4° C., reprecipitated with 60% ammonium sulphate and then subjected to enzyme assays.

Figure 16A:
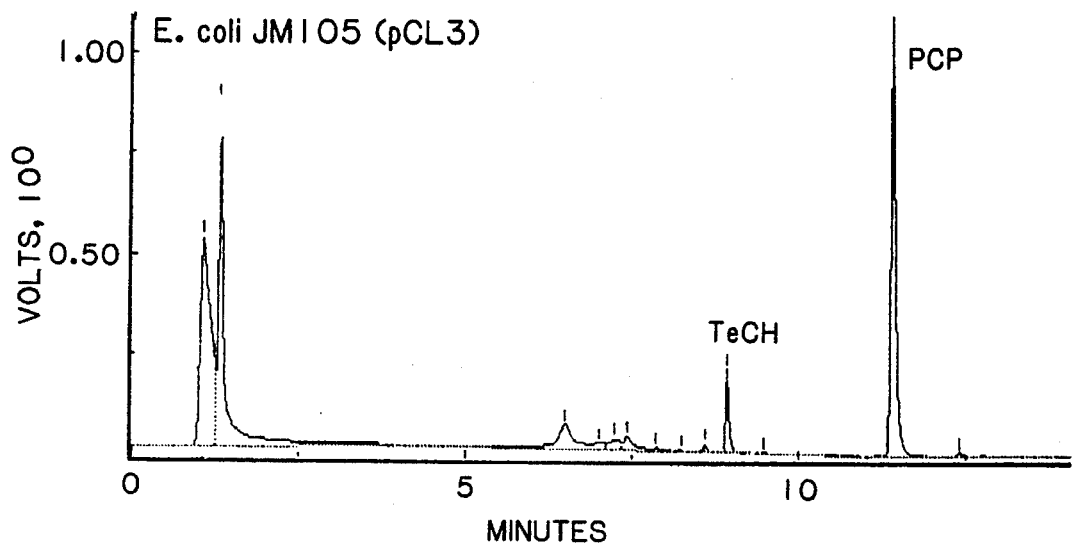
FIG. 16 shows HPLC chromatograms demonstrating the conversion of PCP to TeCH by cell extracts of E. coli JM105 transformed with pCL3.
Figure 16B:
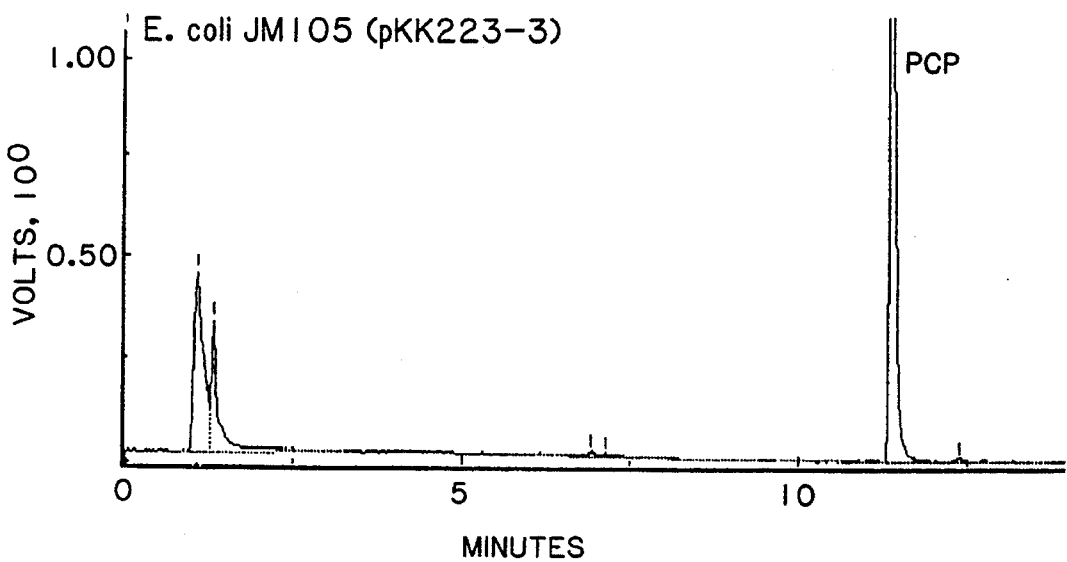

Enzyme assays were performed as described above for the PcpB protein extracted from Flavobacterium, using a Waters HPLC with a Nova-pak C18 column with an $H_3PO_4$-acetonitrile gradient. FIG. 16 shows the results of this HPLC analysis: proteins extracted from *E. coli* transformed with pCL3 and induced with IPTG converted substrate PCP to TeCH, whereas control cells (*E. coli* transformed with pKK223-3 and induced with IPTG) showed no such activity. This experiment confirmed the activity of the pcpB protein in the transgenic *E. coli* cells.

These experiments confirmed that functional PcpB protein was indeed expressed by the recombinant *E. coli* strain transformed with pCL3.

EXAMPLE 3

The cloned DNA molecules which include genes pcpA, pcpB and pcpC which encode the enzymes PcpA, PcpB and PcpC, respectively, and the pcpD and pcpR genes may be utilized in the creation of transgenic microorganisms which possess enhanced PCP dechlorination or degrading ability. Such microorganisms could be used in bioreactors wherein PCP containing material, supplemented with appropriate nutritional additives, would be degraded by these organisms. Alternatively, these microorganisms could be applied directly onto contaminated environmental sites, including PCP contaminated soils and bodies of water. Yet another use for such microorganisms would be the production of the purified proteins. Thus, if these microorganisms were more readily cultured than the Flavobacterium or produced higher levels of the proteins, then such organisms would be preferred for the large scale purification of the proteins. Transformed microorganisms developed according to this invention may be transformed with vectors including one or more of the genes pcpA, pcpB and pcpC. Thus, transformed microorganisms may be transformed with one of the genes selected from the group consisting of pcpA, pcpB and pcpC, or combinations of two of the genes selected from this group or, alternatively, all three of the genes of this group. In transformed microorganisms containing pcpB, the presence of pcpD may enhance the microorganisms ability to degrade PCP or other compounds. The presence of pcpR may be useful in some strains of transformed microorganisms provided by this invention to confer PCP inducibility on the introduced genes.

The disclosed DNA molecules encoding PcpA, PcpB, PcpC, PcpD or PcpR may be transformed into *E. coli* on recombinant vectors, such as vectors based on the cosmid vector pLAFR3 or the phagemid pBluescript as disclosed, or into other microorganisms using the disclosed and/or other vectors and in association with other DNA sequences such as promoters which effect high level expression of the genes. Microorganisms potentially suitable as hosts include, but are not limited to, soil bacteria such as Pseudomonas spp. for in situ application and Bacillus spp. and *E. coli* for bioreactor and protein purification purposes.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar et al. (1977)), pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang et al. (1978); Goeddel et al. (1979)), alkaline phosphatase, the tryptophan (trp) promoter system (Goeddel (1980) and EPO Appln. Publ. No. 36,776) and hybrid promoters such as the tac promoter (H. de Boer et al. (1983)). However, other functional bacterial promoters are suitable. Their nucleotide sequences are generally known, thereby enabling a skilled worker operably to ligate them to DNA encoding PcpA, PcpB, PcpC, PcpD or PcpR (Siebenlist et al. (1980)) using linkers or adaptors to supply any required restriction sites. Promoters for use in bacterial systems also will contain a Shine-Dalgarno (S.D.) sequence operably linked to the DNA encoding growth hormone receptor and binding protein.

Those skilled in the art will recognize that the creation of such transgenic microorganisms is now enabled by this invention and that this approach is not limited to the specific experimental modes and materials described and will appreciate the wider potential utility of this invention.

EXAMPLE 4

Transgenic microorganisms producing the PcpB or PcpC proteins may also be used for the dechlorination of PCP without further purification of the PcpB or PcpC proteins. Thus, the dechlorination of PCP to TeCH may be effected by exposing PCP directly to microorganisms transformed with DNA that encodes the PcpB protein. Furthermore, the TeCH produced as a result of the dechlorination of PCP may be further dechlorinated to TrCH and DiCH by exposure to microorganisms transformed with DNA that encodes the PcpC protein. Alternatively, the dechlorination of PCP to DiCH may be achieved by exposing PCP to microorganisms that are transformed with DNA that encodes both the PcpB and PcpC proteins. The following example serves to illustrate that PcpB activity is exhibited by whole cells of E. coli transformed with the pcpB gene.

E. coli JM105 transformed with pCL3 and E. coli JM105 transformed with pKK223-3 (as a control) produced as described above were cultured in Luria broth supplemented with ampicillin (50 μg/ml) and IPTG (1 mM) at room temperature with shaking. The growth of the culture was followed spectrophotometrically and when the $OD_{600}$ of the culture reached 0.7 (mid-log phase), the cells were pelleted by centrifugation. The cell pellet was then resuspended in minimal medium (M9) supplemented with thiamine, ampicillin (50 μg/ml), IPTG (1 μM), PCP (0.3 mM or 80 PPM) and 10 mM phosphate buffer (pH 7.0) with subsequent gentle shaking at room temperature. As shown in Table 6 below, at specified time points, 600 μl of the culture was removed, the cells pelleted out, and the supernatant evaluated spectrophotometrically at 318 nm.

TABLE 6

| Time | JM105 (pCL3) | JM105 (pKK223-3) |
| --- | --- | --- |
| 10 min | 1.3675 | 0.8718 |
| 20 min | 0.8179 | 0.8210 |
| 30 min | 0.9678 | 0.6407 |
| 40 min | 0.6287 | 0.5354 |
| 50 min | 0.6562 | 0.5915 |
| 60 min | 0.6414 | 0.5707 |
| 70 min | 0.6223 | 0.7768 |
| 80 min | 0.6448 | 0.5487 |
| 120 min | 0.6448 | 0.5486 |
| 660 min | 0.15913 | 0.0471 |

PCP absorbs at 318 nm and therefore the measurements shown in Table 6 above were intended to determine whether the E. coli cultures were removing PCP from the growth medium. Both the JM105 transformed with pCL3 and JM105 transformed with the vector pKK223-3 produced spectrophotometric results which indicated the removal of PCP from the culture. The decrease in absorbance at 318 nm for both cultures is likely explained by the uptake of PCP into the E. coli cells. It is proposed that this occurs because of the lipophilic nature of the PCP and that this uptake is independent of the presence of the particular DNA molecules transformed into the E. coli cells.

Figure 17A:
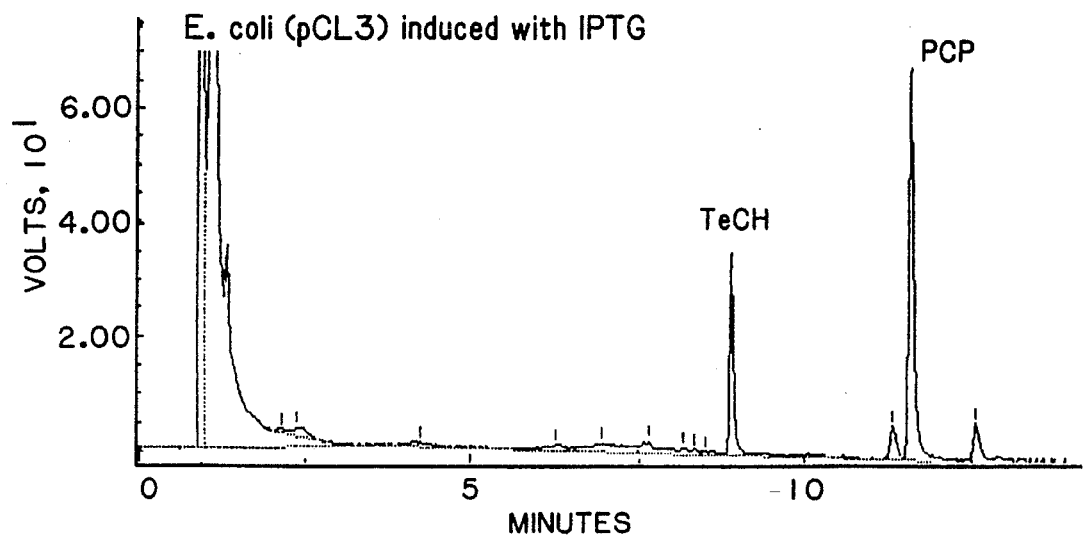
FIG. 17 shows HPLC chromatograms demonstrating the conversion of PCP to TeCH by intact E. coli. JM105 cells transformed with pCL3 and induced with IPTG.
Figure 17B:
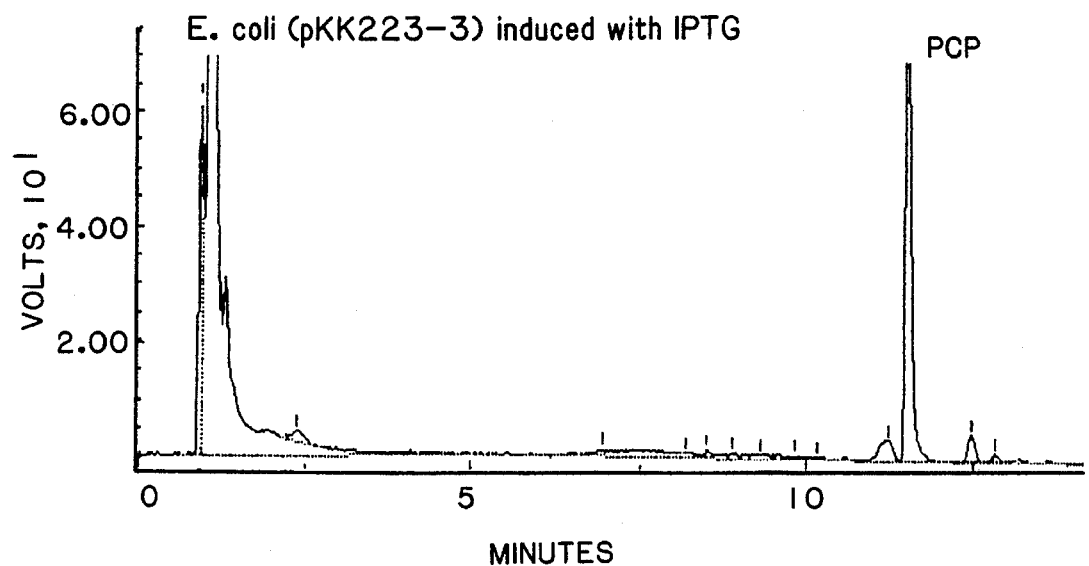

HPLC analysis was employed to confirm the dechlorination of PCP by the intact cell culture of E. coli transformed with pCL3. Samples were removed from the cultures at the 660 minute time point and 20 μl of cells were mixed with 20 μl of acetonitrile. The resulting lysed cellular debris was pelleted out by centrifugation and the supernatant was loaded onto a C18 reverse phase HPLC column, as described above. The resulting chromatograms are shown in FIG. 17. This experiment confirms that PCP breakdown to TeCH did occur in E. coli cells transformed with pCL3 but that no such dechlorination occurred in the control E. coli culture.

These experiments confirm the ability of intact E. coli cells transformed with the pcpB gene to dechlorinate PCP to TECH.

EXAMPLE 5

Example 4 above describes the production of E. coli cells transformed with the pcpB gene which are capable of degrading PCP to TECH. E. coli cells were also transformed with both pcpB and pcpC to demonstrate that cells containing both of these genes could perform subsequent steps in the degradation of PCP.

Essentially, an E. coli strain was constructed to produce high level transcription of a contrived dicistronic message for pcpB and pcpC under the control of the IPTG inducible $P_{tac}$ promoter. Production of DiCH from PCP by crude cell extracts and cultures of this E. coli strain was confirmed by gas chromatography-mass spectrometry and coretention with authentic DiCH by high pressure liquid chromatography. As discussed below, whole cells of the transformed E. coli strains were capable of degrading PCP at high rates in saturated culture and, most notably, degraded PCP more rapidly than Flavobacterium sp. strain ATCC 39723.

Figure 18:
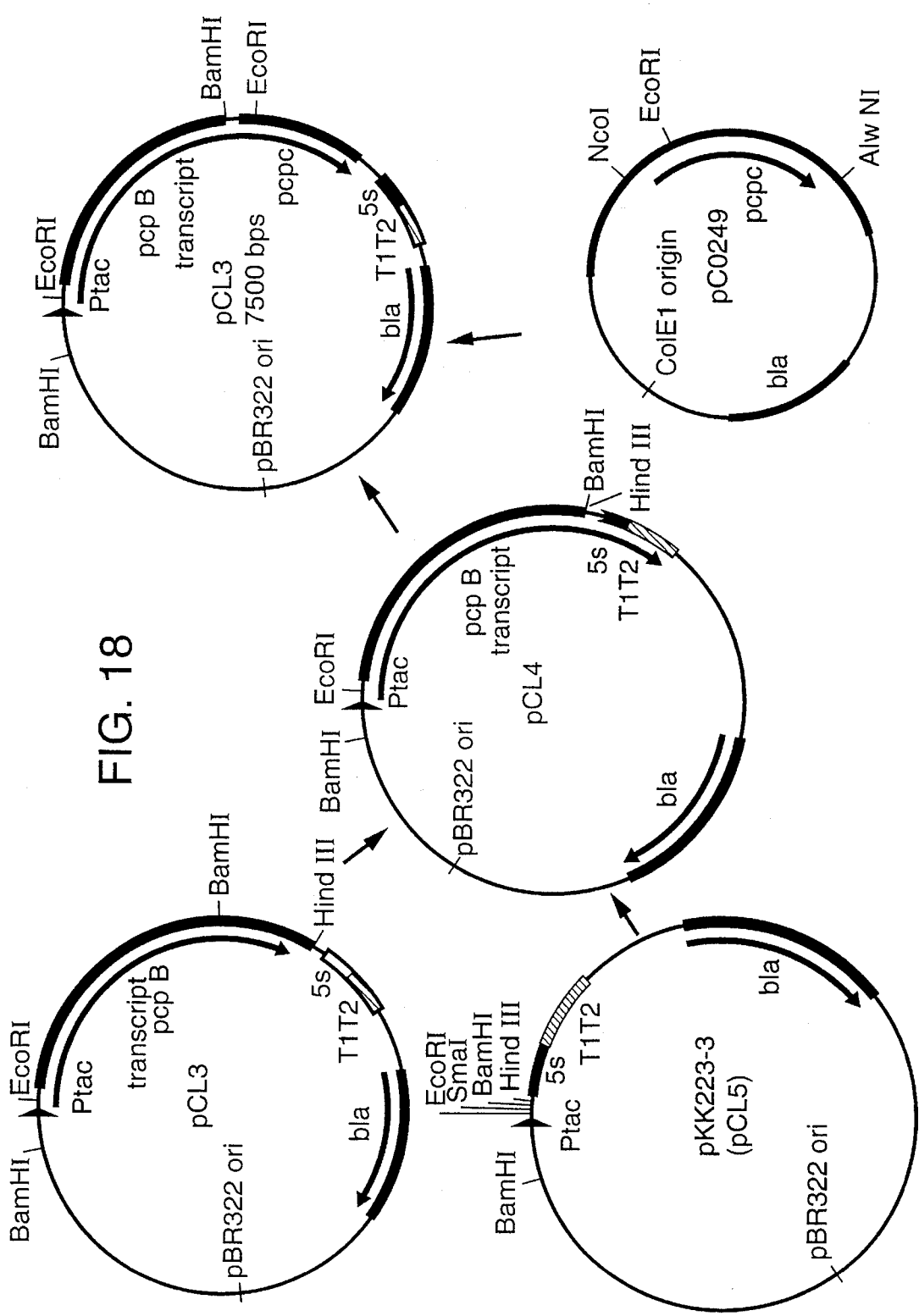
FIG. 18 shows the schematic production of pCL6, a plasmid containing a dicistronic message encoding both pcpB and pcpC.

Construction of a plasmid for transcription of a dicistronic message encoding both PcpB (PCP 4-monooxygenase) and PcpC (TeCH reductive dehalogenase) was accomplished as follows: pCL3, described above, was digested with BamHI to remove the $P_{tac}$-pcpB fragment and this purified fragment was ligated with BamHI cut, alkaline phosphatase treated pKK223-3 (Pharmacia Biotech, Inc.) to generate plasmid pCL4. The plasmid pCO249 containing the pcpC gene and described above, was digested with NcoI and AlwNI to release the pcpC fragments and was mixed with HindIII digested PCL4 DNA. This mixture was incubated with Klenow enzyme to fill in the 5' overhanging ends and then ligated to generate pCL6. The construction of PCL6 is illustrated schematically in FIG. 18.

An E. coli strain transformed with PCL6 was designated E. coli strain CCL6. Northern blot analyses of total RNAs from CCL6 and various controls suggested the creation of a contrived dicistronic message under the control of the IPTG inducible $P_{tac}$ promoter. Protein extracts from E. coli strain CCL6 were tested for the ability to both hydroxylate PCP and to dehalogenate TeCH, the respective activities of pcpB and pcpC. Both activities were confirmed by HPLC chromatography of protein extracts from CCL6 incubated with PCP.

Whole cell PCP degradation curves were obtained by removing timed aloquots from cultures of E. coli strains CCL6 incubated in the presence of PCP. These aloquots were extracted with an equal volume of acetonitrile, followed by a 3 minute centrifugation in a table top centrifuge. The resulting soluble material was then loaded onto a C18 HPLC column and the presence of PCP, TeCH and DiCH were determined by chromatography at 320 nm, 305 nm and 300 nm, respectively. These experiments confirmed the ability of whole cells of E. coli strain CCL6 to convert PCP to DiCH.

Figure 19:
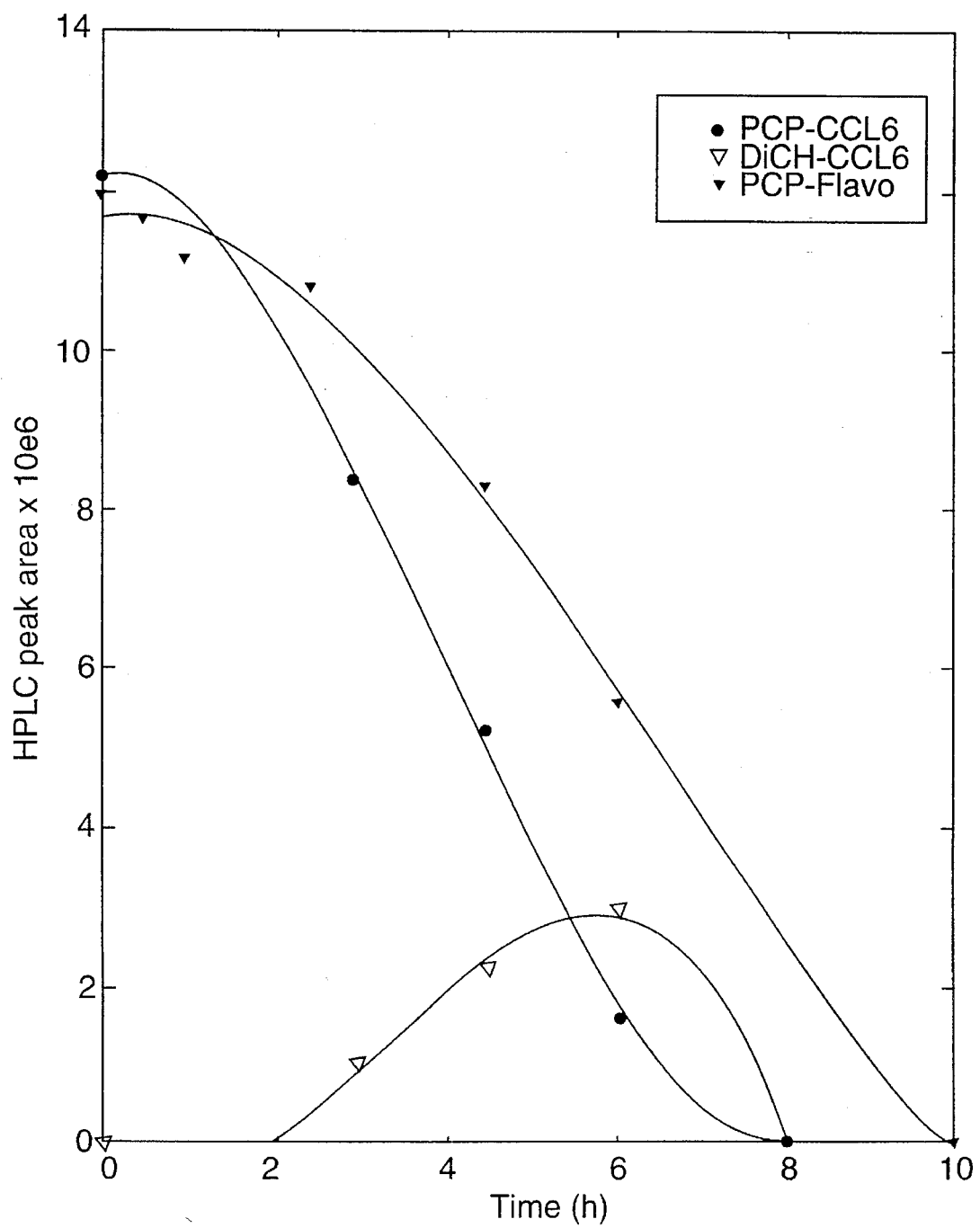
FIG. 19 shows the degradation of PCP by Flavobacterium sp. Strain ATCC 39723 (filled triangles) and by E. coli CC16 (filled circles). The accumulation of DiCH in the CCL6 culture incubated with PCP is also shown (open triangles).

FIG. 19 shows HPLC analyses of the degradation of PCP by both E. coli CCL6 and Flavobacterium sp. Strain ATCC 39723. The results indicate that the *E. coli* transformant culture degraded PCP at a higher rate than the Flavobacterium culture.

These experiments demonstrate the potential utility of genetically engineered microorganisms for the removal of pollutants, including PCP. In many instances, genetically engineered microorganisms can be made more specific for the particular pollutant at issue, can produce more of the required enzymes for biodegradation, and are faster growing than natural isolates. For example, Flavobacterium grows slowly relatively to the *E. coli* recombinant strains used in this experiment. Furthermore, the *E. coli* cells produce significantly greater cell mass per liter-of culture of than Flavobacterium. Additional-experiments, not reported here, have demonstrated that the pcpB gene expressed in *E. coli* retains the wide substrate activity that is found in Flavobacterium.

EXAMPLE 6

The purified proteins PcpA, PcpB and PcpC may also be employed to prepare monoclonal antibodies (MAbs). Methods for making MAbs are well known in the art and are described in publications such as that by Harlow and Lane (1988).

The production of PcpA and PcpB by Flavobacterium sp. Strain ATCC 39723 are induced by the presence of PCP. This finding can be exploited to develop a novel immunoassay method by which the levels of PCP present in a sample taken from a contaminated environmental site may be determined.

MAbs raised against PcpA (or PcpB) are used to determine the levels of PcpA (or PcpB) produced by the organism in response to the presence of PCP in a given sample thereby allowing quantification of PCP in the sample. The following example describes the use of such MAbs raised against PcpA. PcpA is selected as the preferred embodiment because it is produced in the periplasm and is therefore most easily and completely extracted from the cells.

PcpA is purified by the methodology described above. MAbs against the purified protein may be raised in a number of animals, including mice. Methods of raising MAbs include, but are not limited to, the approach described herein: a number of mice (typically 2–6) are injected with a dose of the purified protein (typically 50 µg) as part of an antigen preparation (which may include other compounds such as Freund's adjuvant). Approximately two weeks after this primary immunization, the mice receive a second, booster, inoculation, and thereafter test bleeds are performed on a regular basis to assess the development of the antibody response to PcpA within the mice. Suitable methods for determining the anti-PcpA antibody titer include, but are not limited to, the antibody capture dot blot assay, as described in Harlow and Lane (1988).

In one embodiment of this assay, nitrocellulose paper is incubated in a solution of purified PcpA (at a concentration of 10–50 µg/ml) so as to allow the protein to bind to the paper. Bound protein is subsequently fixed to the paper by incubation in 0.02% sodium azide. Serum extracted from the immunized mice is serially diluted and 1 µl samples of each dilution are spotted onto the paper. Unbound antibodies are removed by washing and the presence of mouse anti-PcpA antibodies attached to the bound PcpA is then detected using $^{125}$I-labeled rabbit anti-mouse immunoglobulin. The antibody titer is determined by the highest dilution of the serum which shows the presence of anti-PcpA antibodies.

Further booster inoculations are provided as necessary in order to raise the anti-PcpA titer. A mouse with a high anti-PcpA titer is selected for hybridoma production. Antibody-secreting cells are prepared from the mouse, mixed with myeloma cells and fused. Following fusion, the resultant hybridoma cells are diluted in selective medium and plated in multi-well culture dishes. The hybridomas are screened for the production of anti-PcpA antibodies and cells from positive wells are single-cell cloned. MAbs produced from these cloned cell lines may be harvested from tissue culture Supernatants or ascitic fluid.

In order to assess the level of PCP contamination at a given environmental site, samples taken from the site are serially diluted and the diluted samples incubated with cells of Flavobacterium sp. Strain ATCC 39723. Following an incubation period of preferably not less than 20 minutes to allow induction of PcpA, the samples are treated to release induced PcpA. Suitable treatments for the release of PcpA from the periplasmic space of the bacteria are described earlier in this work.

The levels of induced PcpA are then determined by immunoassay using MAbs raised against PcpA. Various methods for such an immunoassay are well known in the art (Harlow and Lane, 1988). A version of the antibody capture assay may be employed for this purpose. In one embodiment of this assay, samples of the protein released from the periplasmic space of the treated cells are spotted onto nitrocellulose paper. The paper is then incubated firstly with anti-PcpA MAbs and then with $^{125}$I labeled rabbit anti-mouse immunoglobulin. Exposure of the treated nitrocellulose to X-ray film subsequently allows the presence of PCP in the original sample to be detected. The amount of PCP in each sample is determined in reference to test standards created by adding known amounts of PCP to cells and then following the above procedure. Levels of PCP in particular samples are then calculated from those highest dilutions of each sample which give a positive induction response.

EXAMPLE 7

Monoclonal antibodies to each of the purified proteins can be used to assess the levels of PcpA, PcpB or PcpC production by new isolates of PCP degrading Flavobacteria or other species under a variety of conditions. MAbs may be used to quantitate the production of these proteins by a variety of methods, including antibody capture assays as described in Example 2 and by Harlow and Lane (1988) (chapter 14), which is incorporated by reference. This type of assay can be used to determine optimal conditions for PCP breakdown by providing quantitation of the levels of these proteins under a variety of conditions. Conditions which result in elevated levels of PcpA, PcpB and PcpC are optimal for PCP breakdown activity.

EXAMPLE 8

The cloned genes, or portions of these genes, may be used as probes to clone homologous genes from other microorganisms which display the ability to degrade PCP, halogenated aromatics or other substituted aromatics. In this way, genes which encode enzymes exhibiting differing substrate specificities may be obtained which, in turn, will widen the range of environmental contaminants that can be treated by novel bioremediation approaches.

By way of demonstration of the utility of the genes for this purpose, DNA was extracted from four microorganisms with known PCP breakdown activity (Flavobacterium ATCC 39723, Pseudomonas SR3, Arthrobacter ATCC 33790 and *Rhodococcus chlorophenolicus*) and a related fifth organism (Arthrobacter DSM 20407) which lacks this activity. Pseudomonas SR3 was obtained from Dr. Peter Chapman, United States Environmental Protection Agency, Florida Gulf Breeze Station, *Rhodococcus chlorophenolicus* was obtained from Dr. R. Crawford, University of Idaho and the other isolates were obtained from culture collections.

The DNAs were digested with EcoRI, electrophoresed and Southern blotted according to Sambrook et al. (1989). Southern blots were subsequently probed with [$\alpha$-$^{32}$P] dCTP labeled probes derived from the cloned genes. Hybridization was performed in 6×SSC (0.9M NaCl) at 65° C., filters were washed in 0.3×SSC (0.045M NaCl) at 65° C. Hybridization results are tabulated in Table 4. Three of the four strains with known PCP degrading activity each showed a single hybridizing band with each of the three gene probes indicating the presence of homologous genes. DNA from *Rhodococcus chlorophenolicus* did not show hybridization under the stringent conditions used; it is proposed that the genes encoding enzymes of the PCP degrading pathway of this organism are less homologous to the gene probes than those of the other organisms. Hybridization under less stringent conditions may be used to detect genes with weaker homology. No hybridization was observed to the DNA of the control strain, Arthrobacter DSM 20407.

TABLE 7

| Probe fragments: | pcpA 2.3 kb EcoRI/ AccI | pcpB 2.3 kb EcoRI/ BamHI | pcpC 0.7 kb EcoRI |
|---|---|---|---|
| Microorganism | | | |
| *Flavobacterium sp.* ATCC 39723 | 5.5 kb | 3.0 kb | 0.7 kb |
| Pseudomonas SR3 | 5.0 kb | 3.0 kb | 1.3 kb |
| Arthrobacter ATCC 33790 | 5.0 kb | 3.0 kb | 1.3 kb |
| Arthrobacter DSM 20407 | — | — | — |
| *Rhodococcus chlorophenolicus* | — | — | — |

The hybridizing DNA of these strains may be cloned and the PCP breakdown genes identified using the strategies outlined herein.

EXAMPLE 9

It is frequently desirable to assess contaminated environments for the presence of microbial populations capable of breaking down the particular contaminants present in these environments, in order to determine suitable decontamination strategies. In accordance with the present invention, a novel, highly sensitive method of detecting the presence of microorganisms capable of breaking down PCP is presented. Microorganisms which possess PCP breakdown activity and which thus carry DNA sequences homologous to either pcpA, pcpB or pcpC, may be detected by this method.

Southern hybridization, as described in Example 9, may be utilized directly to detect these organisms. However, these microbial populations are often not readily cultured in the laboratory and so such this approach may be unsatisfactory.

A combination of the polymerase chain reaction (PCR) and DNA hybridization offers a much more sensitive method for detection of such microorganisms; it does not require the culturing of the microorganisms and is theoretically capable of detecting a single microorganism in a given sample. The detection of other types of microorganisms in environmental samples using primers derived from other cloned genes is discussed by Atlas and Bej (1990).

DNA primers suitable for use in the PCR may be derived from the sequences of either pcpA, pcpB or pcpC. Methods for designing primers are well known in the art and are disclosed in publications including Innis et al. (1990). The cloning of genes from other organisms as described in Example 9 above would allow the determination of highly conserved regions of these genes. The selection of primers from such highly conserved regions for use in the PCR would ensure the detection of a wide range of PCP degrading organisms by avoiding less well conserved sequence regions.

Environmental samples are treated to extract microorganisms and the organisms are lysed to release DNA. The samples are then subjected to the PCR in the presence of the appropriate primers. DNA sequences amplified by the PCR are then detected by Southern blotting or dot blotting using labeled DNA probes corresponding to the amplified DNA regions of the gene from which the probes were derived, as described by Atlas and Bej (1990). The detection of hybridizing, amplified DNA indicates the presence of PCP degrading microorganisms in the sample.

Having illustrated and described the principles of purifying the proteins, cloning the genes encoding these enzymes and modes of use of these purified proteins and their corresponding genes, it should be apparent to one skilled in the art that the invention can be modified in arrangement and detail without departing from such principles. We claim all modifications coming within the spirit and scope of the claims presented herein.

BIBLIOGRAPHY

Altschul et al. (1990). "Basic Local Alignment Search Tool," *J. Mol. Biol.* 215:403–410.

American Public Health Association 1989. Standard Methods for the Examination of Water and Wastewater, 17th Ed., American Public Health Association, Washington, D.C.

Apajalati and Salkinoja-Salonen 1987a. *J. Bacteriol.* 169:675–681.

Apajalati and Salkinoja-Salonen 1987b. *J. Bacteriol.* 169:5125–5130.

Atlas and Bej (1990) in Innis et al. (eds.), PCR Protocols, a Guide to Methods and Applications. Academic Press Inc., San Diego, Calif.

Birnboim and Doly (1979). *Nucleic Acids Res.* 7:1513–1515.

Black and Whittle (1967). *J. Am. Water Works Assoc.* 59:471–490.

Bolivar et al. (1977). *Gene* 2:95.

Bollag and Edelstein (1991). *Protein Methods.* Wiley-Liss, Inc.

Bradford (1976). *Anal. Biochem.* 72:248–254.

Brunel and Davison (1988). *J. Bacteriol.* 170:4924–4930.

Chang et al. (1978). *Nature* 275:615.

Commandeur and Parsons (1990). *Biodegradation* 1:207–220.

Correll et al. (1992). *Science* 258:1604–1610.

H. de Boer et al. (1983). *Proc. Natl. Acad. Sci. U.S.A.* 80:21–25.

Engelhardt et al. (1986). *Toxicol. Environ. Chem.* 11:233–252.

Flashner and Massey (1974). Flavoprotein Oxygenases, pp. 245–283. In O. Hayaishi (ed.), Molecular Mechanisms of Oxygen Activation. Academic Press, Inc., New York.

Frantz and Chakrabarty (1987). *Proc. Natl. Acad. Sci. U.S.A.* 84:4460–4464.

Friedman et al. (1982). *Gene* 18:289–296.

Goeddel et al. (1979). *Nature* 281:544.

Goeddel (198). *Nucleic Acids Res.* 8:4057; EPO Appln. Publ. No. 36,776.

Harlow and Lane (1988). Antibodies, a Laboratory Manual. Cold Spring Harbor Laboratory, New York.

Innis et al. (1990). PCR Protocols, a Guide to Methods and Applications. Academic Press Inc., San Diego, Calif.

Ishida et al. (1988). *Biochem. Biophys. Res. Commun.* 156:681–688.

Jacoby and Habig (1980). Glutathione transferases. In W. B. Jacoby (ed.), Enzymatic Basis of Detoxication, Vol. 2, p. 63–94, Academic Press, New York.

Mason and Cammack (1992). *Ann. Rev. Microbiol.* 46:277–305.

Lowry et al. (1951). J. Biol. Chem. 193:265–275.

Magee and Burris (1954). *Amer. J. Bot.* 41:777–782.

Maniatis et al. (1982). Molecular Cloning: A Laboratory Manual. Cold Spring Harbor Laboratory, Cold Spring Harbor, N.Y.

Mayhew and Massey (1969). *J. Biol. Chem.* 244:794–802.

Messing et al. (1981). *Nucl. Acids Res.* 9:309–321.

Mullis and Faloona (1987). *Methods Enzymol.* 155:335–350.

Nagashima (1984). *Anal. Chem.* 56:1944–1948.

Orser et al. (1993). *J. Bacteriol,* 175:411–416.

Radehaus and Schmidt (1992). *Appl. Environ. Microbiol.* 58:2879–2885.

Rao (1977). Pentachlorophenol: Chemistry, Pharmacology and Environmental Toxicology. Plenum Publishing Corp., New York.

Reiner et al. (1977) in Rao (ed.), Pentachlorophenol: Chemistry, Pharmacology and Environmental Toxicology. Plenum Publishing Corp., New York.

Resnick and Chapman (1994). *Biodegradation* 5:47–54.

Saber and Crawford (1985). *Appl. Environ. Microbiol.* 50:1512–1528.

Saiki et al. (1985). *Science* 230:1350–1354.

Saiki et al. (1988). *Science* 239:487–491.

Sambrook et al. (1989). Molecular Cloning, 2nd ed. Cold Spring Harbor Laboratory, Cold Spring Harbor, N.Y.

Sanger et al. (1977). *Proc. Natl. Acad. Sci. U.S.A.* 74:5463–5467.

Schenk et al. (1989). *J. Bacteriol.* 171:5487–5491.

Schneider et al. (1994). Development of a genetic system for the molecular analysis of pentachlorophenol degradation by Flavobacterium sp. strain ATCC 39723. Abstracts of the American Society for Microbiology General Meeting, Las Vegas, Nev.

Siebenlist et al. (1980). *Cell* 20:269.

Stanlake and Finn (1982). *Appl. Environ. Microbiol.* 44:1421–1427.

Staskawicz et al. (1987). *J. Bacteriol.* 169:5789–5794.

Steiert and Crawford (1986). *Biochem. Biophy. Res. Commun.* 141:825–830.

Steiert et al. (1987). *Appl. Environ. Microbiol.* 53:907–910.

Tietze (1969). *Anal. Biochem.* 27:502–522.

Topp and Akhtar (1990). *Can. J. Microbiol.* 36:495–499.

Topp et al. (1992). *Appl. Environ. Microbiol.* 58:502–506.

Xun and Orser (1991a). *J. Bacteriol.* 173:2920–2926.

Xun and Orser (1991b). *Biochem. & Biophys. Res. Comm.* 174:43–48.

Xun and Orser (1991c). *J. Bacteriol.* 173:4447–4453.

Xun et al. (1992a). *J. Bacteriol.* (In press).

Xun et al. (1992b). *Biochem. & Biophys. Res. Comm.* 182:361–366.

---

We claim:

1. A purified DNA molecule encoding the protein tetrachloro-p-hydroquinone reductase (PcpC).

2. A purified and isolated DNA molecule selected from the group consisting of:
   (a) a DNA molecule comprising nucleotide bases 388 to 1140 shown in SEQ I.D. NO. 3 or its complementary strand; and
   (b) DNA molecules of at least 20 nucleotides in length which hybridize under conditions of at least 75% stringency to DNA molecules defined in (a).

3. A purified and isolated DNA molecule encoding tetrachloro-p-hydroquinone reductase, wherein the DNA molecule hybridizes under conditions of at least 75% stringency with a DNA probe LX-7.

4. A purified and isolated DNA molecule isolated from Flavobacterium sp. strain ATCC 39723 and encoding tetrachloro-p-hydroquinone reductase, said DNA molecule comprising a DNA molecule selected from the group consisting of:
   (a) a 4.0 kb EcoRV-PstI DNA molecule isolated from the Flavobacterium sp. which DNA molecule hybridizes under conditions of at least 75% stringency with the DNA probe LX-7; and
   (b) DNA molecules which hybridize under conditions of at least 75% stringency to the DNA molecules defined in (a).

5. A purified DNA molecule comprising a DNA sequence encoding an enzyme that catalyzes the conversion of tetrachloro-p-hydroquinone to 2,3,6-trichloro-p-hydroquinone.

6. A purified DNA molecule comprising a DNA sequence encoding an enzyme that catalyzes the conversion of 2,3,6-trichloro-p-hydroquinone to 2,6 dichloro-p-hydroquinone.

7. A purified DNA molecule comprising a DNA sequence encoding an enzyme that catalyzes the conversion of tetrachloro-p-hydroquinone to 2,6 dichloro-p-hydroquinone.

8. A recombinant vector including the DNA molecule of claim 7.

9. A transformed microorganism containing the recombinant vector of claim 8.

10. A transformed microorganism containing the DNA molecule of claim 1.

11. A transformed microorganism containing the DNA molecule of claim 2.

12. A transformed microorganism containing a purified DNA molecule encoding pentachlorophenol hydroxylase (PcpB) and a purified DNA molecule encoding tetrachloro-p-hydroquinone reductase (PcpC).

13. A recombinant vector including a DNA molecule encoding tetrachloro-p-hydroquinone reductase (PcpC).

14. The recombinant vector of claim 13 wherein the vector also includes a DNA molecule encoding pentachlorophenol hydroxylase (PcpB).

15. The recombinant vector of claim 14 wherein the DNA molecules encoding PcpC and PcpB are arranged to form a dicistronic message.

16. A transformed microorganism containing the vector of claim 15.

17. A purified and isolated DNA molecule according to claim 2 wherein the molecule comprises nucleotide bases 388 to 1140 shown in Seq. I.D. No. 3, or its complementary strand.

18. A purified and isolated DNA molecule according to claim 2 wherein the DNA molecule is of at least 25 nucleotides in length and hybridizes under conditions of at least 90% stringency to the DNA molecule defined in part (a) of claim 2.

19. A purified DNA molecule encoding the amino acid sequence set forth in Seq. I.D. No.

* * * * *

UNITED STATES PATENT AND TRADEMARK OFFICE
CERTIFICATE OF CORRECTION

Page 1 of 3

PATENT NO.  :  5,512,478

DATED       :  April 30, 1996

INVENTOR(S) :  Orser et al.

It is certified that error appears in the above-identified patent and that said Letters Patent is hereby corrected as shown below:

On the title page, item [75]:

In the Inventors:

Cleston C. Lange, II should be deleted.

Item [56] In Other Publications:

"Microbiol. 4 1512" should read --Microbiol. 1512--.

Column 1, lines 5-13, "The government . . . USDA-NRICGP. (paragraph) This application . . . abandoned." should read --This application . . . abandoned. (paragraph) The government . . . USDA-NRICGP.--.

Column 5, line 60, "PcP" should read --PCP--.

UNITED STATES PATENT AND TRADEMARK OFFICE
CERTIFICATE OF CORRECTION

PATENT NO. : 5,512,478

DATED : April 30, 1996

INVENTOR(S) : Orser et al.

It is certified that error appears in the above-identified patent and that said Letters Patent is hereby corrected as shown below:

Column 9, line 21, "2PcP" should read --2PCP---.

Column 9, line 22, "PCP" should read --PCP---.

Column 11, line 1, "PcpD" should read --PcpB--.

Column 11, line 14, "12,0001b/in$^2$." should read -- 12,000lb/in$^2$.--.

Column 13, line 11, "TECH" should read --TeCH--.

Column 14, line 61, "TECH" should read --TeCH--.

Column 16, line 18, "50∥1." should read –50 $\mu l$.--.

Column 19, line 8, "TECH" should read --TeCH--.

Column 19, line 52, "N2" should read -- N$_2$--.

Column 21, line 51, "upon" should read --Upon--.

Column 24, line 11, "9' of" should read --9 of--.

Column 26, line 34, "CCLS" should read --CCL8--.

UNITED STATES PATENT AND TRADEMARK OFFICE
CERTIFICATE OF CORRECTION

PATENT NO. : 5,512,478

DATED : April 30, 1996

INVENTOR(S) : Orser et al.

It is certified that error appears in the above-identified patent and that said Letters Patent is hereby corrected as shown below:

Column 26, line 35, "pCLS" should read --pCL8--.

Column 27, line 6, "pCLS" should read --pCL8--.

Column 28, line 47, "than-25" should read --than 25--.

Column 37, line 14, "Additional-experiments" should read --Additional experiments--.

Column 38, line 9, "Supernatants" should read --supernatants--.

Signed and Sealed this

Twelfth Day of December, 2000

Attest:

Q. TODD DICKINSON

*Attesting Officer*                *Director of Patents and Trademarks*